US012637435B2

(12) United States Patent
Yamakawa et al.

(10) Patent No.: US 12,637,435 B2
(45) Date of Patent: May 26, 2026

(54) NITROGEN-CONTAINING HETEROCYCLIC COMPOUND OR SALT THEREOF, USE THEREOF, AND INTERMEDIATE THEREOF

(71) Applicant: FUJIFILM Corporation, Tokyo (JP)

(72) Inventors: Takayuki Yamakawa, Ashigarakami-gun (JP); Yasuhiro Tsutsui, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 588 days.

(21) Appl. No.: 18/160,690

(22) Filed: Jan. 27, 2023

(65) Prior Publication Data

US 2023/0167074 A1 Jun. 1, 2023

Related U.S. Application Data

(63) Continuation of application No. PCT/JP2021/028067, filed on Jul. 29, 2021.

(30) Foreign Application Priority Data

Jul. 30, 2020 (JP) ................................ 2020-128832

(51) Int. Cl.

| | |
|---|---|
| ***A61P 43/00*** | (2006.01) |
| ***A61P 35/02*** | (2006.01) |
| ***C07D 213/80*** | (2006.01) |
| ***C07D 213/82*** | (2006.01) |
| ***C07D 241/24*** | (2006.01) |
| ***C07D 241/26*** | (2006.01) |
| ***C07D 241/28*** | (2006.01) |
| ***C07D 401/12*** | (2006.01) |
| ***C07D 405/04*** | (2006.01) |
| ***C07D 405/12*** | (2006.01) |
| ***C07D 405/14*** | (2006.01) |
| ***C07D 413/14*** | (2006.01) |
| *A61P 35/00* | (2006.01) |

(52) U.S. Cl.

CPC ............ *C07D 241/28* (2013.01); *A61P 35/02* (2018.01); *C07D 401/12* (2013.01); *C07D 405/04* (2013.01); *C07D 405/12* (2013.01); *C07D 405/14* (2013.01); *C07D 413/14* (2013.01)

(58) Field of Classification Search

None

See application file for complete search history.

(56) References Cited

U.S. PATENT DOCUMENTS 12,421,217 B2 9/2025 Yamakawa et al.
2010/0074898 A1* 3/2010 Castro Palomino Laria ............... A61P 29/00 546/310
2011/0212945 A1 9/2011 Castro Palomino Laria et al.

(Continued)

FOREIGN PATENT DOCUMENTS

JP 2010-513362 A 4/2010
JP 2010-535824 A 11/2010

(Continued)

OTHER PUBLICATIONS

STN, 2760574-31-8 Registry, Feb. 25, 2022 (Year: 2022).*
STN, 2760573-86-0 Registry, Feb. 25, 2022 (Year: 2022).*
Office Action dated Jan. 23, 2024 in Japanese Application No. 2022-539556.
Extended European Search Report issued Sep. 22, 2023 in European Application No. 21850268.0.
International Search Report dated Aug. 31, 2021, issued in International Application No. PCT/JP2021/028067.

(Continued)

*Primary Examiner* — Kortney L. Klinkel
*Assistant Examiner* — Alison Azar Salamatian
(74) *Attorney, Agent, or Firm* — Sughrue Mion, PLLC

(57) ABSTRACT

An object of the present invention is to provide a compound useful as an anti-tumor agent or the like; an intermediate thereof; and a pharmaceutical composition, an anti-tumor agent, and a dihydroorotate dehydrogenase inhibitor, each of which contains the compound. According to the present invention, there is provided a compound represented by General Formula (1) or a salt thereof:

(1)

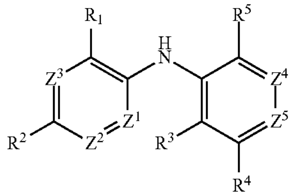

in the formula, $Z^1$, $Z^2$, and $Z^3$ are the same as or different from each other and represent a nitrogen atom or CH; $Z^4$ represents a nitrogen atom or a general formula of $CR^6$; $Z^5$ represents a nitrogen atom or a general formula of $CR^7$ provided that at least one of $Z^1$, $Z^2$, $Z^3$, $Z^4$, or $Z^5$ represents a nitrogen atom; $R^1$ represents a general formula of $CONHR^8$ or the like; $R^2$ represents a $C_{3-8}$ cycloalkyl group which may be substituted or the like; $R^3$, $R^5$, $R^6$, and $R^7$ are the same as or different from each other and represent a hydrogen atom, a halogen atom, or the like; $R^4$ represents an aryl group which may be substituted or a heterocyclic group which may be substituted; $R^8$ represents a general formula of $SO_2R^9$ or the like; and $R^9$ represents an amino group which may be protected or the like.

14 Claims, No Drawings

(56) References Cited

U.S. PATENT DOCUMENTS

| | | | |
|---|---|---|---|
| 2011/0280831 | A1 | 11/2011 | Godessart Marina et al. |
| 2012/0294854 | A1 | 11/2012 | Castro Palomino Laria et al. |
| 2015/0299189 | A1 | 10/2015 | Tanaka et al. |
| 2020/0079727 | A1 | 3/2020 | Yang et al. |
| 2022/0259185 | A1 | 8/2022 | Yamakawa et al. |

FOREIGN PATENT DOCUMENTS

| | | | | |
|---|---|---|---|---|
| JP | 2012-515737 | A | 7/2012 | |
| WO | WO-2009021696 | A1 * | 2/2009 | .............. A61P 37/00 |
| WO | 2014/069510 | A1 | 5/2014 | |
| WO | 2016/044666 | A1 | 3/2016 | |
| WO | 2018/157843 | A1 | 9/2018 | |
| WO | 2019/235571 | A1 | 12/2019 | |
| WO | 2021/085582 | A1 | 5/2021 | |

OTHER PUBLICATIONS

Written Opinion dated Aug. 31, 2021, issued in International Application No. PCT/JP2021/028067.

International Preliminary Report on Patentability (with translation of Written Opinion) dated Jan. 31, 2023, issued in International Application No. PCT/JP2021/028067.

Office Action issued Jun. 4, 2024 in Japanese Application No. 2022-539556.

Notice of Allowance issued Jun. 3, 2025, in U.S. Appl. No. 17/732,717.

Wang et al., Discovery of a potent tyrosine kinase AXL Inhibitor bearing the 3-((2,3,4,5-tetrahydro-1H-benzo[d]asepin-7-yl) amino pyrazine core (Bioorganic & Medicina; chemistry Letters, 29, 836-838, Available Online Jan. 21, 2019) (Year: 2019).

Extended European Search Report dated Oct. 20, issued in European U.S. Appl. No. 17/732,717, corresponding to U.S. Appl. No. 17/732,717.

Office Action issued Apr. 18, 2023 in Japanese Application No. 2021-553708, corresponding to U.S. Appl. No. 17/732,717.

Office Action dated Feb. 7, 2023 in Japanese Application No. 2021-553708, corresponding to U.S. Appl. No. 17/732,717.

International Search Report dated Dec. 22, 2020 in International Application No. PCT/JP2020/040744, corresponding to U.S. Appl. No. 17/732,717.

Written Opinion of the International Searching Authority dated Dec. 22, 2020 in International Application No. PCT/JP2020/040744, corresponding to U.S. Appl. No. 17/732,717.

International Preliminary Report on Patentability dated May 3, 2022 in International Application No. PCT/JP2020/040744, corresponding to U.S. Appl. No. 17/732,717.

* cited by examiner

NITROGEN-CONTAINING HETEROCYCLIC COMPOUND OR SALT THEREOF, USE THEREOF, AND INTERMEDIATE THEREOF

CROSS-REFERENCE TO RELATED APPLICATIONS

This application is a Continuation of PCT International Application No. PCT/JP2021/028067 filed on Jul. 29, 2021, which claims priority under 35 U.S.C § 119(a) to Japanese Patent Application No. 2020-128832 filed on Jul. 30, 2020. Each of the above application(s) is hereby expressly incorporated by reference, in its entirety, into the present application.

BACKGROUND OF THE INVENTION

1. Field of the Invention

The present invention relates to a nitrogen-containing heterocyclic compound or a salt thereof, which is useful as an anti-tumor agent or the like, and an intermediate thereof. The present invention further relates to a pharmaceutical composition, an anti-tumor agent, and a dihydroorotate dehydrogenase inhibitor, each of which contains the nitrogen-containing heterocyclic compound or the salt thereof.

2. Description of the Related Art

Cancer is a major health problem in modern medicine and is one of the leading causes of death in developed countries. Examples of major cancers include blood cancers and solid cancers.

Blood contains blood cells such as erythrocytes, leukocytes, and platelets, which are produced by cell growth and differentiation (a transition from an immature cell into a mature cell) from hematopoietic stem cells, which are the source of blood cells, in the bone marrow inside the bones. Blood cancers develop in a case where some kind of genetic abnormality occurs in myeloblasts, which are immature blood cells in the process by which blood is created, and then cancerous cells (leukemia cells) proliferate indefinitely.

On the other hand, WO2014/069510A discloses a pyrazine derivative which has an excellent keratinocyte growth inhibitory effect and is useful for the treatment such as prevention or treatment of diseases involving overgrowth of keratinocytes.

In addition, WO2019/235571A discloses a pyridine derivative which is useful for the treatment of blood cancers.

SUMMARY OF THE INVENTION

There are various therapeutic methods for the treatment of blood cancers such as chemotherapy, radiotherapy, molecularly targeted therapy, and high-dose chemotherapy combined with hematopoietic stem cell transplantation. Nonetheless, the number of deaths from blood cancer is increasing, there are problems such as resistance to therapeutic drugs, and no cure has been established.

In addition, many solid cancers have a poor prognosis, for which no effective therapeutic method has been established yet. In addition, those cancer cells proliferate in an autonomous and uncontrolled manner, which leads to a problem of rapid cancer cell growth, and therefore there is a need for an effective therapeutic method for solid cancers.

Various methods are known as methods for the prevention or treatment of cancers, but the effects of those methods are not satisfactory and more effective anti-tumor agents are desired. An object of the present invention is to provide a nitrogen-containing heterocyclic compound or a salt thereof, which is useful as an anti-tumor agent or the like, and an intermediate thereof. Another object of the present invention is to provide a pharmaceutical composition, an anti-tumor agent, and a dihydroorotate dehydrogenase inhibitor, each of which contains the nitrogen-containing heterocyclic compound or the salt thereof.

The present invention has been made in view of such circumstances. As a result of extensive studies, the present inventors have found that a compound represented by General Formula (1) or a salt thereof has an excellent dihydroorotate dehydrogenase (hereinafter, also referred to as DHODH) inhibitory effect and is useful as a DHODH inhibitor. In addition, the present inventors have found that the compound represented by General Formula (1) or the salt thereof has an excellent anti-tumor activity and is useful as an anti-tumor agent. The present invention has been completed based on these findings.

The present invention provides the followings.

[1]

A compound represented by General Formula (1) or a salt thereof:

(1)

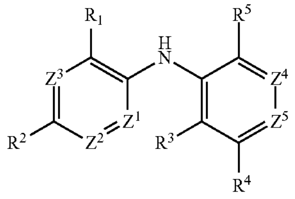

in the formula, $Z^1$, $Z^2$, and $Z^3$ are the same as or different from each other and represent a nitrogen atom or CH;

$Z^4$ represents a nitrogen atom or a general formula of $CR^6$;

$Z^5$ represents a nitrogen atom or a general formula of $CR^7$;

provided that at least one of $Z^1$, $Z^2$, $Z^3$, $Z^4$, or $Z^5$ represents a nitrogen atom;

$R^1$ represents a general formula of $CONHR^8$, a general formula of $CH_2NHR^8$, $CH_2OH$, $CH(OH)CH_3$, $C(O)CH_3$, CHO, Formula (1-1), Formula (1-2), or Formula (1-3);

(1-1)

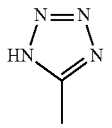

(1-2)

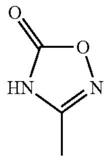

-continued (1-3)

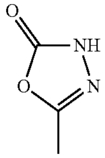

$R^2$ represents a $C_{1-6}$ alkyl group which may be substituted or a $C_{3-8}$ cycloalkyl group which may be substituted;

$R^3$, $R^5$, $R^6$, and $R^7$ are the same as or different from each other and represent a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted;

$R^4$ represents an aryl group which may be substituted or a heterocyclic group which may be substituted;

$R^8$ represents a hydrogen atom, a hydroxyl group which may be protected, an amino group which may be protected, a $C_{1-6}$ alkyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a general formula of $SO_2R^9$; and $R^9$ represents a hydroxyl group which may be protected, an amino group which may be protected, a $C_{1-6}$ alkyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, or a di($C_{1-6}$ alkyl)amino group which may be substituted.

[2]

The compound or salt thereof according to [1], in which $Z^1$ is a nitrogen atom, $Z^2$ is CH, $Z^3$ is a nitrogen atom or CH, $Z^4$ is a general formula of $CR^6$, and $Z^5$ is a general formula of $CR^7$.

[3]

The compound or salt thereof according to [1] or [2], in which $R^2$ is a $C_{1-6}$ alkyl group or a $C_{3-8}$ cycloalkyl group.

[4]

The compound or salt thereof according to any one of [1] to [3], in which $R^1$ is a general formula of $CONHR^8$, Formula (1-1), Formula (1-2), or Formula (1-3).

(1-1)

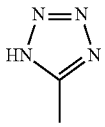

-continued (1-2)

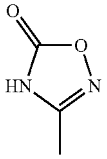

(1-3)

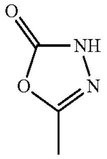

[5]

The compound or salt thereof according to any one of [1] to [4], in which $R^3$, $R^5$, $R^6$, and $R^7$ are the same as or different from each other and are a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A, Substituent Group A:

a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent group B; and a heterocyclic group which may be substituted with one or more substituents selected from Substituent group B, Substituent Group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

[6]

The compound or salt thereof according to any one of [1] to [5], in which $R^3$ is a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

[7]

The compound or salt thereof according to any one of [1] to [6], in which $R^5$, $R^6$, and $R^7$ are the same as or different from each other and each are a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A.

[8]

The compound or salt thereof according to any one of [1] to [7], in which $R^4$ is an aryl group which may be substituted with one or more substituents selected from Substituent group A, a monocyclic nitrogen-containing heterocyclic group which may be substituted with one or more substituents selected from Substituent group A, a monocyclic oxygen-containing heterocyclic group which may be substituted with one or more substituents selected from Substituent group A, a bicyclic nitrogen-containing heterocyclic group which may be substituted with one or more substituents selected from Substituent group A, or a bicyclic oxygen-containing heterocyclic group which may be substituted with one or more substituents selected from Substituent group A.

[9]

The compound or salt thereof according to [8], in which $R^4$ is a phenyl group which may be substituted with one or more substituents selected from Substituent group A, a pyridyl group which may be substituted with one or more substituents selected from Substituent group A, a tetrahydropyranyl group which may be substituted with one or more substituents selected from Substituent group A, or a dihydropyranyl group which may be substituted with one or more substituents selected from Substituent group A.

[10]

The compound or salt thereof according to any one of [1] to [9], in which $R^8$ is a hydrogen atom, a hydroxyl group which may be protected, an amino group which may be protected, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a general formula of $SO_2R^9$.

[11]

The compound or salt thereof according to any one of [1] to [10], in which $R^9$ is an amino group which may be protected, a $C_{1-6}$ alkyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, or a di($C_{1-6}$ alkyl)amino group which may be substituted with one or more substituents selected from Substituent group A.

[12]

A pharmaceutical composition including the compound or salt thereof according to any one of [1] to [11].

[13]

An anti-tumor agent including the compound or salt thereof according to any one of [1] to [11].

[14]

A dihydroorotate dehydrogenase inhibitor including the compound or salt thereof according to any one of [1] to [11].

[15]

A compound selected from Compound group X or a salt thereof, which is an intermediate for producing the compound or salt thereof according to [1]:

Compound Group X:

6-cyclopropyl-3-((3-(2,6-dimethylpyridin-3-yl)-2-(2,2,2-trifluoroethoxy)phenyl)amino)pyrazine-2-carboxylic acid, 3-((4'-cyano-2'-methyl-2-(2,2,2-trifluoroethoxy)-[1,1'-biphenyl]-3-yl)amino)-6-cyclopropylpyrazine-2-carboxylic acid, (S)-5-cyclopropyl-2-((2-(3,6-dihydro-2H-pyran-4-yl)-3-((1,1,1-trifluoropropan-2-yl)oxy)pyridin-4-yl)amino)benzoic acid, 5-cyclopropyl-2-((5-(3,6-dihydro-2H-pyran-4-yl)-4-(2,2,2-trifluoroethoxy)pyridin-3-yl)amino)benzoic acid, 5-cyclopropyl-2-((3-(tetrahydro-2H-pyran-4-yl)-2-(2,2,2-trifluoroethoxy)phenyl)amino)nicotinic acid, 5-cyclopropyl-2-((2-(difluoromethoxy)-5-fluoro-3-(tetrahydro-2H-pyran-4-yl)phenyl)amino)nicotinic acid, 3-((4'-cyano-2-(2,2,2-trifluoroethoxy)-[1,1'-biphenyl]-3-yl)amino)-6-cyclopropylpyrazine-2-carboxylic acid, 5-cyclopropyl-2-((3-(3,6-dihydro-2H-pyran-4-yl)-2-(2,2,2-trifluoroethoxy)phenyl)amino)nicotinic acid, (S)-5-cyclopropyl-2-((5-(3,6-dihydro-2H-pyran-4-yl)-4-((1,1,1-trifluoropropan-2-yl)oxy)pyridin-3-yl)amino)benzoic acid, 2-((4'-cyano-2-(2,2,2-trifluoroethoxy)-[1,1'-biphenyl]-3-yl)amino)-5-cyclopropylnicotinic acid, 5-cyclopropyl-2-((5-fluoro-3-(tetrahydro-2H-pyran-4-yl)-2-(2,2,2-trifluoroethoxy)phenyl)amino)nicotinic acid, 3-((3'-cyano-2-(2,2,2-trifluoroethoxy)-[1,1'-biphenyl]-3-yl)amino)-6-cyclopropylpyrazine-2-carboxylic acid, 5-cyclopropyl-2-((2-ethyl-3-(tetrahydro-2H-pyran-4-yl)phenyl)amino)nicotinic acid, 3-((4'-cyano-2-(difluoromethoxy)-[1,1'-biphenyl]-3-yl)amino)-6-cyclopropylpyrazine-2-carboxylic acid, 3-((4'-cyano-2-(difluoromethoxy)-5-fluoro-[1,1'-biphenyl]-3-yl)amino)-6-cyclopropylpyrazine-2-carboxylic acid, 6-cyclopropyl-3-((4'-fluoro-2-(2,2,2-trifluoroethoxy)-[1,1'-biphenyl]-3-yl)amino)pyrazine-2-carboxylic acid, 5-cyclopropyl-2-((3-(3,6-dihydro-2H-pyran-4-yl)-2-ethoxy-6-fluorophenyl)amino)nicotinic acid, 5-cyclopropyl-2-((3-(3,6-dihydro-2H-pyran-4-yl)-2-ethoxy-4-fluorophenyl)amino)nicotinic acid, 2-cyclopropyl-5-((3-(3,6-dihydro-2H-pyran-4-yl)-2-(2,2,2-trifluoroethoxy)phenyl)amino)isonicotinic acid, and (S)-6-cyclopropyl-3-((3-(tetrahydro-2H-pyran-4-yl)-2-((1,1,1-trifluoropropan-2-yl)oxy)phenyl)amino)pyrazine-4-carboxylic acid.

[A] A method for treating a tumor, including administering the compound or salt thereof according to any one of [1] to [11] to a subject.

[B] A method for inhibiting dihydroorotate dehydrogenase, including administering the compound or salt thereof according to any one of [1] to [11] to a subject.

[C] The compound or salt thereof according to any one of (1) to (11), for use in the treatment of a tumor.

[D] The compound or salt thereof according to any one of [1] to [11], for use in the treatment for inhibiting dihydroorotate dehydrogenase.

[E] Use of the compound or salt thereof according to any one of (1) to (11) for the production of a pharmaceutical composition.

[F] Use of the compound or salt thereof according to any one of (1) to (11) for the production of an anti-tumor agent.

[G] Use of the compound or salt thereof according to any one of [1] to [11] for the production of a dihydroorotate dehydrogenase inhibitor.

The compound or salt thereof according to an aspect of the present invention has an excellent DHODH inhibitory effect and is useful as a DHODH inhibitor.

In addition, the compound or salt thereof according to the aspect of the present invention has an excellent anti-tumor activity and is useful as a pharmaceutical composition such as an anti-tumor agent. The compound or salt thereof according to the aspect of the present invention is useful for the treatment such as prevention or treatment of blood cancers.

In addition, the compound selected from Compound group X or a salt thereof is useful as an intermediate for producing the compound or salt thereof according to the aspect of the present invention.

DESCRIPTION OF THE PREFERRED EMBODIMENTS

Hereinafter, the present invention will be described in detail.

As used in the present invention, "%" means percentage by mass unless otherwise specified. In the present invention, any numerical range indicated using a term "to" indicates a range including numerical values described before and after the "to" as a minimum value and a maximum value, respectively. Further, in the present invention, in a case where a plurality of substances corresponding to components are present in a composition, the amount of each component in the composition means a total amount of the plurality of substances present in the composition, unless otherwise specified.

In the present invention, the individual terms have the following meanings, unless otherwise specified.

The halogen atom refers to a fluorine atom, a chlorine atom, a bromine atom, or an iodine atom.

The $C_{1-6}$ alkyl group refers to a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, or a hexyl group.

The $C_{1-6}$ alkyl sulfonyl group refers to a $C_{1-6}$ alkylsulfonyl group such as a methylsulfonyl group, an ethylsulfonyl group, or a propylsulfonyl group.

The $C_{1-6}$ alkylsulfonyloxy group refers to a $C_{1-6}$ alkylsulfonyloxy group such as a methylsulfonyloxy group or an ethylsulfonyloxy group.

The $C_{2-6}$ alkenyl group refers to a linear or branched $C_{2-6}$ alkenyl group such as a vinyl group, an allyl group, a propenyl group, an isopropenyl group, a butenyl group, an isobutenyl group, a 1,3-butadienyl group, a pentenyl group, or a hexenyl group.

The $C_{2-6}$ alkynyl group refers to a linear or branched $C_{2-6}$ alkynyl group such as an ethynyl group, a propynyl group, a butynyl group, a pentynyl group, or a hexynyl group.

The $C_{3-8}$ cycloalkyl group refers to a $C_{3-8}$ cycloalkyl group such as a cyclopropyl group, a cyclobutyl group, a cyclopentyl group, a cyclohexyl group, or a cycloheptyl group.

The $C_{1-6}$ alkylamino group refers to a linear or branched $C_{1-6}$ alkylamino group such as a methylamino group, an ethylamino group, a propylamino group, an isopropylamino group, a butylamino group, a sec-butylamino group, a tert-butylamino group, a pentylamino group, or a hexylamino group.

The di($C_{1-6}$ alkyl)amino group refers to a linear or branched di($C_{1-6}$ alkyl)amino group such as a dimethylamino, a diethylamino group, a dipropylamino group, a diisopropylamino group, a dibutylamino group, a di(tert-butyl)amino group, a dipentylamino group, a dihexylamino group, an (ethyl)(methyl)amino group, or a (methyl)(propyl) amino group.

The $C_{1-6}$ alkoxy group refers to a linear or branched $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group, or a hexyloxy group.

The $C_{1-6}$ alkoxy $C_{1-6}$ alkyl group refers to a $C_{1-6}$ alkyloxy $C_{1-6}$ alkyl group such as a methoxymethyl group or a 1-ethoxyethyl group.

The $C_{1-6}$ alkoxycarbonyl group refers to a linear or branched $C_{1-6}$ alkyloxycarbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, or a hexyloxycarbonyl group.

The $C_{3-8}$ cycloalkoxy group refers to a $C_{3-8}$ cycloalkyloxy group such as a cyclopropoxy group, a cyclobutoxy group, a cyclopentyloxy group, a cyclohexyloxy group, or a cycloheptyloxy group.

The aryl group refers to a phenyl group, a naphthyl group, or the like.

The aryloxy group refers to a phenoxy group, a naphthalen-1-yloxy group, a naphthalen-2-yloxy group, or the like.

The arylsulfonyl group refers to a benzenesulfonyl group, a p-toluenesulfonyl group, a naphthalenesulfonyl group, or the like.

The arylsulfonyloxy group refers to a benzenesulfonyloxy group, a p-toluenesulfonyloxy group, or the like.

The aryl $C_{1-6}$ alkyl group refers to an aryl $C_{1-6}$ alkyl group such as a benzyl group, a diphenylmethyl group, a trityl group, a phenethyl group, a 2-phenylpropyl group, a 3-phenylpropyl group, or a naphthylmethyl group.

The aryl $C_{1-6}$ alkoxy group refers to an aryl $C_{1-6}$ alkyloxy group such as a benzyloxy group, a diphenylmethoxy group, a trityloxy group, a phenethyloxy group, a 2-phenylpropoxy group, a 3-phenylpropoxy group, or a naphthylmethoxy group.

The aryl $C_{1-6}$ alkoxy $C_{1-6}$ alkyl group refers to an aryl $C_{1-6}$ alkyloxy $C_{1-6}$ alkyl group such as a benzyloxymethyl group or a phenethyloxymethyl group.

The aryl $C_{1-6}$ alkoxycarbonyl group refers to an aryl $C_{1-6}$ alkyloxycarbonyl group such as a benzyloxycarbonyl group or a phenethyloxycarbonyl group.

The aryloxycarbonyl group refers to a phenoxycarbonyl group, a naphthalen yloxycarbonyl group, or a naphthalen-2-yloxycarbonyl group.

The heterocyclic group refers to a monocyclic heterocyclic group, a bicyclic heterocyclic group, a spiro heterocyclic group, or a cross-linked heterocyclic group.

The monocyclic heterocyclic group refers to a monocyclic nitrogen-containing heterocyclic group, a monocyclic oxygen-containing heterocyclic group, a monocyclic sulfur-containing heterocyclic group, a monocyclic nitrogen- and oxygen-containing heterocyclic group, or a monocyclic nitrogen- and sulfur-containing heterocyclic group.

The monocyclic nitrogen-containing heterocyclic group refers to a monocyclic nitrogen-containing heterocyclic group which contains only a nitrogen atom as a heteroatom forming the ring, such as an aziridinyl group, an azetidinyl group, a pyrrolidinyl group, a pyrrolinyl group, a pyrrolyl group, a piperidyl group, a tetrahydropyridyl group, a dihydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group, or a tetrazolyl group.

The monocyclic oxygen-containing heterocyclic group refers to a monocyclic oxygen-containing heterocyclic group which contains only an oxygen atom as a heteroatom forming the ring, such as an oxetanyl group, a tetrahydrofuranyl group, a furanyl group, a tetrahydropyranyl group, a dihydropyranyl group, a pyranyl group, a 1,3-dioxanyl group, or a 1,4-dioxanyl group.

The monocyclic sulfur-containing heterocyclic group refers to a thienyl group.

The monocyclic nitrogen- and oxygen-containing heterocyclic group refers to a monocyclic nitrogen- and oxygen-containing heterocyclic group which contains only a nitrogen atom and an oxygen atom as heteroatoms forming the ring, such as an oxazolyl group, an isoxazolyl group, an oxadiazolyl group, a morpholinyl group, or an oxazepanyl group.

The monocyclic nitrogen- and sulfur-containing heterocyclic group refers to a monocyclic nitrogen- and sulfur-containing heterocyclic group which contains only a nitrogen atom and a sulfur atom as heteroatoms forming the ring, such as a thiazolyl group, an isothiazolyl group, a thiadiazolyl group, a thiomorpholinyl group, a 1-oxidothiomorpholinyl group, or a 1,1-dioxidothiomorpholinyl group.

The bicyclic heterocyclic group refers to a bicyclic nitrogen-containing heterocyclic group, a bicyclic oxygen-containing heterocyclic group, a bicyclic sulfur-containing heterocyclic group, a bicyclic nitrogen- and oxygen-containing heterocyclic group, or a bicyclic nitrogen- and sulfur-containing heterocyclic group.

The bicyclic nitrogen-containing heterocyclic group refers to a bicyclic nitrogen-containing heterocyclic group which contains only a nitrogen atom as a heteroatom forming the ring, such as an indolinyl group, an indolyl group, an isoindolinyl group, an isoindolyl group, a benzimidazolyl group, an indazolyl group, a benzotriazolyl group, a pyrazolopyridinyl group, a quinolyl group, a tetrahydroquinolinyl group, a tetrahydroisoquinolinyl group, an isoquinolinyl group, a quinolizinyl group, a cinnolinyl group, a phthalazinyl group, a quinazolinyl group, a dihydroquinoxalinyl group, a quinoxalinyl group, a naphthyridinyl group, a purinyl group, a pteridinyl group, or a quinuclidinyl group.

The bicyclic oxygen-containing heterocyclic group refers to a bicyclic oxygen-containing heterocyclic group which contains only an oxygen atom as a heteroatom forming the ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, or a 1,4-benzodioxanyl group.

The bicyclic sulfur-containing heterocyclic group refers to a bicyclic sulfur-containing heterocyclic group which contains only a sulfur atom as a heteroatom forming the ring, such as a 2,3-dihydrobenzothienyl group or a benzothienyl group.

The bicyclic nitrogen- and oxygen-containing heterocyclic group refers to a bicyclic nitrogen- and oxygen-containing heterocyclic group which contains only a nitrogen atom and an oxygen atom as heteroatoms forming the ring, such as a benzoxazolyl group, a benzisoxazolyl group, a benzoxadiazolyl group, a benzomorpholinyl group, a dihydropyranopyridyl group, a dioxolopyridyl group, a furopyridinyl group, a dihydrodioxynopyridyl group, or a dihydropyridooxazinyl group.

The bicyclic nitrogen- and sulfur-containing heterocyclic group refers to a bicyclic nitrogen- and sulfur-containing heterocyclic group which contains a nitrogen atom and a sulfur atom as heteroatoms forming the ring, such as a benzothiazolyl group, a benzoisothiazolyl group, or a benzothiadiazolyl group.

The spiro heterocyclic group refers to a spiro heterocyclic group which contains a nitrogen atom, an oxygen atom, or a sulfur atom as a heteroatom forming the ring, such as a 2-oxa-6-azaspiro[3.3]heptyl group, a 1,4-dioxaspiro[4.5]decyl group, a 1-oxa-8-azaspiro[4.5]decyl group, or a 1-thia-8-azaspiro[4.5]decyl group.

The bridged heterocyclic group refers to a bridged heterocyclic group which contains a nitrogen atom, an oxygen atom, or a sulfur atom as a heteroatom forming the ring, such as a 3-oxa-8-azabicyclo[3.2.1]octyl group, an 8-oxa-3-azabicyclo[3.2.1]octyl group, or a quinuclidinyl group.

The acyl group refers to a formyl group, a succinyl group, a glutaryl group, a maleoyl group, a phthaloyl group, a $C_{2-6}$ alkanoyl group, a $C_{3-8}$ cycloalkylcarbonyl group, an aroyl group, or a heterocyclic carbonyl group.

The $C_{2-6}$ alkanoyl group refers to a linear or branched $C_{2-6}$ alkanoyl group such as an acetyl group, a propionyl group, a valeryl group, an isovaleryl group, or a pivaloyl group.

The $C_{3-8}$ cycloalkylcarbonyl group refers to a $C_{3-8}$ cycloalkylcarbonyl group such as a cyclopropylcarbonyl group, a cyclobutylcarbonyl group, a cyclopentylcarbonyl group, a cyclohexylcarbonyl group, or a cycloheptylcarbonyl group.

The aroyl group refers to a benzoyl group, a naphthoyl group, or the like.

The heterocyclic carbonyl group refers to a heterocyclic carbonyl group such as a pyrrolylcarbonyl group, a pyridylcarbonyl group, a furanylcarbonyl group, or a thienylcarbonyl group.

The silyl group refers to a trimethylsilyl group, a triethylsilyl group, a tributylsilyl group, or a tert-butyldimethylsilyl group.

The leaving group refers to a halogen atom, a $C_{1-6}$ alkylsulfonyloxy group, an aryloxy group, or an arylsulfonyloxy group. The $C_{1-6}$alkylsulfonyloxy group, aryloxy group, and arylsulfonyloxy group may be substituted with one or more substituents selected from a halogen atom, a nitro group, a $C_{1-6}$ alkyl group, and a $C_{1-6}$ alkoxy group.

The hydroxyl protective group is any conventional group that can be used as a protective group for a hydroxyl group, and examples thereof include the groups described in, for example, T. W. Greene et al., Protective Groups in Organic Synthesis, 4th edition, pp. 16 to 299, 2007, John Wiley & Sons, Inc. Specific examples of the hydroxyl protective group include a $C_{1-6}$ alkyl group, a $C_{2-6}$ alkenyl group, an aryl $C_{1-6}$ alkyl group, a $C_{1-6}$ alkoxy $C_{1-6}$ alkyl group, an aryl $C_{1-6}$ alkoxy $C_{1-6}$ alkyl group, an acyl group, a $C_{1-6}$ alkoxycarbonyl group, an aryl $C_{1-6}$ alkoxycarbonyl group, a $C_{1-6}$ alkylsulfonyl group, an arylsulfonyl group, a silyl group, a tetrahydrofuranyl group, and a tetrahydropyranyl group.

The amino protective group is any conventional group that can be used as a protective group for an amino group, and examples thereof include the groups described in, for example, T. W. Greene et al., Protective Groups in Organic Synthesis, 4th edition, pp. 696 to 926, 2007, John Wiley & Sons, Inc. Specific examples of the amino protective group include an aryl $C_{1-6}$ alkyl group, a $C_{1-6}$alkoxy $C_{1-6}$alkyl group, an acyl group, a $C_{1-6}$ alkoxycarbonyl group, an aryl $C_{1-6}$ alkoxycarbonyl group, an aryloxycarbonyl group, a $C_{1-6}$ alkylsulfonyl group, an arylsulfonyl group, and a silyl group.

Aliphatic hydrocarbons refer to pentane, hexane, heptane, cyclohexane, methylcyclohexane, and ethylcyclohexane.

Halogenated hydrocarbons refer to dichloromethane, chloroform, and dichloroethane. Examples of alcohols include methanol, ethanol, propanol, 2-propanol, butanol, and 2-methyl-2-propanol.

Examples of glycols include ethylene glycol, propylene glycol, and diethylene glycol. Ethers refer to diethyl ether, diisopropyl ether, dioxane, tetrahydrofuran, anisole, ethylene glycol dimethyl ether, diethylene glycol dimethyl ether, and diethylene glycol diethyl ether.

Ketones refer to acetone, 2-butanone, 4-methyl-2-pentanone, and methyl isobutyl ketone.

Esters refer to methyl acetate, ethyl acetate, propyl acetate, and butyl acetate.

Amides refer to N,N-dimethylformamide, N,N-dimethylacetamide, and N-methyl pyrrolidone.

Nitriles refer to acetonitrile and propionitrile.

Sulfoxides refer to dimethyl sulfoxide and sulfolane.

Aromatic hydrocarbons refer to benzene, toluene, and xylene.

The inorganic base refers to sodium hydroxide, potassium hydroxide, sodium methoxide, sodium ethoxide, tert-butoxy sodium, tert-butoxy potassium, sodium hydrogen carbonate, sodium carbonate, potassium carbonate, tripotassium phosphate, potassium acetate, cesium fluoride, cesium carbonate, or tert-butyl magnesium chloride.

The organic base refers to tri ethyl amine, N,N-diisopropylethylamine, 1,8-diazabicyclo(5.4.0)undec-7-ene (DBU), pyridine, 4-dimethyl aminopyridine, N-methylmorpholine, or imidazole.

Each substituent group has the following meaning.

<Substituent Group A> a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent group B; and a heterocyclic group which may be substituted with one or more substituents selected from Substituent group B.

<Substituent Group B> a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

Examples of salts of the compound represented by General Formula (1) according to the embodiment of the present invention include salts in basic groups such as an amino group, and salts in acidic groups such as a hydroxyl group and a carboxyl group, which are commonly known.

Examples of salts in basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Examples of the salt of an acidic group include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Among the salts mentioned above, preferred salts include pharmacologically acceptable salts.

The compound represented by General Formula (1) includes, for example, a compound represented by General Formula (1a), a compound represented by General Formula (1b), and a compound represented by General Formula (1c).

(1a)

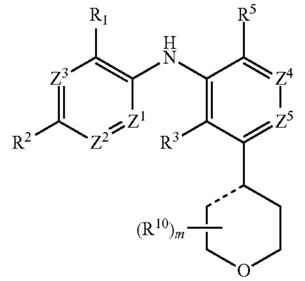

(1b)

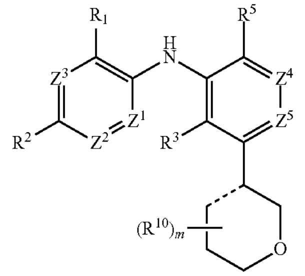

-continued (1c)

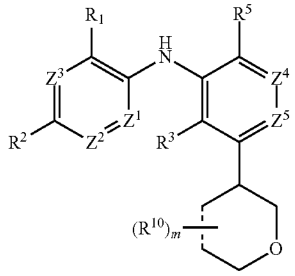

(In the formulae, $R^{10}$ represents Substituent group A; m represents an integer of 0 to 6; a broken line represents a single bond or a double bond; and $Z^1$, $Z^2$, $Z^3$, $Z^4$, $Z^5$, $R^1$, $R^2$, $R^3$, and $R^5$ are as defined above.)

Among the compound represented by General Formula (1a), the compound represented by General Formula (1b), and the compound represented by General Formula (1c), the compound represented by General Formula (1a) or the compound represented by General Formula (1b) is preferable, and the compound represented by General Formula (1a) is more preferable.

$Z^1$ $Z^1$ is a nitrogen atom or CH.

$Z^1$ is preferably a nitrogen atom.

$Z^2$ $Z^2$ is a nitrogen atom or CH.

$Z^2$ is preferably CH.

$Z^3$ $Z^3$ is a nitrogen atom or CH.

$Z^3$ is preferably a nitrogen atom or CH and more preferably a nitrogen atom.

$Z^4$ $Z^4$ is a nitrogen atom or a general formula of $CR^6$.

$Z^4$ is preferably a general formula of $CR^6$.

$Z^5$ $Z^5$ is a nitrogen atom or a general formula of $CR^7$.

$Z^5$ is preferably a general formula of $CR^7$.

The compound in which $Z^1$ is a nitrogen atom, $Z^2$ is CH, $Z^3$ is a nitrogen atom or CH, $Z^4$ is a general formula of $CR^6$, and $Z^5$ is a general formula of $CR^7$ is preferable.

The compound in which $Z^1$ is a nitrogen atom, $Z^2$ is CH, $Z^3$ is a nitrogen atom, $Z^4$ is a general formula of $CR^6$, and $Z^5$ is a general formula of $CR^7$ is more preferable.

$R^1$ $R^1$ is a general formula of $CONHR^8$, a general formula of $CH_2NHR^8$, $CH_2OH$, $CH(OH)CH_3$, $C(O)CH_3$, CHO, Formula (1-1), Formula (1-2), or Formula (1-3).

$R^1$ is preferably a general formula of $CONHR^8$, Formula (1-1), Formula (1-2), or Formula (1-3), and more preferably a general formula of $CONHR^8$.

$R^2$ $R^2$ is a $C_{1-6}$ alkyl group which may be substituted or a $C_{3-8}$ cycloalkyl group which may be substituted.

$R^2$ is preferably a $C_{1-6}$ alkyl group which may be substituted with one or more substituents selected from Substituent group A, or a $C_{3-8}$ cycloalkyl group which may be substituted with one or more substituents selected from Substituent group A.

$R^2$ is more preferably a $C_{1-6}$ alkyl group or a $C_{3-8}$ cycloalkyl group, still more preferably a $C_{3-8}$ cycloalkyl group, and most preferably a cyclopropyl group.

$R^3$ $R^3$ is a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted.

$R^3$ is preferably a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^3$ is more preferably a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^3$ is still more preferably a halogen atom, a $C_{1-6}$ alkyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, or a $C_{1-6}$ alkoxy $C_{1-6}$ alkyl group which may be substituted with one or more substituents selected from Substituent group A.

$R^3$ is even still more preferably a $C_{1-6}$ alkyl group which may be substituted with one or more substituents selected from Substituent group A, or a $C_{1-6}$ alkoxy group which may be substituted with one or more substituents selected from Substituent group A.

$R^4$ $R^4$ is an aryl group which may be substituted or a heterocyclic group which may be substituted.

$R^4$ is preferably an aryl group which may be substituted with one or more substituents selected from Substituent group A, or a heterocyclic group which may be substituted with one or more substituents selected from Substituent group A.

$R^4$ is more preferably an aryl group which may be substituted with one or more substituents selected from Substituent group A, a monocyclic nitrogen-containing heterocyclic group which may be substituted with one or more substituents selected from Substituent group A, a monocyclic oxygen-containing heterocyclic group which may be substituted with one or more substituents selected from Substituent group A, a bicyclic nitrogen-containing heterocyclic group which may be substituted with one or more substituents selected from Substituent group A, or a bicyclic oxygen-containing heterocyclic group which may be substituted with one or more substituents selected from Substituent group A.

$R^4$ is still more preferably an aryl group which may be substituted with one or more substituents selected from Substituent group A, a monocyclic nitrogen-containing heterocyclic group which may be substituted with one or more substituents selected from Substituent group A, or a monocyclic oxygen-containing heterocyclic group which may be substituted with one or more substituents selected from Substituent group A.

$R^4$ is even still more preferably a phenyl group which may be substituted with one or more substituents selected from Substituent group A, a pyridyl group which may be substituted with one or more substituents selected from Substituent group A, a tetrahydropyranyl group which may be substituted with one or more substituents selected from Substituent group A, or a dihydropyranyl group which may be substituted with one or more substituents selected from Substituent group A.

$R^5$ $R^5$ is a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted.

$R^5$ is preferably a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^5$ is more preferably a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A.

$R^5$ is still more preferably a hydrogen atom, a halogen atom, or a $C_{1-6}$ alkoxy group.

$R^6$ $R^6$ is a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted.

$R^6$ is preferably a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^6$ is more preferably a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A.

$R^6$ is still more preferably a hydrogen atom, a halogen atom, or a $C_{1-6}$ alkoxy group.

$R^7$ $R^7$ is a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted.

$R^7$ is preferably a hydrogen atom, a halogen atom, a hydroxyl group which may be protected, an amino group which may be protected, a $C_{1-6}$ alkyl group which may be substituted with one or more substituents selected from Substituent group A, a $C_{2-6}$ alkenyl group which may be substituted with one or more substituents selected from Substituent group A, a $C_{2-6}$ alkynyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a $C_{1-6}$ alkoxy $C_{1-6}$ alkyl group which may be substituted with one or more substituents selected from Substituent group A.

$R^7$ is more preferably a hydrogen atom, a halogen atom, a $C_{1-6}$ alkyl group which may be substituted with one or more substituents selected from Substituent group A, or a $C_{1-6}$ alkoxy group which may be substituted with one or more substituents selected from Substituent group A.

$R^7$ is still more preferably a hydrogen atom, a halogen atom, or a $C_{1-6}$ alkoxy group.

$R^8$ $R^8$ is a hydrogen atom, a hydroxyl group which may be protected, an amino group which may be protected, a $C_{1-6}$ alkyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a general formula of $SO_2R^9$.

$R^8$ is preferably a hydrogen atom, a hydroxyl group which may be protected, an amino group which may be protected, a $C_{1-6}$ alkyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a general formula of $SO_2R^9$.

$R^8$ is more preferably a hydrogen atom, a hydroxyl group which may be protected, an amino group which may be protected, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, a di($C_{1-6}$ alkyl)amino group which may be substituted with one or more substituents selected from Substituent group A, or a general formula of $SO_2R^9$.

$R^9$ $R^9$ is a hydroxyl group which may be protected, an amino group which may be protected, a $C_{1-6}$ alkyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$alkylamino group which may be substituted, or a di($C_{1-6}$ alkyl)amino group which may be substituted.

$R^9$ is preferably a hydroxyl group which may be protected, an amino group which may be protected, a $C_{1-6}$alkyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, or a di($C_{1-6}$ alkyl)amino group which may be substituted with one or more substituents selected from Substituent group A.

$R^9$ is more preferably an amino group which may be protected, a $C_{1-6}$ alkyl group which may be substituted with one or more substituents selected from Substituent group A, a $C_{3-8}$ cycloalkyl group which may be substituted with one or more substituents selected from Substituent group A, a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylamino group which may be substituted with one or more substituents selected from Substituent group A, or a di($C_{1-6}$ alkyl)amino group which may be substituted with one or more substituents selected from Substituent group A.

m m is an integer of 0 to 6.

m is preferably an integer of 0 to 4 and more preferably an integer of 0 to 2.

Broken Line

The broken line is a single bond or a double bond.

Both a single bond and a double bond are preferable as the broken line.

A halogen atom; a cyano group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; an aryl group which may be substituted with one or more substituents selected from Substituent group B; and a heterocyclic group which may be substituted with one or more substituents selected from Substituent group B are preferable as Substituent group A in $R^2$, $R^3$, $R^4$, $R^5$, $R^6$, and $R^7$.

A halogen atom; a cyano group; a $C_{1-6}$ alkyl group; and a $C_{1-6}$ alkoxy group are more preferable as Substituent group A.

A halogen atom; a $C_{1-6}$alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; and a $C_{1-6}$ alkoxy $C_{1-6}$ alkyl group are preferable as Substituent group B in $R^2$, $R^3$, $R^4$, $R^5$, $R^6$, and $R^7$.

A halogen atom; a $C_{1-6}$alkyl group; a $C_{1-6}$alkoxy group; and a $C_{1-6}$ alkoxy $C_{1-6}$ alkyl group are more preferable as Substituent group B.

In a case where isomers (for example, an optical isomer, a geometric isomer, and a tautomer) are present for the compound represented by General Formula (1), General Formula (1a), General Formula (1b), or General Formula (1c), these isomers can also be used. In addition, in a case where solvates, hydrates, and various forms of crystals are present, these solvates, hydrates, and various forms of crystals can also be used.

Next, a method for producing the compound according to the embodiment of the present invention will be described.

The compound according to the embodiment of the present invention is produced by combining methods known per se, and can be produced, for example, according to the following production methods.

[Production Method 1]

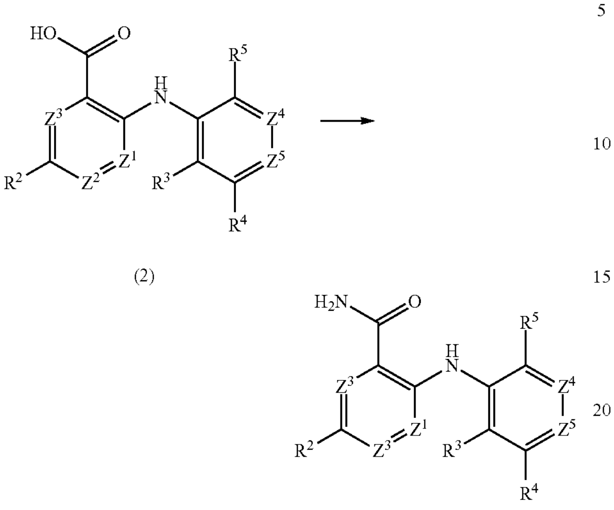

(2)

(1d)

(In the formulae, $Z^1$, $Z^2$, $Z^3$, $Z^4$, $Z^5$, $R^2$, $R^3$, $R^4$, and $R^5$ are as defined above.)

The compound represented by General Formula (2) can be produced by subjecting a compound represented by General Formula (6) which will be described later to a reaction known per se, such as hydrolysis.

The compound represented by General Formula (2) is a compound useful as an intermediate for producing the compound represented by General Formula (1).

The compound represented by General Formula (2) is preferably a compound selected from Compound group X. According to the present invention, there is provided a compound selected from Compound group X or a salt thereof, which is an intermediate for producing the compound represented by General Formula (1) or a salt thereof.

<Compound Group X>

6-cyclopropyl-3-((3-(2,6-dimethylpyridin-3-yl)-2-(2,2,2-trifluoroethoxy)phenyl)amino)pyrazine-2-carboxylic acid (Example 1-4), 3-((4'-cyano-2'-methyl-2-(2,2,2-trifluoroethoxy)-[1,1'-biphenyl]-3-yl)amino)-6-cyclopropylpyrazine-2-carboxylic acid (Example 1-5), (S)-5-cyclopropyl-2-((2-(3,6-dihydro-2H-pyran-4-yl)-3-((1,1,1-trifluoropropan-2-yl)oxy)pyridin-4-yl)amino)benzoic acid (Example 1-18), 5-cyclopropyl-2-((5-(3,6-dihydro-2H-pyran-4-yl)-4-(2,2,2-trifluoroethoxy)pyridin-3-yl)amino)benzoic acid (Example 2-1), 5-cyclopropyl-2-((3-(tetrahydro-2H-pyran-4-yl)-2-(2,2,2-trifluoroethoxy)phenyl)amino)nicotinic acid (Example 2-2), 5-cyclopropyl-2-((2-(difluoromethoxy)-5-fluoro-3-(tetrahydro-2H-pyran-4-yl)phenyl)amino)nicotinic acid (Example 2-3), 3-((4'-cyano-2-(2,2,2-trifluoroethoxy)-[1,1'-biphenyl]-3-yl)amino)-6-cyclopropylpyrazine-2-carboxylic acid (Example 2-4), 5-cyclopropyl-2-((3-(3,6-dihydro-2H-pyran-4-yl)-2-(2,2,2-trifluoroethoxy)phenyl)amino)nicotinic acid (Example 2-5), (S)-5-cyclopropyl-2-((5-(3,6-dihydro-2H-pyran-4-yl)-4-((1,1,1-trifluoropropan-2-yl)oxy)pyridin-3-yl)amino)benzoic acid (Example 2-6), 2-((4'-cyano-2-(2,2,2-trifluoroethoxy)-[1,1'-biphenyl]-3-yl)amino)-5-cyclopropylnicotinic acid (Example 2-7), 5-cyclopropyl-2-((5-fluoro-3-(tetrahydro-2H-pyran-4-yl)-2-(2,2,2-trifluoroethoxy)phenyl)amino)nicotinic acid (Example 2-8), 3-((3'-cyano-2-(2,2,2-trifluoroethoxy)-[1,1'-biphenyl]-3-yl)amino)-6-cyclopropylpyrazine-2-carboxylic acid (Example 2-9), 5-cyclopropyl-2-((2-ethyl-3-(tetrahydro-2H-pyran-4-yl)phenyl)amino)nicotinic acid (Example 2-10), 3-((4'-cyano-2-(difluoromethoxy)-[1,1'-biphenyl]-3-yl)amino)-6-cyclopropylpyrazine-2-carboxylic acid (Example 2-11), 3-((4'-cyano-2-(difluoromethoxy)-5-fluoro-[1,1'-biphenyl]-3-yl)amino)-6-cyclopropylpyrazine-2-carboxylic acid (Example 2-12), 6-cyclopropyl-3-((4'-fluoro-2-(2,2,2-trifluoroethoxy)-[1,1'-biphenyl]-3-yl)amino)pyrazine-2-carboxylic acid (Example 2-13), 5-cyclopropyl-2-((3-(3,6-dihydro-2H-pyran-4-yl)-2-ethoxy-6-fluorophenyl)amino)nicotinic acid (Example 2-14), 5-cyclopropyl-2-((3-(3,6-dihydro-2H-pyran-4-yl)-2-ethoxy-4-fluorophenyl)amino)nicotinic acid (Example 2-15), 2-cyclopropyl-5-((3-(3,6-dihydro-2H-pyran-4-yl)-2-(2,2,2-trifluoroethoxy)phenyl)amino)isonicotinic acid (Example 2-16), and (S)-6-cyclopropyl-3-((3-(tetrahydro-2H-pyran-4-yl)-2-((1,1,1-trifluoropropan-2-yl)oxy)phenyl)amino)pyrazine-4-carboxylic acid (Example 2-17).

The compound represented by General Formula (1d) can be produced by reacting the compound represented by General Formula (2) with ammonia or an ammonium salt in the presence of a condensing agent and in the presence or absence of a base.

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be used in mixture.

Preferred solvents include ethers and amides.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (2).

Examples of the condensing agent used in the reaction include carbodiimides such as N,N'-dicyclohexylcarbodiimide and N-ethyl-N'-(3-dimethylaminopropyl)carbodiimide; carbonyls such as 1,1'-carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium=hexafluorophosphate; and O-(7-azabenzotriazol-1-yl)-1,1,3,3-tetramethyluronium=hexafluorophosphate.

Examples of the base optionally used in the reaction include an inorganic base and an organic base.

The amount of the condensing agent and the base used is preferably 1 to 10 times molar and more preferably 1 to 5 times molar with respect to the compound represented by General Formula (2).

Examples of the ammonium salt include ammonium chloride, ammonium bromide, and ammonium acetate.

The amount of the ammonia or ammonium salt used may be 1 to 100 times molar and preferably 1 to 10 times molar with respect to the compound represented by General Formula (2).

The reaction may be carried out in the presence of a reaction accelerator.

Examples of the reaction accelerator include 1-hydroxybenzotriazole and N-hydroxysuccinimide.

The amount of the reaction accelerator used is preferably 1 to 10 times molar and more preferably 1 to 5 times molar with respect to the compound represented by General Formula (2).

The reaction may be carried out at −20° C. to 150° C., preferably 0° C. to 100° C. for 1 minute to 24 hours.

[Production Method 2]

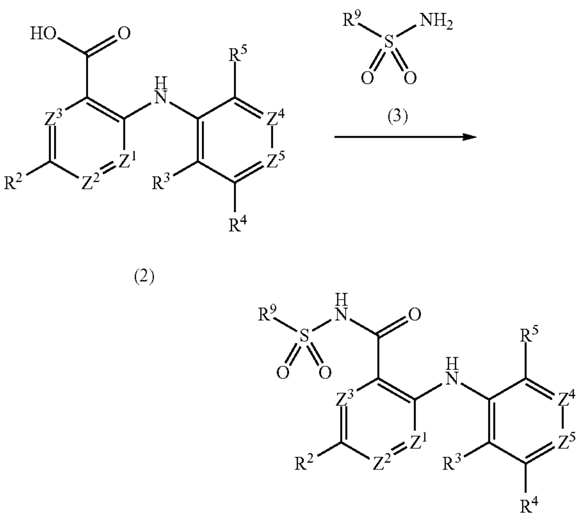

(2) (3) (1e)

(In the formulae, $Z^1$, $Z^2$, $Z^3$, $Z^4$, $Z^5$, $R^2$, $R^3$, $R^4$, $R^5$, and $R^9$ are as defined above.)

For example, methanesulfonamide is known as the compound represented by General Formula (3).

The compound represented by General Formula (1e) can be produced by reacting the compound represented by General Formula (2) with the compound represented by General Formula (3) in the presence of a condensing agent and in the presence of a base.

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be used in mixture.

Preferred solvents include ethers and amides.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (2).

Examples of the condensing agent used in the reaction include carbodiimides such as N,N'-dicyclohexylcarbodiimide and N-ethyl-N'-(3-dimethylaminopropyl)carbodiimide; carbonyls such as 1,1'-carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium=hexafluorophosphate; and O-(7-azabenzotriazol-1-yl)-1,1,3,3-tetramethyluronium=hexafluorophosphate.

Examples of the base used in the reaction include an inorganic base and an organic base.

Preferred bases include inorganic bases such as sodium hydrogen carbonate, sodium carbonate, potassium carbonate, cesium carbonate, and tripotassium phosphate, and organic bases such as pyridine, 4-(dimethylamino)pyridine, triethylamine, diisopropylethylamine, and 1,8-diazabicyclo(5,4,0)undec-7-ene.

The amount of the condensing agent and the base used is preferably 1 to 10 times molar and more preferably 1 to 5 times molar with respect to the compound represented by General Formula (2).

The reaction may be carried out at −20° C. to 150° C., preferably 0° C. to 100° C. for 1 minute to 24 hours.

[Production Method 3]

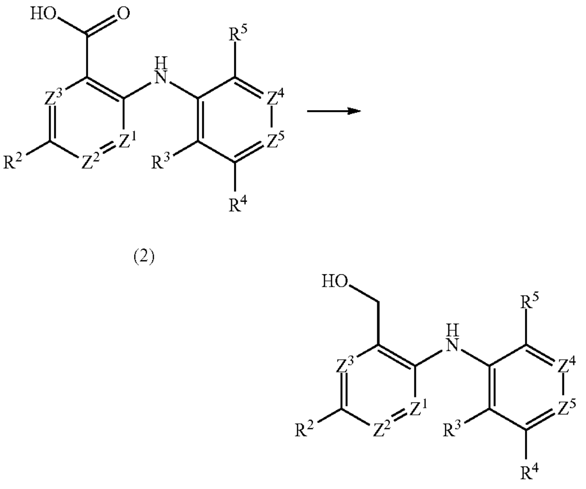

(2) (1f)

(In the formulae, $Z^1$, $Z^2$, $Z^3$, $Z^4$, $Z^5$, $R^2$, $R^3$, $R^4$, $R^5$, and $R^9$ are as defined above.)

The compound represented by General Formula (1f) can be produced by reacting the compound represented by General Formula (2) with an alkali metal borohydride in the presence of a condensing agent and in the presence or absence of a base.

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, and aromatic hydrocarbons, which may be used in mixture.

Preferred solvents include ethers and the like.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (2).

As the condensing agent and base used in the reaction, the same ones as in the production method 1 can be mentioned.

The amount of the condensing agent and the base used is preferably 1 to 10 times molar and more preferably 1 to 5 times molar with respect to the compound represented by General Formula (2).

Examples of the alkali metal borohydride used in the reaction include sodium borohydride, lithium borohydride, and potassium borohydride, among which sodium borohydride is preferable.

The amount of the alkali metal borohydride used is preferably 1 to 10 times molar and more preferably 1 to 2 times molar with respect to the compound represented by General Formula (2).

The reaction may be carried out at −20° C. to 150° C., preferably 0° C. to 100° C. for 1 minute to 24 hours.

[Production Method 4]

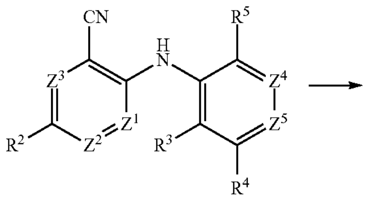

(4)

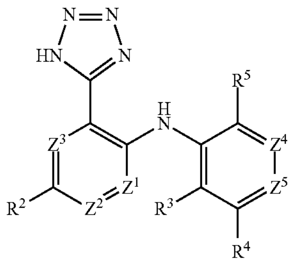

(1g)

(In the formulae, $Z^1$, $Z^2$, $Z^3$, $Z^4$, $Z^5$, $R^2$, $R^3$, $R^4$, and $R^5$ are as defined above.)

The compound represented by General Formula (1g) can be produced, for example, by the method described in Heterocyclic Compounds, New Edition, Applications, pp. 98 to 100, 2004, Kodansha Ltd., or by a method equivalent thereto. Specifically, the compound represented by General Formula (1g) can be produced by reacting the compound represented by General Formula (4) with an azide in the presence or absence of a base.

The solvent used in the reaction is not particularly limited as long as it does not adversely affect the reaction, and examples thereof include aliphatic hydrocarbons, halogenated hydrocarbons, ethers, amides, sulfoxides, and aromatic hydrocarbons, which may be used in mixture.

Preferred solvents include amides and the like.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (2).

Examples of the base optionally used in the reaction include an inorganic base and an organic base.

Examples of the azide used in the reaction include sodium azide and trimethylsilyl azide.

The amount of the azide used may be 1 to 100 times molar and preferably 1 to 10 times molar with respect to the compound represented by General Formula (4).

The reaction may be carried out at −20° C. to 150° C., preferably 0° C. to 100° C. for 1 minute to 24 hours.

[Production Method 5]

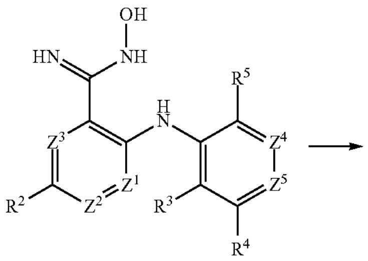

(5)

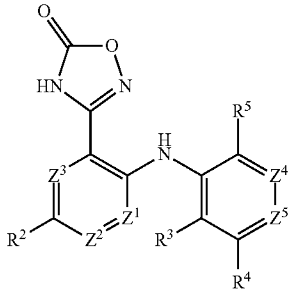

(1h)

(In the formulae, $Z^1$, $Z^2$, $Z^3$, $Z^4$, $Z^5$, $R^2$, $R^3$, $R^4$, and $R^5$ are as defined above.)

The compound represented by General Formula (1h) can be produced by reacting the compound represented by General Formula (5) with a condensing agent in the presence or absence of a base.

The solvent used in the reaction is not particularly limited as long as it does not adversely affect the reaction, and examples thereof include aliphatic hydrocarbons, halogenated hydrocarbons, ethers, ketones, esters, amides, nitriles, sulfoxides, and aromatic hydrocarbons, which may be used in mixture.

Preferred solvents include ethers and amides.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (5).

As the condensing agent and base used in the reaction, the same ones as in the production method 1 can be mentioned.

The amount of the condensing agent and the base used is preferably 1 to 10 times molar and more preferably 1 to 5 times molar with respect to the compound represented by General Formula (5).

The reaction may be carried out at −20° C. to 150° C., preferably 0° C. to 100° C. for 1 minute to 24 hours.

[Production Method 6]

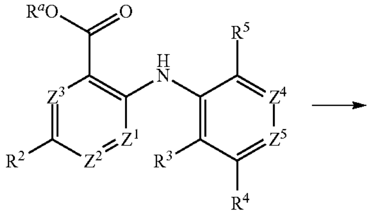

(6)

-continued

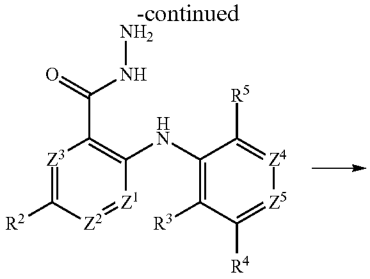

(1i)

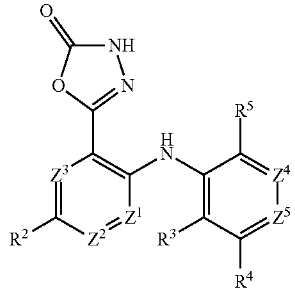

(1j)

(In the formulae, $R^a$ represents a protective group for a carboxyl group; and $Z^1$, $Z^2$, $Z^3$, $Z^4$, $Z^5$, $R^2$, $R^3$, $R^4$, and $R^5$ are as defined above.)

(6-1)

The compound represented by General Formula (1i) can be produced by reacting the compound represented by General Formula (6) with hydrazine.

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be used in mixture.

Preferred solvents include alcohols and the like.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (2).

Examples of the hydrazine used in the reaction include hydrazine monohydrate.

The amount of the hydrazine used may be 1 to 100 times molar and preferably 1 to 10 times molar with respect to the compound represented by General Formula (6).

The reaction may be carried out at −20° C. to 150° C., preferably 0° C. to 100° C. for 1 minute to 24 hours.

(6-2)

The compound represented by General Formula (1j) can be produced by reacting the compound represented by General Formula (1i) with a condensing agent in the presence or absence of a base, according to the production method 5.

[Production Method A]

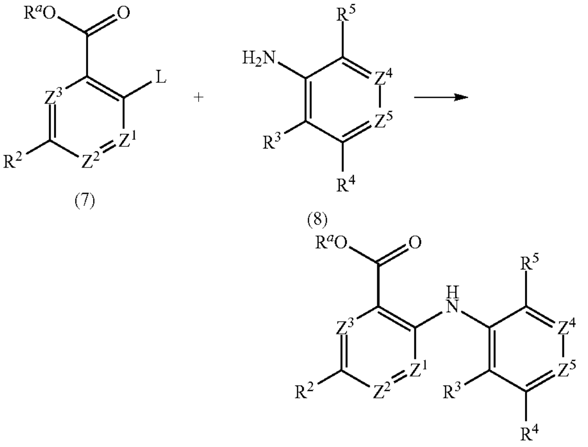

(7) (8)

(6)

(In the formulae, L represents a leaving group; and $Z^1$, $Z^2$, $Z^3$, $Z^4$, $Z^5$, $R^2$, $R^3$, $R^4$, $R^5$, and $R^a$ are as defined above.)

For example, methyl 3-bromo-6-cyclopropylpyrazine-2-carboxylate (US2011/306589A) is known as the compound represented by General Formula (7).

The compound represented by General Formula (6) can be produced by reacting the compound represented by General Formula (7) with the compound represented by General Formula (8) in the presence or absence of a base, in the presence of a palladium catalyst, and in the presence or absence of a ligand.

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be used in mixture.

Preferred solvents include ethers, esters, and aromatic hydrocarbons.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (7).

Examples of the base optionally used in the reaction include an inorganic base and an organic base.

Preferred bases include inorganic bases such as sodium hydrogen carbonate, sodium carbonate, potassium carbonate, cesium carbonate, and tripotassium phosphate, and organic bases such as pyridine, 4-(dimethylamino)pyridine, triethylamine, and diisopropylethylamine.

The amount of the base used is preferably 1 to 10 times molar, more preferably 1 to 5 times molar, and still more preferably 1 to 2 times molar with respect to the compound represented by General Formula (7).

Examples of the palladium catalyst used in the reaction include metal palladium such as palladium-carbon and palladium black; inorganic palladium salts such as palladium chloride; organic palladium salts such as palladium (II) acetate; organic palladium complexes such as tetrakis(triphenylphosphine)palladium (0), bis(triphenylphosphine)palladium (II) dichloride, 1,1'-bis(diphenylphosphino)ferrocene palladium (II) dichloride, tris(dibenzylideneacetone)dipalladium (0), and bis(di-tert)-butyl (4-dimethylaminophenyl) phosphine)palladium (II) dichloride; and polymer-immobilized organic palladium complexes such as polymer-supported bis(acetate)triphenylphosphine palladium (II) and polymer-supported di(acetate)dicyclohexylphenylphosphine palladium (II), which may be used in combination.

The amount of the palladium catalyst used is preferably 0.00001 to 1 times molar and more preferably 0.001 to 0.2 times molar with respect to the compound represented by General Formula (7).

Examples of the ligand optionally used in the reaction include trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite, and tributylphosphite; tricycloalkylphosphites such as tricyclohexylphosphite; triarylphosphite such as triphenylphosphite; imidazolium salts such as 1,3-bis(2,4,6-trimethylphenyl) imidazolium chloride; diketones such as acetylacetone and octafluoroacetylacetone; amines such as trimethylamine, triethylamine, tripropylamine, triisopropylamine, and tributylamine; 1,1'-bis(diphenylphosphino)ferrocene; 2,2'-bis(diphenylphosphino)-1,1'-binaphthyl; 2-dicyclohexylphosphino-2,6'-dimethoxybiphenyl; 2-dicyclohexylphosphino-2',4',6'-triisopropylbiphenyl; 2-(di-tert-butylphosphino)-2',4',6'-triisopropylbiphenyl; 2-dicyclohexylphosphino-2'-(N,N-dimethylamino)biphenyl; 4,5-bis(diphenylphosphino)-9,9-dimethylxanthene; and 2-(di-tert-butylphosphino)biphenyl, which may be used in combination.

The amount of the ligand used is 0.00001 to 1 times molar and preferably 0.02 to 0.5 times molar with respect to the compound represented by General Formula (7).

The amount of the compound represented by General Formula (8) used is preferably 1 to 50 times molar and more preferably 1 to 2 times molar with respect to the compound represented by General Formula (7).

The reaction may be carried out preferably at 40° C. to 170° C. for 1 minute to 24 hours under an atmosphere of an inert gas (for example, nitrogen or argon).

The reaction may be carried out under microwave irradiation.

[Production Method B]

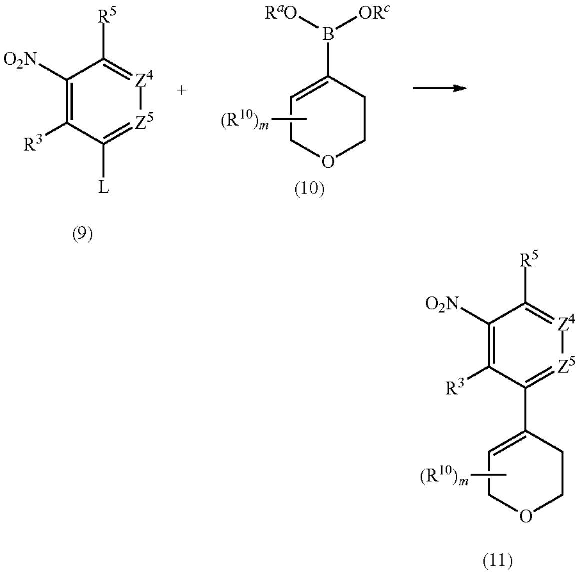

(9) (10) (11)

(In the formulae, $R^b$ and $R^c$ are the same as or different from each other and represent a hydrogen atom or a $C_{1-6}$ alkyl group, or $R^b$ and $R^c$ together form an ethylene group which may be substituted with one or more $C_{1-6}$ alkyl groups; and $Z^4$, $Z^5$, $R^3$, $R^5$, $R^{10}$, m, and L are as defined above.)

For example, 1-bromo-2-fluoro-3-nitrobenzene and 1-bromo-2,5-difluoro-3-nitrobenzene are known as the compound represented by General Formula (9).

For example, 3,6-dihydro-2H-pyran-4-boronic acid pinacol ester is known as the compound represented by General Formula (10).

In addition, the compound represented by General Formula (10) can be produced from the corresponding halide by a method known per se.

The compound represented by General Formula (11) can be produced by reacting the compound represented by General Formula (9) with the compound represented by General Formula (10) in the presence or absence of a base, in the presence of a palladium catalyst, and in the presence or absence of a ligand, according to the production method A.

[Production Method C]

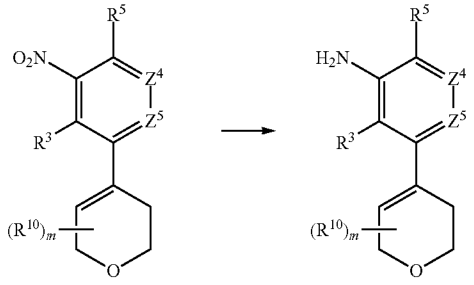

(11) (8a)

(In the formulae, $Z^4$, $Z^5$, $R^3$, $R^5$, $R^{10}$, and m are as defined above).

The compound represented by General Formula (8a) can be produced by reducing the compound represented by General Formula (11).

The reaction may be carried out by the method described in Comprehensive Organic Transformations, Richard C. Larock et al., 2nd Edition, pp. 823 to 827, 1999, John Wiley & Sons, Inc.) or a method similar thereto.

Specific examples of such a method include a catalytic hydrogenation reaction using a metal catalyst and a reduction reaction using a metal such as iron or zinc in the presence or absence of an acid and in the presence or absence of a salt.

<<Catalytic Hydrogenation Reaction Using Metal Catalyst>>

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be used in mixture.

Preferred solvents include ethers, esters, alcohols, and amides.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (11).

Examples of the metal catalyst used in the reaction include metal palladium such as palladium-carbon and palladium black; palladium salts such as palladium oxide and palladium hydroxide; and nickel metals such as Raney nickel and platinum salts such as platinum oxide.

The amount of the metal catalyst used is preferably 0.001 to 5 times (W/W) and more preferably 0.01 to 1 times (W/W) with respect to the amount of the compound represented by General Formula (11).

Examples of the reducing agent include hydrogen; formic acid; formates such as sodium formate, ammonium formate, and triethylammonium formate; and cyclohexene and cyclohexadiene.

The amount of the reducing agent used is preferably 2 to 100 times molar and more preferably 2 to 10 times molar with respect to the compound represented by General Formula (11).

The reaction may be carried out at 0° C. to 200° C., preferably 0° C. to 100° C. for 1 minute to 24 hours.

<<Reduction Reaction using Metal>>

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be used in mixture.

Preferred solvents include alcohols and water.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (11).

Examples of the metal used in the reaction include iron, zinc, tin, and tin (II) chloride.

The amount of the metal used is preferably 1 to 50 times molar and more preferably 1 to 10 times molar with respect to the compound represented by General Formula (11).

Examples of the acid used in the reaction include hydrogen chloride, hydrogen bromide, and acetic acid.

The amount of the acid used is preferably 0.001 to 100 times (W/V) and more preferably 0.01 to 20 times (W/V) with respect to the amount of the compound represented by General Formula (11).

Examples of the salt used in the reaction include ammonium chloride.

The amount of the salt used is preferably 0.01 to 10 times molar and more preferably 0.1 to 5 times molar with respect to the compound represented by General Formula (11).

The reaction may be carried out at 0° C. to 200° C., preferably 0° C. to 100° C. for 1 minute to 24 hours.

[Production Method D]

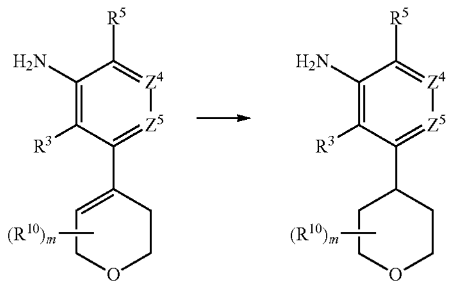

(8a) (8b)

(In the formulae, $Z^4$, $Z^5$, $R^3$, $R^5$, $R^{10}$, and m are as defined above).

The compound represented by General Formula (8b) can be produced by reducing the compound represented by General Formula (8a), according to the production method C.

[Production Method E]

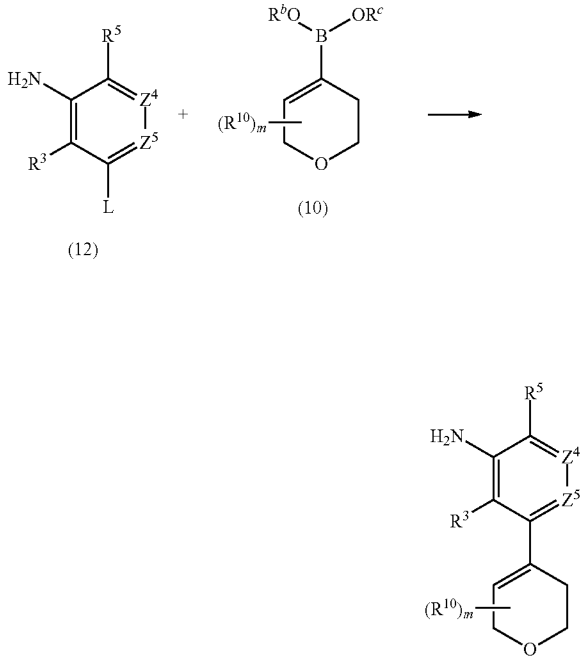

(12) (10) (8a)

(In the formulae, $Z^4$, $Z^5$, $R^3$, $R^5$, $R^{10}$, $R^b$, $R^c$, m, and L are as defined above.)

For example, 3-bromo-2-methoxyaniline and 3-bromo-2-methylaniline are known as the compound represented by General Formula (12).

The compound represented by General Formula (8a) can be produced by reacting the compound represented by General Formula (12) with the compound represented by General Formula (10) in the presence or absence of a base, in the presence of a palladium catalyst, and in the presence or absence of a ligand, according to the production method B.

[Production Method F]

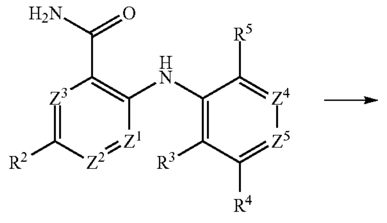

(1d)

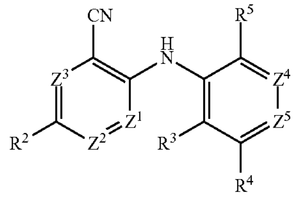

(4)

(In the formulae, $Z^1$, $Z^2$, $Z^3$, $Z^4$, $Z^5$, $R^2$, $R^3$, $R^4$, and $R^5$ are as defined above.)

The compound represented by General Formula (4) can be produced by reacting the compound represented by General Formula (1d) with a dehydrating agent in the presence or absence of a base.

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be used in mixture.

Preferred solvents include halogenated hydrocarbons and the like.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (2).

Examples of the base optionally used in the reaction include an inorganic base and an organic base.

Examples of the dehydrating agent used in the reaction include acid anhydrides such as acetylformyl oxide, acetic anhydride, trichloroacetic anhydride, and trifluoroacetic anhydride; mixed acid anhydrides of organic carboxylic acids such as acetic acid and monoalkyl carbonates such as ethyl chlorocarbonate and isobutyl chlorocarbonate; mixed acid anhydrides of organic carboxylic acids such as acetic acid and organic acids such as pivalic acid; acid chlorides such as acetyl chloride, trichloroacetyl chloride, and trifluoroacetyl chloride; and acid bromides such as acetyl bromide.

The amount of the base and the dehydrating agent used is preferably 1 to 10 times molar and more preferably 1 to 5 times molar with respect to the compound represented by General Formula (1d).

The reaction may be carried out at 0° C. to 200° C., preferably 0° C. to 100° C. for 1 minute to 24 hours.

[Production Method G]

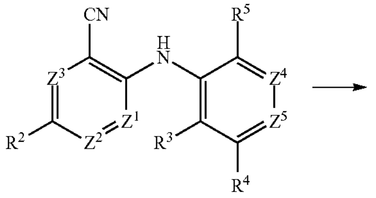

(4)

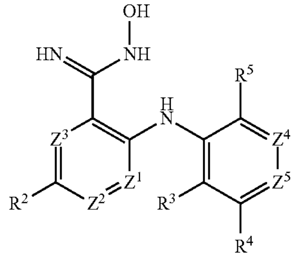

(5)

(In the formulae, $Z^1$, $Z^2$, $Z^3$, $Z^4$, $Z^5$, $R^2$, $R^3$, $R^4$, and $R^5$ are as defined above.)

The compound represented by General Formula (5) can be produced by reacting the compound represented by General Formula (4) with a hydroxylamine in the presence or absence of a base.

The solvent used in the reaction is not particularly limited as long as it does not adversely affect the reaction, and examples thereof include aliphatic hydrocarbons, halogenated hydrocarbons, alcohols, glycols, ethers, ketones, esters, amides, nitriles, sulfoxides, aromatic hydrocarbons, and water, which may be used in mixture.

Preferred solvents include amides and the like.

The amount of the solvent used is not particularly limited, and is preferably 1 to 100 times (v/w), more preferably 1 to 10 times (v/w), and still more preferably 1 to 5 times (v/w) with respect to the amount of the compound represented by General Formula (4).

Examples of the base optionally used in the reaction include an inorganic base and an organic base.

The amount of the base used is preferably 1 to 10 times molar and more preferably 1 to 5 times molar with respect to the compound represented by General Formula (4).

Examples of the hydroxylamine used in the reaction include hydroxylamine hydrochloride.

The amount of the hydroxylamine used may be 1 to 100 times molar and preferably 1 to 10 times molar with respect to the compound represented by General Formula (4).

The reaction may be carried out at 0° C. to 200° C., preferably 0° C. to 100° C. for 1 minute to 24 hours.

Among the compounds used in the above-mentioned production methods, a compound that can take the form of a salt can also be used as a salt. Examples of such a salt include the same salts as the salts of the compound represented by General Formula (1).

In a case where isomers (for example, an optical isomer, a geometric isomer, and a tautomer) are present for the compounds used in the above-mentioned production methods, these isomers can also be used. In addition, in a case where solvates, hydrates, and various forms of crystals are present, these solvates, hydrates, and various forms of crystals can also be used.

The compound represented by General Formula (1) can be derived into another compound represented by General Formula (1), for example, by subjecting the compound to a reaction known per se such as condensation, addition, oxidation, reduction, transition, substitution, halogenation, dehydration, or hydrolysis, or an appropriate combination of these reactions.

In addition, among the compounds used in the above-mentioned production methods, in a case of a compound having a group that can be protected, for example, an amino group, a hydroxyl group, or a carboxyl group, such a group can be protected with a normal protective group in advance, and after the reaction, the protective group can be removed by a method known per se.

In a case where the compound according to the embodiment of the present invention is used as a pharmaceutical composition, a pharmaceutical aid such as an excipient, a carrier, or a diluent which is usually used for formulation may be appropriately mixed. The pharmaceutical aid can be administered orally or parenterally in the form of a tablet, a capsule, a powder, a syrup, a granule, a pill, a suspension, an emulsion, a solution, a powdery preparation, a suppository, an eye drop, a nasal drop, an ear drop, a patch, an ointment, an injection, or the like according to a conventional method. In addition, a method of administration, a given dose, and a frequency of administration can be appropriately selected according to the age, weight, and condition of the patient. Usually, for an adult, 0.01 to 1,000 mg/kg/day may be administered singly or in several divided doses by oral or parenteral administration (for example, injection, drip infusion, or rectal administration).

The compound or salt thereof according to the embodiment of the present invention has an excellent anti-tumor activity and can be used for the treatment of a tumor.

The treatment refers to preventing, treating, or the like of a variety of diseases.

The treatment agent refers to a substance which is provided for the purpose of preventing or treating a variety of diseases.

The preventing refers to inhibition of disease onset, reduction of disease onset risk, delay of disease onset, or the like.

The treating refers to improvement of, suppression of progression of, or the like of a target disease or condition.

The tumor refers to a benign tumor or a malignant tumor.

The benign tumor refers to a tumor in which a tumor cell and a sequence thereof have a morphology close to that of a normal cell from which such a tumor cell is derived and which is not invasive or metastatic.

The malignant tumor refers to a tumor in which the morphology and sequence of a tumor cell are different from those of a normal cell from which such a tumor cell is derived and which is invasive or metastatic.

The anti-tumor agent according to the embodiment of the present invention is preferably used as an antineoplastic agent, and is more preferably used as a cancer treatment agent (preferably a blood cancer treatment agent).

Examples of the blood cancer include acute lymphocytic leukemia (ALL), acute myelogenous leukemia (AML), acute promyelogenous leukemia (APL), chronic lymphocytic leukemia (CLL), chronic myelogenous leukemia (CML), chronic neutrophilic leukemia (CNL), acute undifferentiated leukemia (AUL), anaplastic large cell lymphoma (ALCL), prolymphocytic leukemia (PLL), juvenile myelomonocytic leukemia (JMML), adult T-cell (ATL), myelodysplastic syndrome (MDS), myeloproliferative disease (MPD), lymphoblastic lymphoma (LBL), and adult T-cell leukemia/lymphoma (ATLL).

The compound or salt thereof according to the embodiment of the present invention can also be used as a dihydroorotate dehydrogenase inhibitor.

The compound or salt thereof according to the embodiment of the present invention can be used as a treatment agent (for example, an anti-tumor agent or an antirheumatic agent) for a disease associated with dihydroorotate dehydrogenase such as tumor or rheumatism.

The dihydroorotate dehydrogenase inhibitor according to the embodiment of the present invention can be used in the same manner as in the above-mentioned pharmaceutical composition and anti-tumor agent according to the embodiment of the present invention.

EXAMPLES

Hereinafter, the present invention will be described with reference to Reference Examples and Examples, but the present invention is not limited thereto.

Unless otherwise specified, purification by column chromatography was carried out using an automated purification apparatus ISOLERA (manufactured by Biotage) or a medium-pressure liquid chromatograph YFLC-Wprep2XY.N (manufactured by Yamazen Corporation).

Unless otherwise specified, SNAPKP-Sil Cartridge (manufactured by Biotage), HI-FLASH COLUMN W001, W002, W003, W004, or W005 (manufactured by Yamazen Corporation), and CHROMATOREX Q-PACK Cartridge (manufactured by Fuji Silysia Chemical Ltd.) were used as carriers in silica gel column chromatography.

In preparative thin layer chromatography, PLC glass plate silica gel $F_{60}$ (manufactured by Merck & Co., Inc.) was used.

The mixing ratio in the eluent was a volume ratio. For example, "hexane:ethyl acetate gradient elution=50:50 to 0:100" means that an eluent of 50% hexane/50% ethyl acetate was finally changed to an eluent of 0% hexane/100% ethyl acetate.

Initiator Sixty (manufactured by Biotage) was used as a microwave reactor.

The NMR spectrum was measured using Bruker AV300 (manufactured by Bruker Corporation, 300 MHz), Bruker AV400 (manufactured by Bruker Corporation, 400 MHz), and Bruker Fourier-400 (manufactured by Bruker Corporation, 400 MHz) and using tetramethylsilane as an internal reference. All 6 values are shown in ppm.

The MS spectrum was measured using ACQUITY SQD LC/MS System (manufactured by Waters Corporation, ionization method: Electro Spray Ionization (ESI) method), Micromass ZQ2000 LCMS System (manufactured by Waters Corporation, ionization method: ESI), Model M-8000 (manufactured by Hitachi, Ltd., ionization method: ESI method), or LCMS-2010EV (manufactured by Shimadzu Corporation, ionization method: method of carrying out ESI and Atmospheric Pressure Chemical Ionization (APCI) at the same time).

The retention time (RT) was measured using SQD (manufactured by Waters Corporation) and 2695 Separations Module (manufactured by Waters Corporation), and was shown in minutes (min).

The measurement was carried out under the following conditions.

Method A

Column: BEHC 18 1.7 μm, 2.1×30 mm (manufactured by Waters Corporation)

Solvent: liquid A: 0.1% formic acid-water liquid B: 0.1% formic acid-acetonitrile Gradient cycle: 0.00 min (liquid A/liquid B=95/5), 2.00 min (liquid A/liquid B=5/95), 3.00 min (liquid A/liquid B=5/95), 3.01 min (liquid A/liquid B=100/0), 3.80 min (liquid A/liquid B=100/0)

Flow rate: 0.5 mL/min

Column temperature: room temperature

Detection wavelength: 254 nm

Method B

Column: XBridge C18 5 μm, 3.0×50 mm (manufactured by Waters Corporation)

Solvent: liquid A: 0.05% trifluoroacetic acid-water liquid B: 0.05% trifluoroacetic acid-acetonitrile Gradient cycle: 0.00 min (liquid A/liquid B=90/10), 1.00 min (liquid A/liquid B=90/10), 1.50 min (liquid A/liquid B=70/30), 4.50 min (liquid A)/liquid B=30/70), 5.00 min (liquid A/liquid B=10/90), 6.00 min (liquid A/liquid B=10/90), 6.20 min (liquid A/liquid B=90/10), 7.00 min (liquid A/liquid B=90/10)

Flow rate: 1.27 mL/min

Column temperature: 30° C.

Detection wavelength: 254 nm

In each of Examples, each abbreviation has the following meaning.

RT (min): retention time (minutes)

Reference Example 1-1

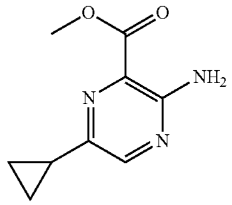

The following compound was obtained according to the method described in US2011/306589A.

Methyl 3-amino-6-cyclopropylpyrazine-2-carboxylate

LCMS (Method A)

MS (ESI m/z): 194 (M+H)

RT (min): 0.92

Reference Example 1-2

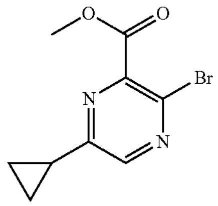

The following compound was obtained according to the method described in US2011/306589A.

Methyl 3-bromo-6-cyclopropylpyrazine-2-carboxylate

LCMS (Method A)

MS (ESI m/z): 258 (M+H)

RT (min): 1.31

Reference Example 1-3

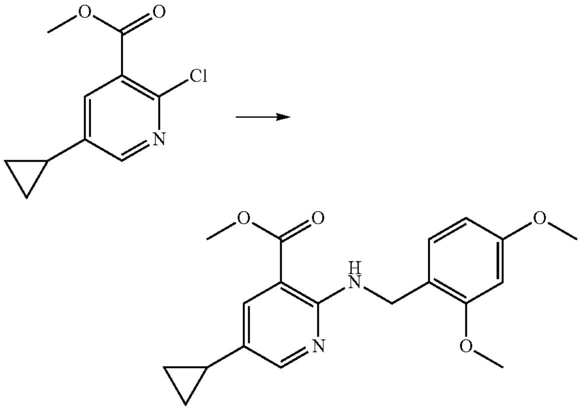

A mixture of methyl 2-chloro-5-cyclopropylnicotinate (5.0 g), diethylene glycol ethylmethyl ether (15 mL), cesium carbonate (8.5 g), and 2,4-dimethoxybenzylamine (4.4 g) was stirred at 180° C. for 1 hour. After cooling to room temperature, water was added to the reaction liquid which was then extracted with ethyl acetate. The organic layer was washed with an aqueous sodium chloride solution and dried over magnesium sulfate, and then the solvent was distilled off under reduced pressure. The obtained residue was purified by silica gel column chromatography (hexane:ethyl acetate gradient elution=100:0 to 80:20) to obtain methyl 5-cyclopropyl-2-((2,4-dimethoxybenzyl)amino)nicotinate (5.8 g) as a white solid.

1H-NMR (CDCl3) δ: 8.16 (d, 1H, J=2.7 Hz), 8.10-8.03 (m, 1H), 7.79 (d, 1H, J=2.7 Hz), 7.23 (d, 1H, J=8.5 Hz), 6.47 (d, 1H, J=2.2 Hz), 6.44-6.40 (m, 1H), 4.65 (d, 2H, J=5.8 Hz), 3.85 (s, 3H), 3.84 (s, 3H), 3.79 (s, 3H), 1.83-1.74 (m, 1H), 0.92-0.85 (m, 2H), 0.64-0.56 (m, 2H).

Reference Example 1-4

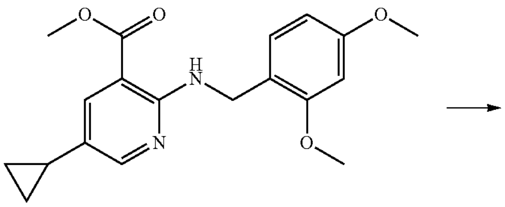

-continued

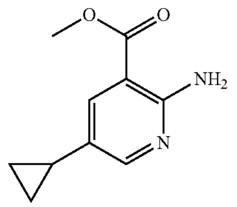

A mixture of methyl 5-cyclopropyl-2((2,4-dimethoxybenzyl)amino)nicotinate (5.8 g), dichloromethane (29 mL), and trifluoroacetic acid (29 mL) was stirred at room temperature for 2 hours. Ethyl acetate, water, an aqueous sodium hydrogen carbonate solution, and a 5 mol/L aqueous sodium hydroxide solution were added to the reaction liquid, and the solid matter was filtered off. The organic layer of the filtrate was separated, washed with an aqueous sodium chloride solution, and dried over magnesium sulfate. The obtained residue was purified by silica gel column chromatography (hexane:ethyl acetate gradient elution=80:20 to 0:100). Hexane was added to the purified product, and the mixture was stirred and then filtered to obtain methyl 2-amino-5-cyclopropylnicotinate (1.5 g) as a white solid.

LCMS (Method A)

MS (ESI m/z): 193 (M+H)

RT (min): 0.69

Reference Example 1-5

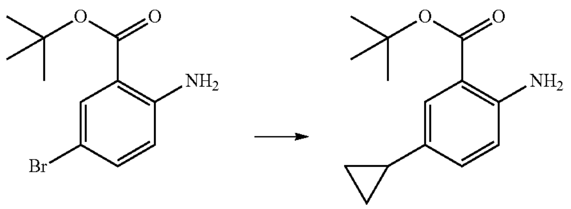 [SMILES: CC(C)(C)OC(=O)c1cc(Br)ccc1N ; CC(C)(C)OC(=O)c1cc(C2CC2)ccc1N]

A mixture of tert-butyl 2-amino-5-bromobenzoate (6.4 g), cyclopropylboronic acid monohydrate (2.7 g), bis(di-tert-butyl(4-dimethylaminophenyl)phosphine)dichloropalladium (II) (0.83 g), potassium phosphate (11 g), 1,4-dioxane (24 mL), and water (8.0 mL) was stirred at 120° C. for 30 minutes. After cooling to room temperature, an aqueous sodium chloride solution was added to the reaction liquid which was then extracted twice with ethyl acetate. After drying over magnesium sulfate, the solvent of the organic layer was distilled off under reduced pressure. The obtained residue was purified by silica gel column chromatography (hexane:ethyl acetate gradient elution=20:1 to 2:1). Hexane was added to the purified product, and the mixture was stirred and then filtered to obtain tert-butyl 2-amino-5-cyclopropylbenzoate (1.97 g) as a yellow solid.

1H-NMR (CDCl3) δ: 7.57 (d, 1H, J=2.3 Hz), 7.00-6.95 (m, 1H), 6.57 (d, 1H, J=8.5 Hz), 5.65-5.41 (m, 2H), 1.86-1.76 (m, 1H), 1.59 (s, 9H), 0.89-0.81 (m, 2H), 0.61-0.54 (m, 2H)

Reference Example 1-6

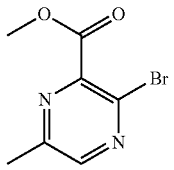

The following compound was obtained according to the method described in WO2019/043407A.

Methyl 3-bromo-6-methylpyrazine-2-carboxylate

LCMS (Method A)

MS (ESI m/z): 230 (M+H)

RT (min): 0.96

Reference Example 1-7

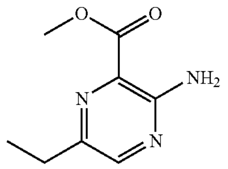

The following compound was obtained according to the method described in WO2017/221008A.

Methyl 3-amino-6-ethylpyrazine-2-carboxylate

LCMS (Method A)

MS (ESI m/z): 182 (M+H)

RT (min): 0.78

Reference Example 1-8

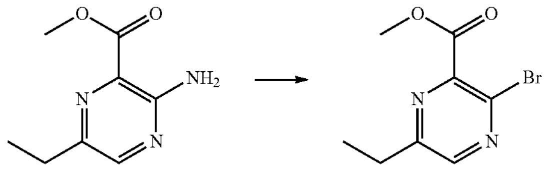

Bromotrimethylsilane (0.85 mL) was added to a mixture of methyl 3-amino-6-ethylpyrazine-2-carboxylate (0.39 g) and dibromomethane (3.9 mL) under water cooling. After stirring at room temperature, pentyl nitrite (0.64 mL) was added to the mixture which was then stirred at 10° C. to 20° C. for 1 hour. An aqueous sodium hydrogen carbonate solution was added thereto, and the organic layer was separated. Chloroform was added to the aqueous layer for extraction. The organic layers were combined, the solvent was distilled off under reduced pressure, and the obtained residue was purified by silica gel column chromatography (hexane:ethyl acetate gradient elution=100:0 to 90:10) to obtain methyl 3-bromo-6-ethylpyrazine-2-carboxylate (0.42 g) as a light brown oil.

LCMS (Method A)
MS (ESI m/z): 246 (M+H)
RT (min): 1.17

Reference Example 1-9

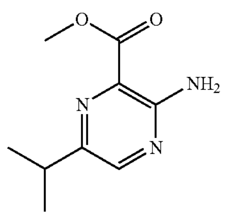

The following compound was obtained according to the method described in US2011/306589A.

Methyl 3-amino-6-isopropylpyrazine-2-carboxylate

LCMS (Method A)
MS (ESI m/z): 196 (M+H)
RT (min): 0.98

Reference Example 1-10

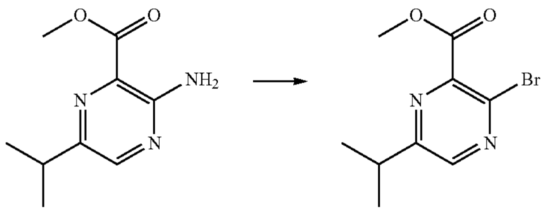

Methyl 3-bromo-6-isopropylpyrazine-2-carboxylate was obtained in the same manner as in Reference Example 1-8.
LCMS (Method A)
MS (ESI m/z): 259 (M+H)
RT (min): 1.37

Reference Example 2-1

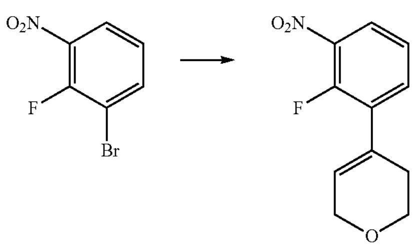 [SMILES: O=[N+]([O-])c1cccc(Br)c1F ; O=[N+]([O-])c1cccc(C2=CCOCC2)c1F]

A mixture of 1-bromo-2-fluoro-3-nitrobenzene (1.0 g), 3,6-dihydro-2H-pyran-4-boronic acid pinacol ester (1.1 g), bis(di-tert-butyl (4-dimethylaminophenyl)phosphine)dichloropalladium (II) (0.16 g), potassium phosphate (1.9 g), 1,2-dimethoxyethane (10 mL), and water (2.0 mL) was irradiated with microwaves (microwave reactor, 110° C., 30 minutes, 2.45 GHz, 0 to 240 W). An aqueous sodium chloride solution was added to the reaction liquid which was then extracted twice with ethyl acetate. The solvent of the organic layer was distilled off under reduced pressure, and the obtained residue was purified by silica gel column chromatography to obtain 4-(2-fluoro-3-nitrophenyl)-3,6-dihydro-2H-pyran (0.95 g) as a brown solid.

1H-NMR (CDCl3) δ: 7.93-7.88 (m, 1H), 7.56-7.51 (m, 1H), 7.29-7.22 (m, 1H), 6.11-6.07 (m, 1H), 4.37-4.32 (m, 2H), 3.94 (t, 2H, J=5.6 Hz), 2.56-2.48 (m, 2H).

Reference Example 2-2

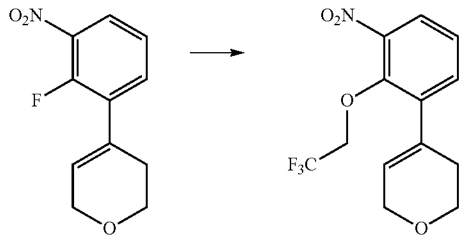 [SMILES: O=[N+]([O-])c1cccc(C2=CCOCC2)c1F ; O=[N+]([O-])c1cccc(C2=CCOCC2)c1OCC(F)(F)F]

60% sodium hydride (22 mg) was added to a mixture of 4-(2-fluoro-3-nitrophenyl)-3,6-dihydro-2H-pyran (60 mg), 2,2,2-trifluoroethanol (34 μL), and N,N-dimethylformamide (0.50 mL) under ice cooling, and the mixture was stirred at room temperature for 5 minutes. Water was added to the reaction liquid which was then extracted twice with ethyl acetate. The solvent of the organic layer was distilled off under reduced pressure, toluene was added, and the solvent was then distilled off under reduced pressure. Toluene was further added and the solvent was distilled off under reduced pressure to obtain 4-(3-nitro-2-(2,2,2-trifluoroethoxy)phenyl)-3,6-dihydro-2H-pyran (80 mg) as a brown oil.

1H-NMR (CDCl3) δ: 7.76 (dd, 1H, J=7.9, 2.0 Hz), 7.45 (dd, 1H, J=7.6, 1.7 Hz), 7.29 (dd, 1H, J=7.9, 7.6 Hz), 6.04-6.01 (m, 1H), 4.36 (q, 2H, J=8.3 Hz), 4.34-4.30 (m, 2H), 3.93 (t, 2H, J=5.3 Hz), 2.53-2.45 (m, 2H).

Reference Example 2-3

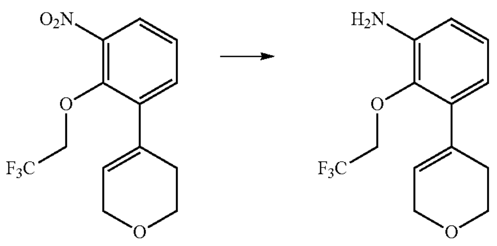 [SMILES: O=[N+]([O-])c1cccc(C2=CCOCC2)c1OCC(F)(F)F ; Nc1cccc(C2=CCOCC2)c1OCC(F)(F)F]

A mixture of 4-(3-nitro-2-(2,2,2-trifluoroethoxy)phenyl)-3,6-dihydro-2H-pyran (80 mg), ammonium chloride (29 mg), isopropyl alcohol (1.0 mL), and water (0.50 mL) was stirred at 90° C., and iron (150 mg) was added thereto, followed by stirring for 40 minutes. After cooling to room temperature, the insoluble matter was removed, and an aqueous sodium chloride solution was added, followed by extraction twice with ethyl acetate. The solvent of the organic layer was distilled off under reduced pressure to obtain 3-(3,6-dihydro-2H-pyran-4-yl)-2-(2,2,2-trifluoroethoxy)aniline (68 mg) as a brown oil.

LCMS (Method A)

MS (ESI m/z): 274 (M+H)

RT (min): 1.33

Reference Example 2-4

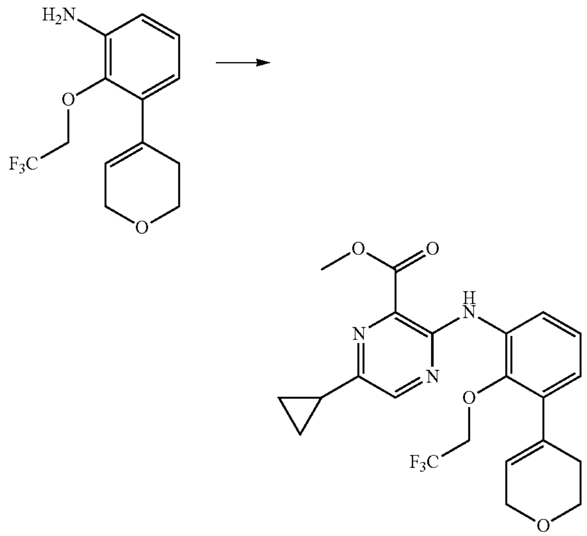

A mixture of 3-(3,6-dihydro-2H-pyran-4-yl)-2-(2,2,2-trifluoroethoxy)aniline (34 mg), methyl 3-bromo-6-cyclopropylpyrazine-2-carboxylate (45 mg), tris(dibenzylideneacetone)dipalladium (0) (25 mg), 4,5-bis(diphenylphosphino)-9,9-dimethylxanthene (31 mg), cesium carbonate (88 mg), and toluene (2.0 mL) was irradiated with microwaves (microwave reactor, 140° C., 1.5 hours, 2.45 GHz, 0 to 240 W). Water was added to the reaction liquid which was then extracted twice with ethyl acetate. The solvent of the organic layer was distilled off under reduced pressure, and the obtained residue was purified by silica gel column chromatography (hexane:ethyl acetate gradient elution=100:0 to 80:20) to obtain methyl 6-cyclopropyl-3-((3-(3,6-dihydro-2H-pyran-4-yl)-2-(2,2,2-trifluoroethoxy)phenyl)amino) pyrazine-2-carboxylate (60 mg) as a yellow solid.

LCMS (Method A)

MS (ESI m/z): 450 (M+H)

RT (min): 1.90

Reference Example 2-5

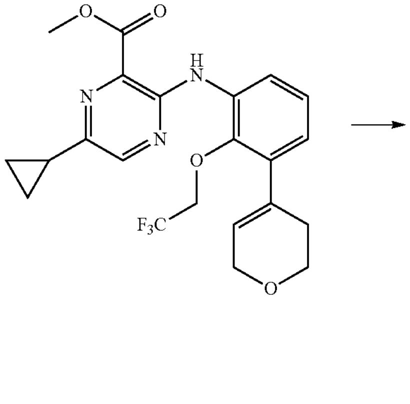

-continued

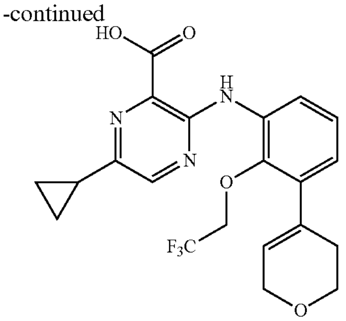

A mixture of methyl 6-cyclopropyl-3-((3-(3,6-dihydro-2H-pyran-4-yl)-2-(2,2,2-trifluoroethoxy)phenyl)amino) pyrazine-2-carboxylate (60 mg), a 5 mol/L aqueous sodium hydroxide solution (53 μL), tetrahydrofuran (0.50 mL), and ethanol (0.50 mL) was stirred at 50° C. for 1 hour. After cooling to room temperature, the pH was adjusted to 6 with 1 mol/L hydrochloric acid. An aqueous sodium chloride solution was added to the mixture which was then extracted twice with ethyl acetate. The solvent of the organic layer was distilled off under reduced pressure, and the obtained residue was purified by silica gel column chromatography (hexane: ethyl acetate gradient elution=100:0 to 70:30) to obtain 6-cyclopropyl-3-((3-(3,6-dihydro-2H-pyran-4-yl)-2-(2,2,2-trifluoroethoxy)phenyl)amino)pyrazine-2-carboxylic acid (39 mg) as a yellow solid.

1H-NMR (DMSO-D6) δ: 13.41 (br s, 1H), 10.54 (br s, 1H), 8.43 (s, 1H), 8.34 (dd, 1H, J=8.6, 1.3 Hz), 7.17 (dd, 1H, J=7.9, 8.6 Hz), 6.90 (dd, 1H, J=7.9, 1.3 Hz), 5.97 (s, 1H), 4.42 (q, 2H, J=9.0 Hz), 4.24-4.17 (m, 2H), 3.82 (t, 2H, J=5.3 Hz), 2.42 (br s, 2H), 2.21-2.11 (m, 1H), 1.01-0.91 (m, 4H).

MS (ESI m/z): 436 (M+H)

RT (min): 1.74

Reference Example 2-6

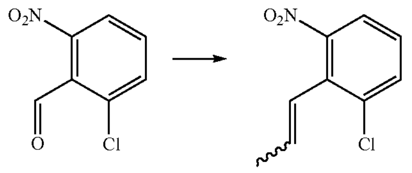

A mixture of 2-chloro-6-nitrobenzaldehyde (1.0 g), potassium carbonate (1.5 g), ethyltriphenylphosphonium iodide (2.7 g), and tetrahydrofuran (10 mL) was stirred with heating under reflux for 4.5 hours. Isopropyl alcohol (10 mL) was added to the mixture which was then stirred with heating under reflux for 5 hours. After cooling to room temperature, an aqueous ammonium chloride solution was added to the reaction liquid which was then extracted with toluene. The organic layer was washed with a 10% aqueous methanol solution, washed with a saturated aqueous sodium chloride solution, and dried over magnesium sulfate. The solvent was distilled off under reduced pressure, and the obtained residue was purified by silica gel column chromatography (hexane:ethyl acetate gradient elution=100:0 to 90:10) to obtain 1-chloro-3-nitro-2-(propa-1-en-1-yl)benzene (0.74 g) as a yellow oil.

1H-NMR (CDCl3) δ: 8.31-7.08 (m, 3H), 6.48-6.42 (m, 1H), 6.05-5.85 (m, 1H), 1.91-1.43 (m, 3H).

Reference Example 2-7

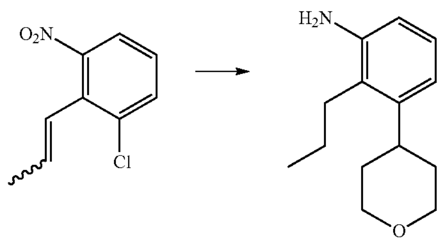

A mixture of 1-chloro-3-nitro-2-(propa-1-en-1-yl)benzene (0.74 g), 3,6-dihydro-2H-pyran-4-boronic acid pinacol ester (0.99 g), bis(di-tert-butyl(4-dimethylaminophenyl) phosphine)dichloropalladium (II) (0.27 g), potassium phosphate (2.0 g), 1,2-dimethoxyethane (11 mL), and water (3.7 mL) was irradiated with microwaves (microwave reactor, 100° C., 1 hour, 2.45 GHz, 0 to 240 W). An aqueous sodium chloride solution was added to the reaction liquid which was then extracted with ethyl acetate. The organic layer was dried over magnesium sulfate. The solvent was distilled off under reduced pressure, and the obtained residue was purified by silica gel column chromatography (hexane:ethyl acetate gradient elution=100:0 to 80:20) to obtain a brown oil (0.61 g). A mixture of the obtained oil (0.30 g), 10% palladium on carbon (0.30 g), ammonium formate (3.9 g), and methanol (24 mL) was stirred with heating under reflux for 2 hours. After cooling to room temperature, water and ethyl acetate were added to the reaction liquid, and solid matter was removed by filtration through Celite. The organic layer was separated, washed with a saturated aqueous sodium chloride solution, and then dried over magnesium sulfate. The solvent was distilled off under reduced pressure, and the obtained residue was purified by silica gel column chromatography (hexane:ethyl acetate gradient elution=100:0 to 80:20) to obtain 2-propyl-3-(tetrahydro-2H-pyran-4-yl)aniline (0.24 g) as a white solid.

LCMS (Method A)

MS (ESI m/z): 220 (M+H)

RT (min): 0.89

Reference Example 2-8

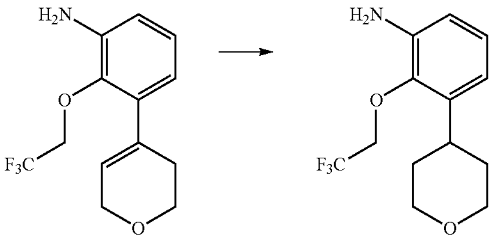 [SMILES: Nc1cccc(C2=CCOCC2)c1OCC(F)(F)F ; Nc1cccc(C2CCOCC2)c1OCC(F)(F)F]

A mixture of 3-(3,6-dihydro-2H-pyran-4-yl)-2-(2,2,2-trifluoroethoxy)aniline (50 mg), 10% palladium on carbon (29 mg), ammonium formate (0.46 g), and methanol (2.0 mL) was stirred with heating under reflux for 1.5 hours. 10% palladium on carbon (20 mg) and ammonium formate (0.23 g) were added to the mixture which was then stirred for 1.5 hours. After cooling to room temperature, solid matter was removed by filtration through Celite. Water was added to the filtrate which was then extracted twice with ethyl acetate. The solvent of the organic layer was distilled off under reduced pressure to obtain 3-(tetrahydro-2H-pyran-4-yl)-2-(2,2,2-trifluoroethoxy)aniline (32 mg) as a yellow oil.

LCMS (Method A)

MS (ESI m/z): 276 (M+H)

RT (min): 1.33

Reference Example 2-9

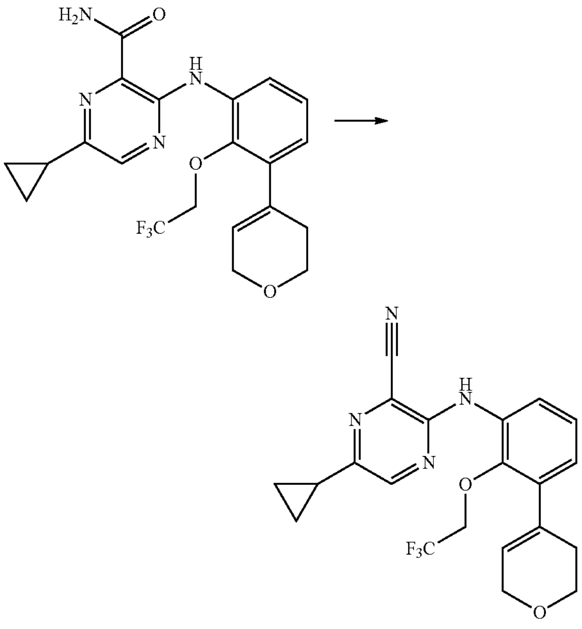

A) A mixture of 6-cyclopropyl-3-((3-(3,6-dihydro-2H-pyran-4-yl)-2-(2,2,2-trifluoroethoxy)phenyl)amino)pyrazine-2-carboxamide (100 mg), methyl N-(triethylammoniosulfonyl)carbamate (137 mg), and dichloromethane (1.5 mL) was stirred at room temperature for 5 hours and 30 minutes. Methyl N-(triethylammoniosulfonyl)carbamate (55 mg) was added to the mixture which was then stirred for 15 hours and 30 minutes. The mixture was passed through silica gel (5.0 g) and eluted with dichloromethane, and the solvent was distilled off under reduced pressure.

B) A mixture of 6-cyclopropyl-3-((3-(3,6-dihydro-2H-pyran-4-yl)-2-(2,2,2-trifluoroethoxy)phenyl)amino)pyrazine-2-carboxamide (200 mg), methyl N-(triethylammoniosulfonyl)carbamate (384 mg), and dichloromethane (3.0 mL) was stirred at room temperature for 22 hours. The mixture was passed through silica gel (5.0 g) and eluted with dichloromethane, and the solvent was distilled off under reduced pressure.

The residues obtained in A and B were purified by NH silica gel column chromatography (hexane:ethyl acetate gradient elution=90:10 to 80:20) to obtain 6-cyclopropyl-3-((3-(3,6-dihydro-2H-pyran-4-yl)-2-(2,2,2-trifluoroethoxy) phenyl)amino)pyrazine-2-carbonitrile (259 mg) as a yellow solid.

1H-NMR (CDCl3) δ: 8.27 (s, 1H), 8.20 (dd, 1H, J=8.2, 1.6 Hz), 7.63 (br s, 1H), 7.17 (t, 1H, J=8.1 Hz), 6.92 (dd, 1H, J=7.7, 1.6 Hz), 6.02 (s, 1H), 4.35-4.32 (m, 2H), 4.25 (q, 2H, J=8.3 Hz), 3.94 (t, 2H, J=5.4 Hz), 2.54-2.47 (m, 2H), 2.07-1.99 (m, 1H), 1.05-0.99 (m, 4H).

LCMS (Method B)

MS (ESI m/z): 417 (M+H)

RT (min): 4.85

Reference Example 2-10

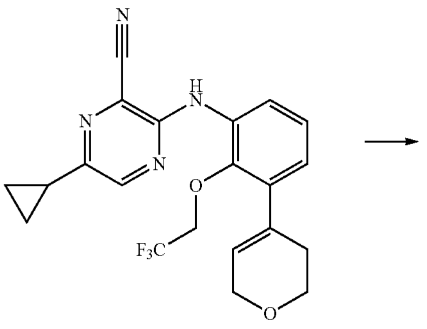

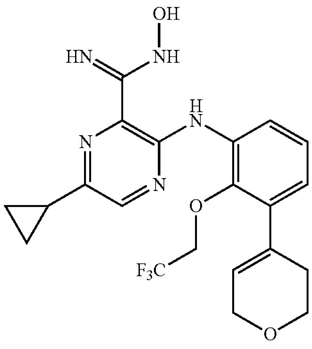

A mixture of 6-cyclopropyl-3-((3-(3,6-dihydro-2H-pyran-4-yl)-2-(2,2,2-trifluoroethoxy)phenyl)amino)pyrazine-2-carbonitrile (100 mg), N,N-dimethylformamide (4.0 mL), hydroxylamine hydrochloride (68 mg), and N,N-diisopropylethylamine (126 mg) was stirred at 70° C. for 2 hours and 30 minutes. The mixture was cooled to room temperature and water was added thereto. The precipitated solid was collected by filtration and dried to obtain 6-cyclopropyl-3-((3-(3,6-dihydro-2H-pyran-4-yl)-2-(2,2,2-trifluoroethoxy)phenyl)amino)-N-hydroxypyrazine-2-carboximidamide (105 mg) as a white solid.

1H-NMR (CDCl3) δ: 10.59 (br s, 1H), 8.48 (dd, 1H, J=8.2, 1.6 Hz), 8.12 (s, 1H), 7.14 (t, 1H, J=7.9 Hz), 6.82 (dd, 1H, J=7.7, 1.6 Hz), 6.55 (s, 1H), 5.94 (br s, 1H), 5.68 (br s, 2H), 4.32 (d, 2H, J=2.7 Hz), 4.22 (q, 2H, J=8.6 Hz), 3.94 (t, 2H, J=5.5 Hz), 2.55-2.49 (m, 2H), 2.09-2.00 (m, 1H), 1.01-0.94 (m, 4H).

LCMS (Method B)

MS (ESI m/z): 450 (M+H)

RT (min): 4.72

Reference Example 2-11

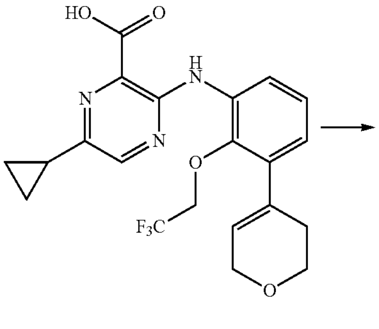

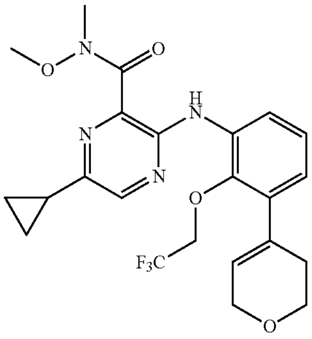

Under ice cooling, N,O-dimethylhydroxylamine hydrochloride (180 mg) and N,N-diisopropylethylamine (475 mg) were added to a mixture of 6-cyclopropyl-3-((3-(3,6-dihydro-2H-pyran-4-yl)-2-(2,2,2-trifluoroethoxy)phenyl)amino)pyrazine-2-carboxylic acid (400 mg), 1-(3-dimethylaminopropyl)-3-ethylcarbodiimide hydrochloride (270 mg), 1-hydroxybenzotriazole hydrate (210 mg), and N,N-dimethylformamide (8.0 mL) which was then stirred at room temperature for 18 hours. An aqueous ammonium chloride solution was added to the mixture which was then extracted with ethyl acetate. The organic layer was washed with an aqueous sodium hydrogen carbonate solution, water, and an aqueous sodium chloride solution, and dried over sodium sulfate. The solvent of the organic layer was distilled off under reduced pressure, and the obtained residue was purified by silica gel column chromatography (hexane:ethyl acetate gradient elution=90:10 to 75:25) to obtain 6-cyclopropyl-3-((3-(3,6-dihydro-2H-pyran-4-yl)-2-(2,2,2-trifluoroethoxy)phenyl)amino)-N-methoxy-N-methylpyrazine-2-carboxamide (450 mg) as a yellow oil.

1H-NMR (CDCl3) δ: 8.20-8.13 (m, 2H), 7.12 (t, 1H, J=7.9 Hz), 6.84 (dd, 1H, J=7.3, 1.7 Hz), 5.96 (br s, 1H), 4.31 (q, 2H, J=2.7 Hz), 4.22 (q, 2H, J=8.5 Hz), 3.92 (t, 2H, J=5.4 Hz), 3.84 (s, 3H), 3.44 (br s, 3H), 2.54-2.46 (m, 2H), 2.07-1.99 (m, 1H), 1.01-0.91 (m, 4H).

LCMS (Method B)

MS (ESI m/z): 479 (M+H)

RT (min): 4.88

Reference Example 2-12

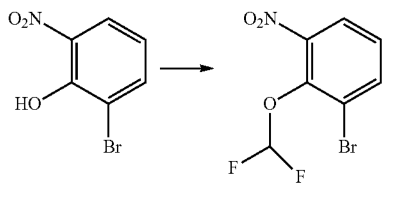 [SMILES: O=[N+]([O-])c1cccc(Br)c1O ; O=[N+]([O-])c1cccc(Br)c1OC(F)F]

Diethyl (bromodifluoromethyl)phosphonate (2.7 g) was added dropwise to a mixture of 2-bromo-6-nitrophenol (2.0 g), acetonitrile (30 mL), water (10 mL), and a 50% aqueous potassium hydroxide solution (10 g), followed by stirring at room temperature for 30 minutes. Diethyl (bromodifluoromethyl)phosphonate (0.49 g) was added to the mixture which was then stirred at room temperature for 10 minutes. Diethyl (bromodifluoromethyl)phosphonate (0.49 g) was added to the mixture which was then stirred at room temperature for 10 minutes. Water was added to the reaction liquid which was then extracted twice with toluene. The solvent was distilled off under reduced pressure to obtain 1-bromo-2-(difluoromethoxy)-3-nitrobenzene (2.9 g) as a brown oil.

1H-NMR (DMSO-D6) δ: 8.16 (dd, 1H, J=8.0, 1.3 Hz), 8.11 (dd, 1H, J=8.0, 1.3 Hz), 7.54 (t, 1H, J=7.9 Hz), 7.26 (t, 1H, J=71.6 Hz).

Reference Example 2-13

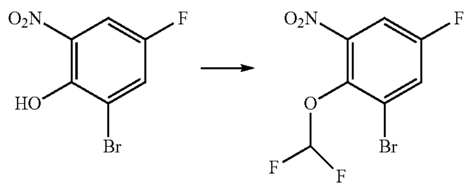 [SMILES: O=[N+]([O-])c1cc(F)cc(Br)c1O ; O=[N+]([O-])c1cc(F)cc(Br)c1OC(F)F]

1-Bromo-2-(difluoromethoxy)-5-fluoro-3-nitrobenzene was obtained in the same manner as in Reference Example 2-12.

1H-NMR (CDCl3) δ: 7.68-7.62 (m, 2H), 6.66 (t, 1H, J=85.7 Hz).

Reference Example 2-14

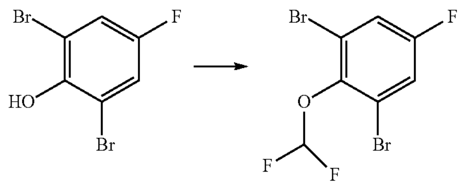 [SMILES: Oc1c(Br)cc(F)cc1Br ; Fc1cc(Br)c(OC(F)F)c(Br)c1]

1,3-Dibromo-2-(difluoromethoxy)-5-fluorobenzene was obtained in the same manner as in Reference Example 2-12.

1H-NMR (CDCl3) δ: 7.36 (d, 2H, J=7.3 Hz), 6.57 (t, 1H, J=73.9 Hz).

Reference Example 2-15

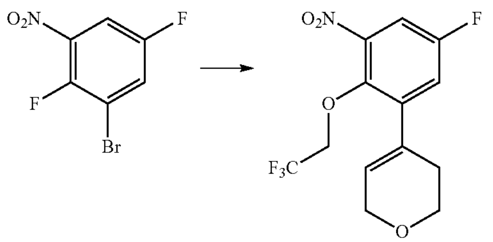 [SMILES: O=[N+]([O-])c1cc(F)cc(Br)c1F ; O=[N+]([O-])c1cc(F)cc(C2=CCOCC2)c1OCC(F)(F)F]

Under ice cooling, 60% sodium hydride (0.12 g) was added to a mixture of 1-bromo-2,5-difluoro-3-nitrobenzene (0.60 g), 2,2,2-trifluoroethanol (0.24 mL), and N,N-dimethylformamide (6.0 mL) which was then stirred for 1 hour. Water was added to the reaction liquid which was then extracted with ethyl acetate. The organic layer was washed with water and a saturated aqueous sodium chloride solution and dried over magnesium sulfate. The solvent was distilled off under reduced pressure to obtain a residue. A mixture of the obtained residue (0.80 g), 3,6-dihydro-2H-pyran-4-boronic acid pinacol ester (0.61 g), [1,1'-bis(diphenylphosphino)ferrocene]palladium (II) dichloride dichloromethane adduct (0.10 g), sodium carbonate (0.80 g), 1,2-dimethoxyethane (9.6 mL), and water (3.2 mL) was stirred with heating under reflux for 1 hour and 15 minutes. After cooling to room temperature, water was added to the reaction liquid which was then extracted with ethyl acetate. The organic layer was washed with a saturated aqueous sodium chloride solution and dried over magnesium sulfate. The solvent was distilled off under reduced pressure, and the obtained residue was purified by silica gel column chromatography (hexane: ethyl acetate gradient elution=90:10 to 80:20) to obtain 4-(5-fluoro-3-nitro-2-(2,2,2-trifluoroethoxy)phenyl)-3,6-dihydro-2H-pyran (0.35 g) as a light brown solid.

1H-NMR (CDCl3) δ: 7.50 (dd, 1H, J=7.3, 3.3 Hz), 7.20 (dd, 1H, J=7.9, 3.3 Hz), 6.10-6.06 (m, 1H), 4.37-4.29 (m, 4H), 3.93 (t, 2H, J=5.3 Hz), 2.51-2.44 (m, 2H).

Reference Example 2-16

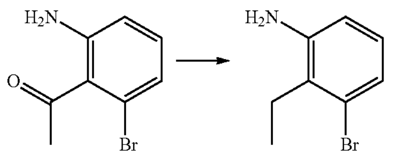

A mixture of 1-(2-amino-6-bromophenyl)ethan-1-one (0.15 g), hydrazine monohydrate (0.18 g), and diethylene glycol (3.0 mL) was stirred at 100° C. for 2 hours. After cooling to room temperature, a 50% aqueous potassium hydroxide solution (0.16 g) was added thereto, followed by stirring at 180° C. for 3 hours. After cooling to room temperature, water was added to the reaction liquid which was then extracted with toluene. The organic layer was washed twice with water, washed with an aqueous sodium chloride solution, and dried over magnesium sulfate. The solvent was distilled off under reduced pressure, and the obtained residue was purified by silica gel column chromatography (hexane:ethyl acetate gradient elution=100:0 to 80:20) to obtain 3-bromo-2-ethylaniline (0.12 g) as a colorless oil.

LCMS (Method A)

MS (ESI m/z): 200 (M+H)

RT (min): 1.39

Reference Example 2-17

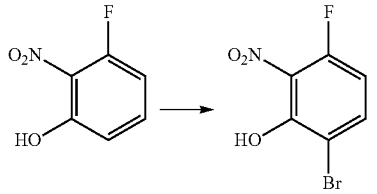 [SMILES: O=[N+]([O-])c1c(O)cccc1F ; O=[N+]([O-])c1c(F)ccc(Br)c1O]

Under ice cooling, N-bromosuccinimide (1.1 g) was added to a mixture of 3-fluoro-2-nitrophenol (1.0 g) and dichloromethane (10 mL) which was then stirred for 15 minutes. After stirring at room temperature for 20 minutes, acetic acid (10 mL) was added to the mixture which was then stirred for 1 hour and 40 minutes. After stirring at 50° C. for 1 hour and 40 minutes, N-bromosuccinimide (340 mg) was added to the mixture which was then stirred for 10 minutes. After cooling to room temperature, an aqueous sodium sulfite solution was added to the mixture which was then extracted twice with ethyl acetate. The solvent of the organic layer was distilled off under reduced pressure, and the obtained residue was purified by silica gel column chromatography (hexane:ethyl acetate gradient elution=100:0 to 40:60) to obtain 6-bromo fluoro-2-nitrophenol (300 mg) as a brown solid.

1H-NMR (CDCl3) δ: 10.87-10.51 (m, 1H), 7.78 (dd, 1H, J=8.6, 5.3 Hz), 6.77 (dd, 1H, J=10.9, 8.9 Hz).

LCMS (Method A)

MS (ESI m/z): 235 (M−H)

RT (min): 1.24

Reference Example 2-18

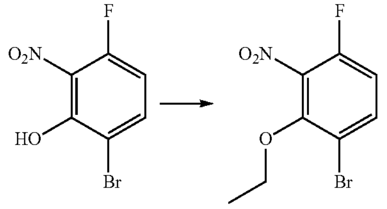

A mixture of 6-bromo-3-fluoro-2-nitrophenol (270 mg), iodoethane (270 μL), potassium carbonate (318 mg), and N,N-dimethylformamide (3.0 mL) was irradiated with microwaves (microwave reactor, 90° C., 30 minutes, 2.45 GHz, 0 to 240 W). Iodoethane (180 μL) was added to the reaction liquid which was then irradiated with microwaves (microwave reactor, 100° C., 30 minutes, 2.45 GHz, 0 to 240 W). Water was added to the reaction liquid which was then extracted twice with ethyl acetate. The solvent of the organic layer was distilled off under reduced pressure, and the obtained residue was purified by silica gel column chromatography to obtain 1-bromo-2-ethoxy-4-fluoro-3-nitrobenzene (0.13 g) as a yellow oil.

1H-NMR (CDCl3) δ: 7.66 (dd, 1H, J=8.9, 5.9 Hz), 6.95 (t, 1H, J=8.9 Hz), 4.28-4.19 (m, 2H), 1.46-1.40 (m, 3H).

Reference Example 2-19

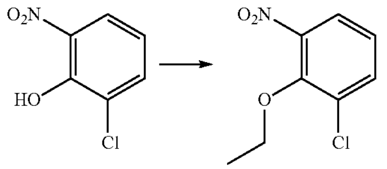

1-Chloro-2-ethoxy-3-nitrobenzene was obtained in the same manner as in Reference Example 2-18.

1H-NMR (DMSO-D6) δ: 7.92 (dd, 1H, J=8.0, 1.6 Hz), 7.88 (dd, 1H, J=8.0, 1.6 Hz), 7.38 (t, 1H, J=8.0 Hz), 4.16 (q, 2H, J=7.2 Hz), 1.35 (t, 3H, J=7.2 Hz).

Reference Example 2-20

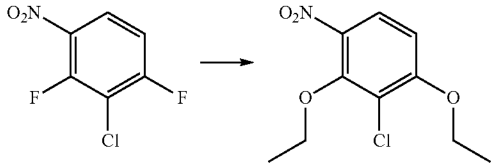 [SMILES: O=[N+]([O-])c1ccc(F)c(Cl)c1F ; CCOc1ccc([N+](=O)[O-])c(OCC)c1Cl]

A 20% sodium ethoxide-ethanol solution (270 g) was added dropwise over 20 minutes to a mixture of 2-chloro-1,3-difluoro-4-nitrobenzene (50 g) and ethanol (510 mL) under ice cooling. After stirring at 50° C. for 20 minutes, the mixture was ice-cooled and water (2.5 L) was added thereto. The precipitated solid was collected by filtration and dried to obtain 2-chloro-1,3-diethoxy-4-nitrobenzene (63 g) as a white solid.

1H-NMR (CDCl3) δ: 7.88 (d, 1H, J=9.2 Hz), 6.74 (d, 1H, J=9.2 Hz), 4.21 (q, 2H, J=7.2 Hz), 4.20 (q, 2H, J=6.8 Hz), 1.52 (t, 3H, J=7.2 Hz), 1.49 (t, 3H, J=6.8 Hz).

Reference Example 2-21

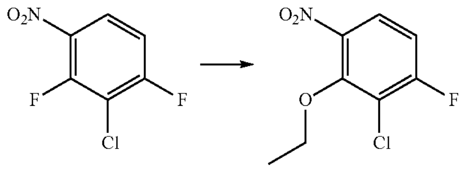

A 20% sodium ethoxide-ethanol solution (1.8 g) was added dropwise to a mixture of 2-chloro-1,3-difluoro-4-nitrobenzene (1.0 g) and ethanol (15 mL) under ice cooling. After stirring at room temperature for 1 hour, water was added to the mixture which was then extracted with ethyl acetate. The organic layer was washed with an aqueous sodium chloride solution and dried over sodium sulfate. The solvent was distilled off under reduced pressure, and the obtained residue was purified by silica gel column chromatography (hexane:ethyl acetate gradient elution=100:0 to 95:5) to obtain 2-chloro-3-ethoxy-1-fluoro-4-nitrobenzene (0.50 g) as a pale yellow oil.

1H-NMR (CDCl3) δ: 7.82 (dd, 1H, J=9.2, 5.6 Hz), 7.05 (dd, 1H, J=9.2, 7.2 Hz), 4.26 (q, 2H, J=7.2 Hz), 1.49 (t, 3H, J=7.2 Hz).

Reference Example 2-22

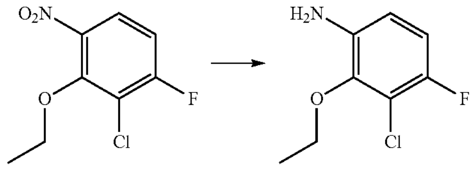

3-Chloro-2-ethoxy-4-fluoroaniline was obtained in the same manner as in Reference Example 2-3.

1H-NMR (CDCl3) δ: 6.75 (t, 1H, J=8.8 Hz), 6.58 (dd, 1H, J=8.8, 5.4 Hz), 4.07 (q, 2H, J=7.2 Hz), 3.74 (br s, 2H), 1.44 (t, 3H).

Reference Example 3

Compound C was obtained from Compound A and Compound B in the same manner as in Reference Example 2-2. In Reference Examples 3-3 and 3-6, the reaction temperature was changed to 70° C. In addition, one equal amount of (S)-1,1,1-trifluoropropan-2-ol was used in Reference Example 3-6.

TABLE 1

| Reference Example No. | A | B | C | LCMS Meth-od | LCMS RT (min) | LCMS Ms (M + H) | NMR |
|---|---|---|---|---|---|---|---|
| 3-1 | 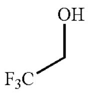 | 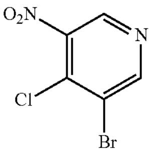 | 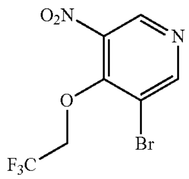 | A | 1.37 | 301 | — |
| 3-2 | 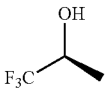 | 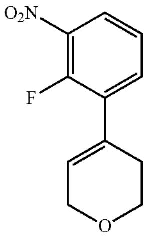 | 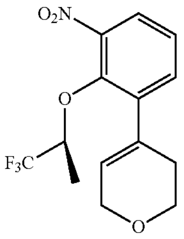 | — | — | — | 1H-NMR (CDCl3) δ: 7.73 (dd, 1H, J = 7.9, 1.3 Hz), 7.42 (dd, 1H, J = 7.6, 1.7 Hz), 7.24 (dd, 1H, J = 7.9, 7.6 Hz), 6.00-5.96 (m, 1H), 4.56-4.42 (m. 1H), 4.35-4.29 (m, 2H), 3.92 (t, 2H, J = 5.3 Hz), 2.61-2.37 (m, 2H), 1.42 (d, 2H, J = 6.6 Hz). |
| 3-3 | 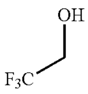 | 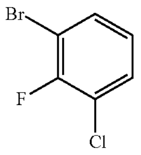 | 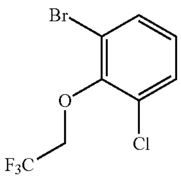 | — | — | — | 1H-NMR (CDCl3) δ: 7.49 (dd, 1H, J = 7.9. 1.3 Hz), 7.37 (dd, 1H, J = 7.9, 1.3 Hz), 7.01 (t, 1H, J = 7.9 H), 4.41 (q, 2H, J = 8.1 Hz). |
| 3-4 | 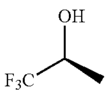 | 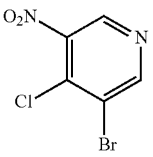 | 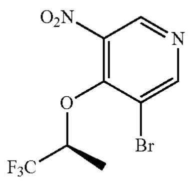 | A | 1.45 | 315 | — |
| 3-5 | 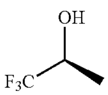 | 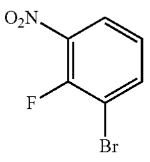 | 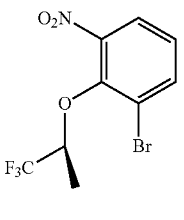 | — | — | — | 1H-NMR (CDCl3) δ: 7.84-7.79 (m, 2H), 7.17 (t, 1H, J = 7.9 Hz), 4.74-4.66 (m, 1H), 1.58 (d, 3H, J = 6.6 Hz). |

TABLE 1-continued

| Reference Example No. | A | B | C | LCMS Meth-od | LCMS RT (min) | LCMS Ms (M + H) | NMR |
|---|---|---|---|---|---|---|---|
| 3-6 | 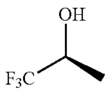 | 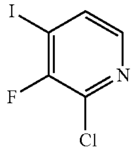 | 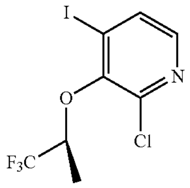 | A | 1.61 | 352 | — |

Reference Example 4

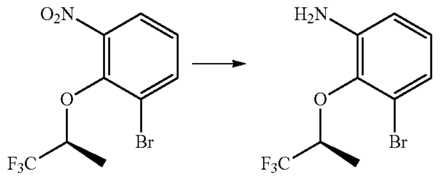 [SMILES: C[C@H](Oc1c(Br)cccc1[N+](=O)[O-])C(F)(F)F ; C[C@H](Oc1c(N)cccc1Br)C(F)(F)F]

(S)-3-bromo-2-((1,1,1-trifluoropropan-2-yl)oxy) aniline was obtained in the same manner as in Reference Example 2-3.

LCMS (Method A)

MS (ESI m/z): 283 (M+H)

RT (min): 1.61

Reference Example 5

Compound C was obtained from Compound A and Compound B in the same manner as in Reference Example 2-1.

TABLE 2

| Reference Example No. | A | B | C | LCMS Method | LCMS RT (min) | LCMS MS (M + H) | NMR |
|---|---|---|---|---|---|---|---|
| 5-1 | 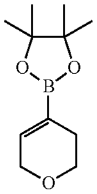 | 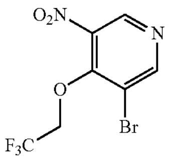 | 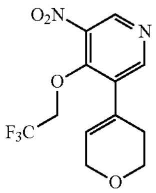 | A | 1.28 | 3.05 | — |
| 5-2 | 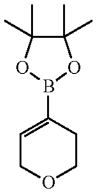 | 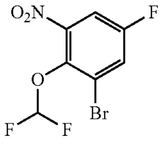 | 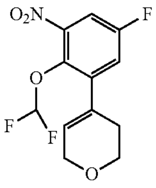 | — | — | — | 1H-NMR (CDCl3) δ: 7.54 (dd, 1H, J = 7.1. 3.1 Hz), 7.24 (dd, 1H, J = 8.1, 3.1 Hz), 6.50 (t, 1H, J = 73.4 Hz), 6.00-5.98 (m, 1H), 4.34-4.30 (m, 2H), 3.91 (t, 2H, J = 5.4 Hz), 2.50-2.44 (m, 2H). |

TABLE 2-continued
| Reference Example No. | A | B | C | LCMS Method | LCMS RT (min) | LCMS MS (M + H) | NMR |
|---|---|---|---|---|---|---|---|
| 5-3 | 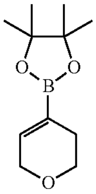 | 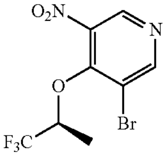 | 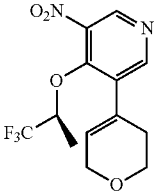 | A | 1.35 | 319 | — |
| 5-4 | 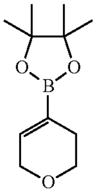 | 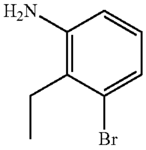 | 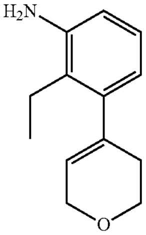 | A | 0.87 | 204 | — |
| 5-5 | 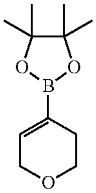 | 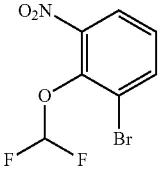 | 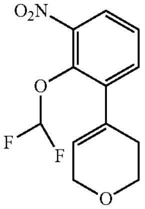 | — | — | — | 1H-NMR (DMSO-D6) δ: 7.96 (dd, 1H, J = 7.9, 1.3 Hz), 7.69 (dd, 1H, J = 7.6, 1.7 Hz), 7.55 (t, 1H, J = 7.9 Hz), 7.04 (t, 1H, J = 72.3 Hz), 6.02 (s, 1H), 4.23-4.18 (m, 2H), 3.80 (t, 2H, J = 5.6 Hz), 2.43-2.35 (m, 2H). |
| 5-6 | 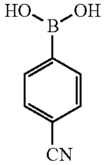 | 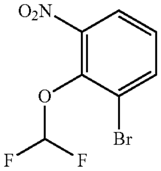 | 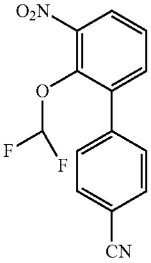 | — | — | — | 1H-NMR (DMSO-D6) δ: 8.16 (dd, 1H, J = 7.9, 1.3 Hz), 8.02-7.96 (m, 2H), 7.91-7.86 (m, 1H), 7.77-7.67 (m, 3H), 6.90 (t, 1H, J = 72.0 Hz), |
| 5-7 | 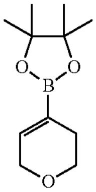 | 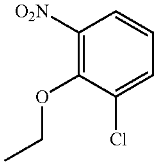 | 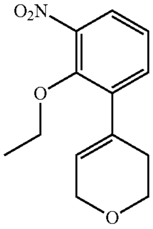 | — | — | — | 1H-NMR (CDCl3) δ: 7.65 (dd, 1H, J = 8.0, 1.6 Hz), 7.38 (dd, 1H, J = 7.6, 1.6 Hz), 7.16 (t, 1H J = 8.0 Hz), 5.98-5.96 (m, 1H), 4.33 (q, 2H, J = 2.8 Hz), 4.04 (q, 2H, J = 7.2 Hz), 3.92 (t, 2H, J = 5.2 Hz), 2.55-2.50 (m, 2H), 1.36 (t, 3H, J = 7.2 Hz). |
| 5-8 | 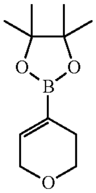 | 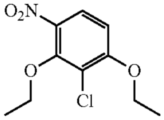 | 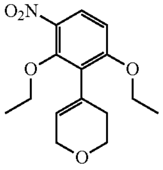 | — | — | — | 1H-NMR (CDCl3) δ: 7.85 (d, 1H, J = 9.2 Hz), 6.66 (d, 1H, J = 9.2 Hz), 5.75-5.73 (m, 1H), 4.32 (q, 2H, J = 2.8 Hz), 4.09 (q, 2H, J = 6.8 Hz), 4.01 (q, 2H, J = 6.8 Hz), 3.92 (t, 2H, J = 5.6 Hz), 2.36-2.04 (m, 2H), 1.43 (t, 3H, J = 6.8 Hz), 1.38 (t, 3H, J = 6.8 Hz). |

TABLE 2-continued

| Reference Example No. | A | B | C | LCMS Method | LCMS RT (min) | LCMS MS (M + H) | NMR |
|---|---|---|---|---|---|---|---|
| 5-9 | 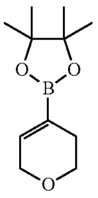 | 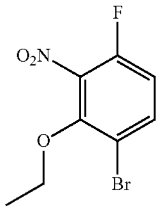 | 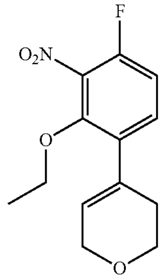 | — | — | — | 1H-NMR (CDCl3) δ: 7.30-7.23 (m, 1H), 6.96 (t, 1H, J = 8.9 Hz), 5.97 (br, s, 1H) 4.33-4.29 (m, 2H), 4.05 (q, 2H, J = 6.9 Hz), 3.91 (t, 2H, J = 5.3 Hz), 2.52-2.44 (m, 2H), 1.32 (t, 3H, J = 6.9 Hz). |
| 5-10 | 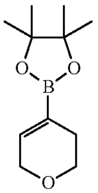 | 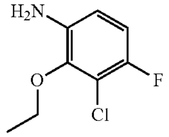 | 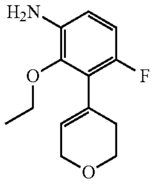 | — | — | — | 1H-NMR (CDCl3) δ: 6.67 (t, 1H, J = 8.8 Hz), 6.59 (dd, 1H, J = 8.8, 5.6 Hz), 5.84-5.83 (m, 1H), 4.32 (q, 2H, J = 2.8 Hz), 3.93 (t, 2H, J = 5.2 Hz), 3.90 (q, 2H, J = 7.2 Hz), 3.67 (br s, 2H), 2.46-2.43 (m, 2H), 1.35 (t, 3H, J = 7.2 Hz). |
| 5-11 | 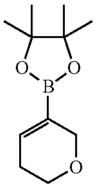 | 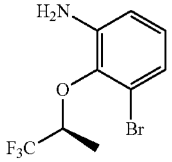 | 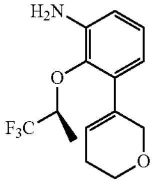 | A | 1.48 | 2.88 | — |

Reference Example 6

Compound B was obtained from Compound A in the same manner as in Reference Example 2-3.

TABLE 3

| Reference Example No. | A | B | LCMS Method | LCMS RT (min) | LCMS MS (M + H) | NMR |
|---|---|---|---|---|---|---|
| 6-1 | 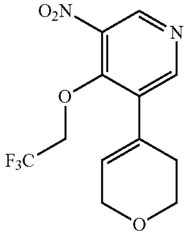 | 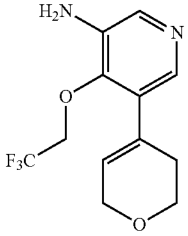 | A | 0.67 | 275 | — |
| 6-2 | 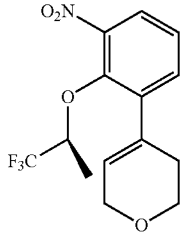 | 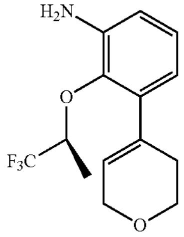 | A | 1.43 | 288 | — |

TABLE 3-continued
| Reference Example No. | A | B | LCMS Method | LCMS RT (min) | LCMS MS (M + H) | NMR |
|---|---|---|---|---|---|---|
| 6-3 | 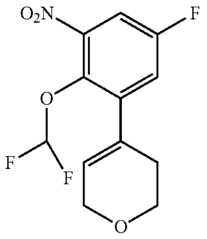 | 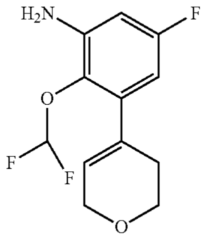 | A | 1.31 | 260 | — |
| 6-4 | 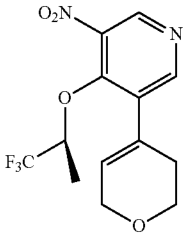 | 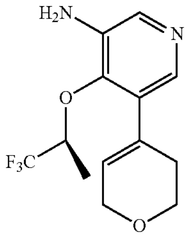 | A | 0.72 | 289 | — |
| 6-5 | 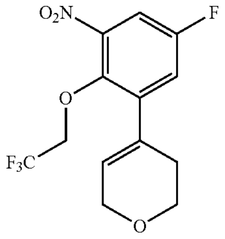 | 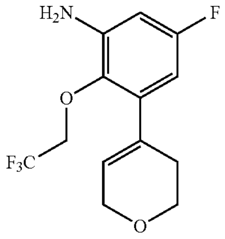 | A | 1.44 | 292 | — |
| 6-6 | 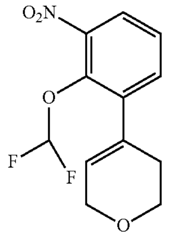 | 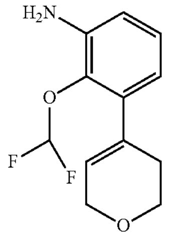 | A | 1.21 | 242 | — |
| 6-7 | 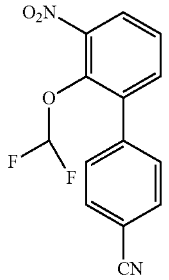 | 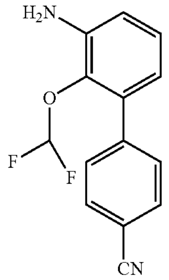 | A | 1.39 | 261 | — |
| 6-8 | 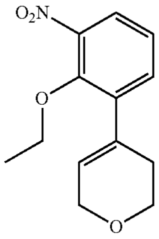 | 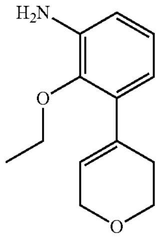 | — | — | — | 1H-NMR (DMSO-D6) δ: 6.75 (t, 1H, J = 7.6 Hz), 6.60 (dd, 1H, J = 8.0, 1.6 Hz), 6.34 (dd, 1H, J = 7.6, 1.6 Hz), 5.86-5.84 (m, 1H), 4.82 (s, 2H), 4.18 (q, 2H, J = 2.8 Hz), 3.78 (t, 2H, J = 5.6 Hz), 3.73 (q, 2H, J = 6.8 Hz), 2.41-2.38 (m, 2H), 1.26 (t, 3H, J = 6.8 Hz). |

TABLE 3-continued
| Reference Example No. | A | B | LCMS Method | LCMS RT (min) | LCMS MS (M + H) | NMR |
|---|---|---|---|---|---|---|
| 6-9 | 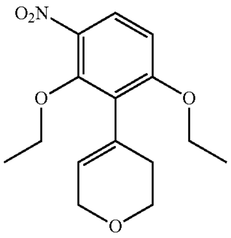 | 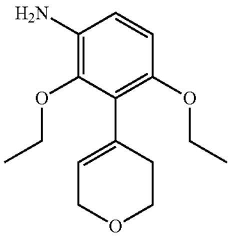 | — | — | — | 1H-NMR (CDCl3) δ: 6.61 (d 1H, J = 8.4 Hz), 6.52 (d, 1H, J = 8.8 Hz), 5.74-5.72 (m, 1 H), 4.32 (q, 2H, J = 2.8 Hz), 3.93-3.85 (m, 6H), 3.58 (br s, 2H) 2.47-2.42 (m, 2H), 1.34 (q, 6H, J = 7.2 Hz). |
| 6-10 | 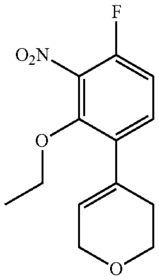 | 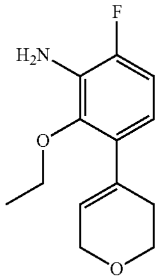 | A | 1.30 | 2.38 | — |
Reference Example 7
Compound B was obtained from Compound A in the same manner as in Reference Example 2-8.
TABLE 4
| Reference Example No. | A | B | LCMS Method | LCMS RT (min) | LCMS MS (M + H) | NMR |
|---|---|---|---|---|---|---|
| 7-1 | 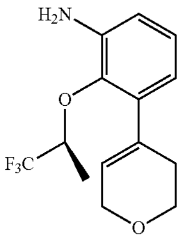 | 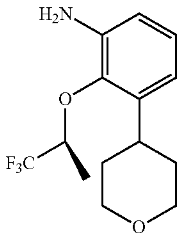 | A | 1.42 | 290 | — |
| 7-2 | 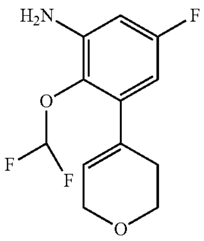 | 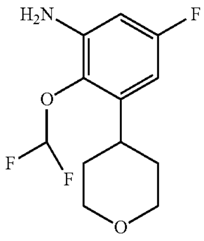 | A | 1.28 | 262 | — |

TABLE 4-continued
| Reference Example No. | A | B | LCMS Method | LCMS RT (min) | LCMS MS (M + H) | NMR |
|---|---|---|---|---|---|---|
| 7-3 | 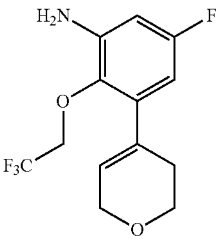 | 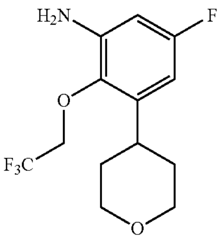 | A | 1.41 | 294 | — |
| 7-4 | 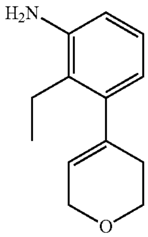 | 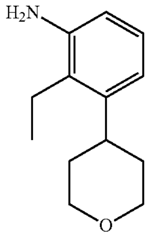 | A | 0.72 | 206 | — |
| 7-5 | 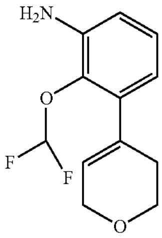 | 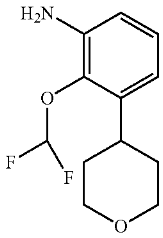 | A | 1.18 | 244 | — |
Reference Example 8
Compound C was obtained from Compound A and Compound B in the same manner as in Reference Example 2-4.

TABLE 5-2
| Reference Example No. | A | B | C | LCMS Meth-od | LCMS RT (Min) | LCMS MS (M + H) | NMR |
|---|---|---|---|---|---|---|---|
| 8-1 | 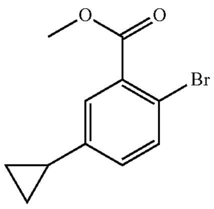 | 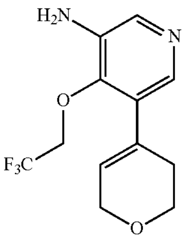 | 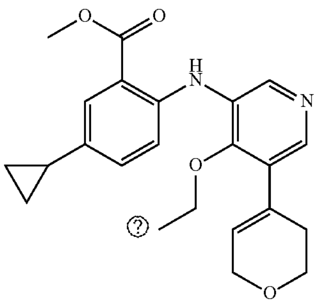 | A | 1.59 | 449 | — |
| 8-2 | 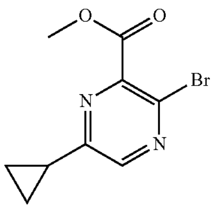 | 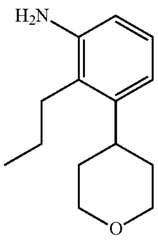 | 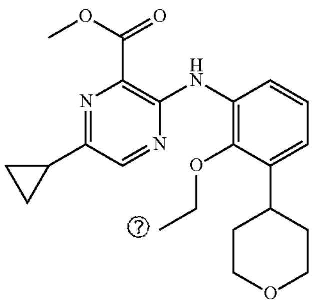 | A | 1.93 | 396 | — |
| 8-3 | 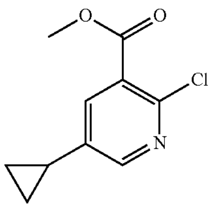 | 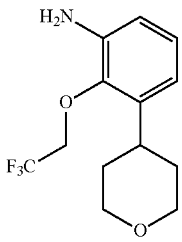 | 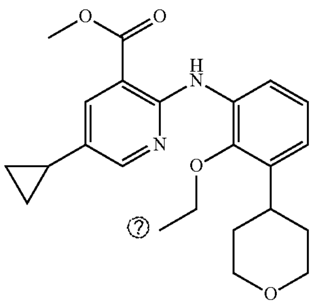 | A | 2.03 | 451 | — |

TABLE 5-2-continued
| Reference Example No. | A | B | C | LCMS Meth-od | LCMS RT (Min) | LCMS MS (M + H) | NMR |
|---|---|---|---|---|---|---|---|
| 8-4 | 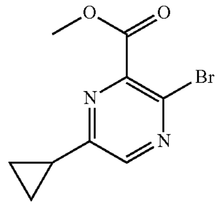 | 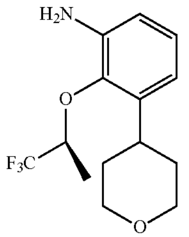 | 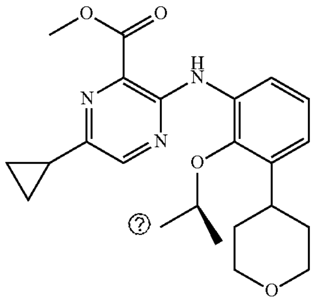 | A | 1.91 | 466 | — |
| 8-5 | 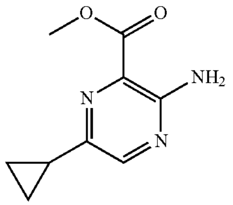 | 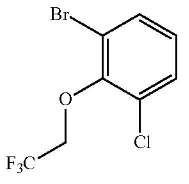 | 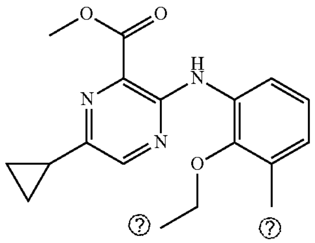 | A | 1.97 | 402 | — |
| 8-6 | 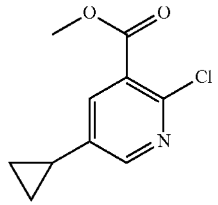 | 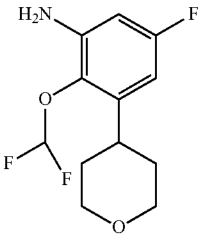 | 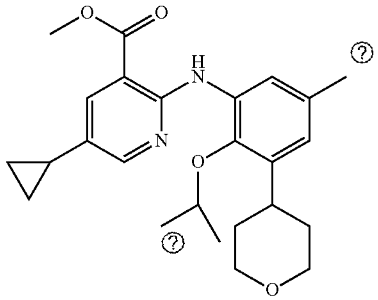 | A | 2.03 | 437 | — |

TABLE 5-2-continued
| Reference Example No. | A | B | C | LCMS Meth-od | LCMS RT (Min) | LCMS MS (M + H) | NMR |
|---|---|---|---|---|---|---|---|
| 8-7 | 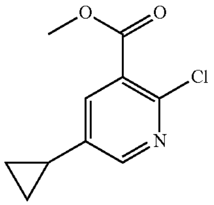 | 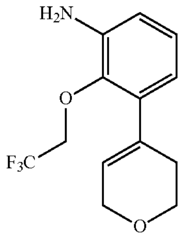 | 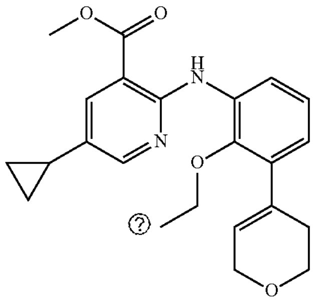 | A | 1.91 | 449 | — |
| 8-8 | 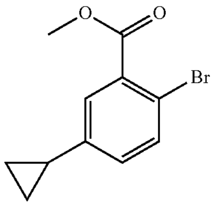 | 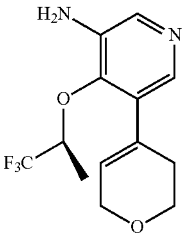 | 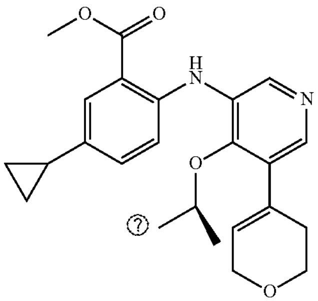 | A | 1.67 | 463 | — |
| 8-9 | 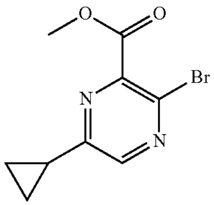 | 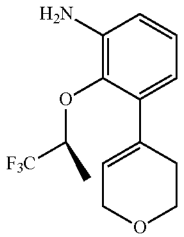 | 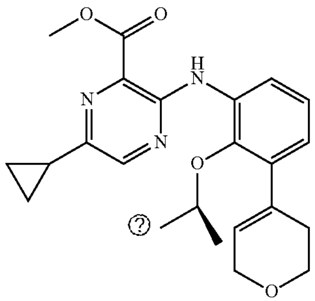 | A | 1.95 | 464 | — |

TABLE 5-2-continued
| Reference Example No. | A | B | C | LCMS Meth-od | LCMS RT (Min) | LCMS MS (M + H) | NMR |
|---|---|---|---|---|---|---|---|
| 8-10 | 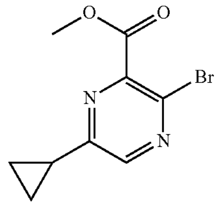 | 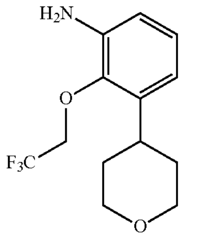 | 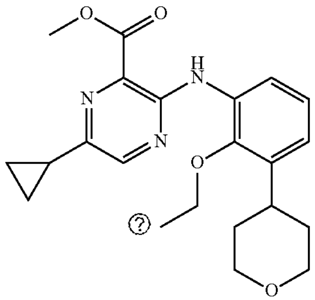 | A | 1.88 | 452 | — |
| 8-11 | 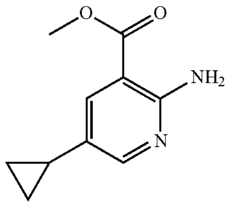 | 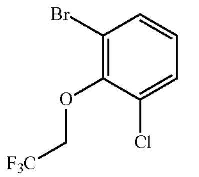 | 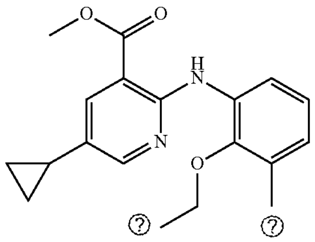 | A | 2.12 | 401 | — |
| 8-12 | 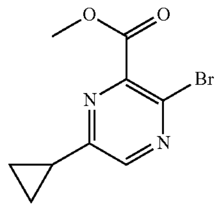 | 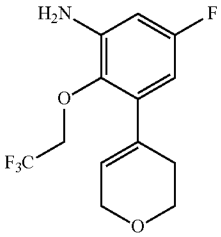 | 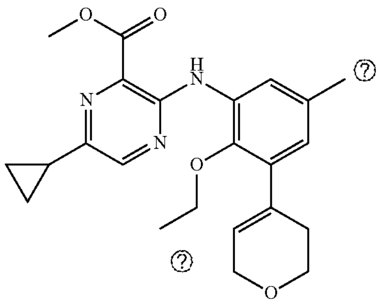 | A | 1.99 | 468 | — |

TABLE 5-2-continued
| Reference Example No. | A | B | C | LCMS Meth-od | LCMS RT (Min) | LCMS MS (M + H) | NMR |
|---|---|---|---|---|---|---|---|
| 8-13 | 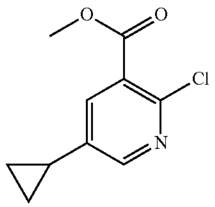 | 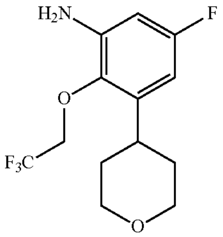 | 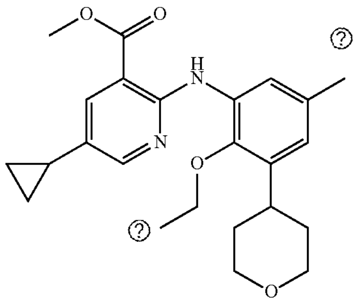 | A | 2.11 | 469 | — |
| 8-14 | 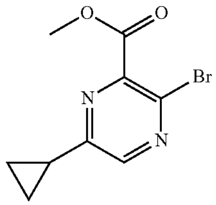 | 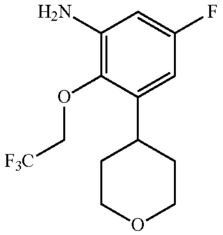 | 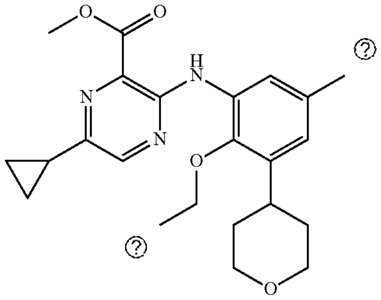 | A | 1.93 | 470 | — |
| 8-15 | 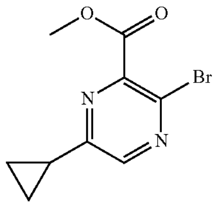 | 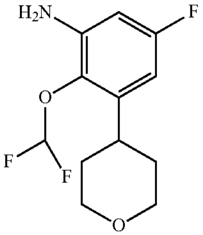 | 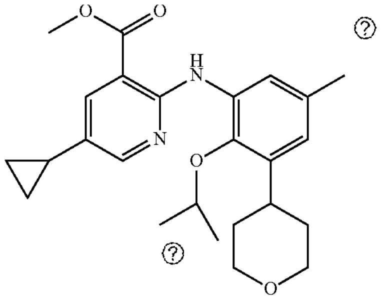 | A | 1.87 | 438 | — |

TABLE 5-2-continued
| Reference Example No. | A | B | C | LCMS Meth-od | LCMS RT (Min) | LCMS MS (M + H) | NMR |
|---|---|---|---|---|---|---|---|
| 8-16 | 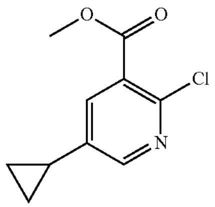 | 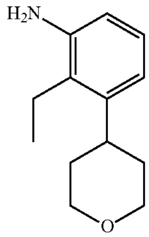 | 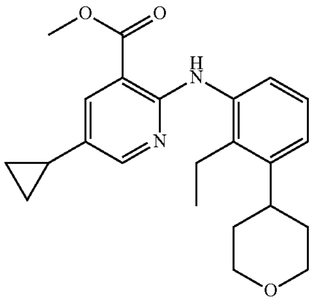 | A | 1.86 | 381 | — |
| 8-17 | 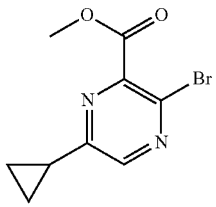 | 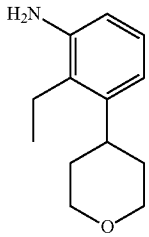 | 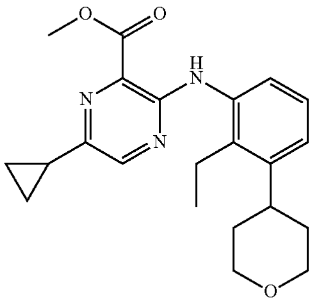 | A | 1.82 | 382 | — |
| 8-18 | 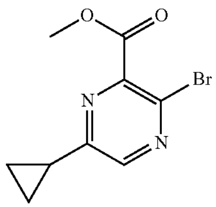 | 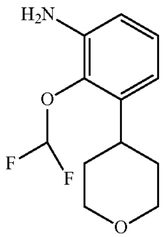 | 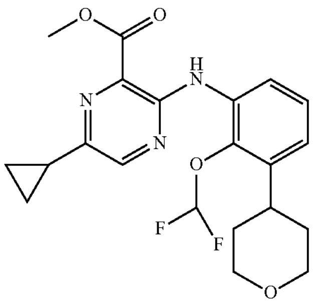 | A | 1.76 | 420 | — |

TABLE 5-2-continued
| Reference Example No. | A | B | C | LCMS Meth-od | LCMS RT (Min) | LCMS MS (M + H) | NMR |
|---|---|---|---|---|---|---|---|
| 8-19 | 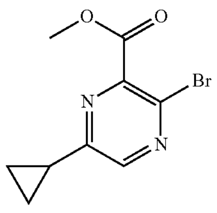 | 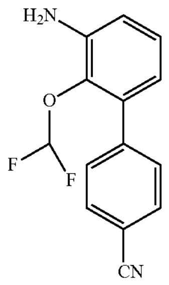 | 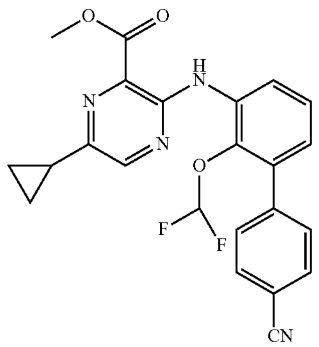 | A | 1.88 | 437 | — |
| 8-20 | 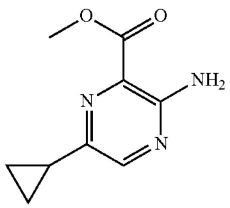 | 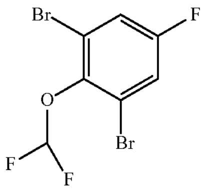 | 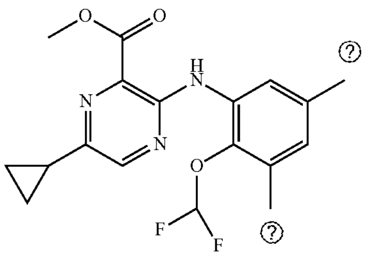 | A | 1.96 | 431 | — |
| 8-21 | 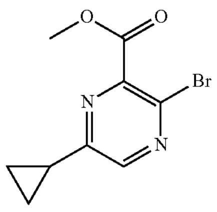 | 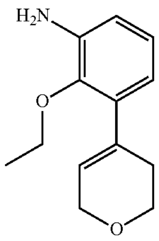 | 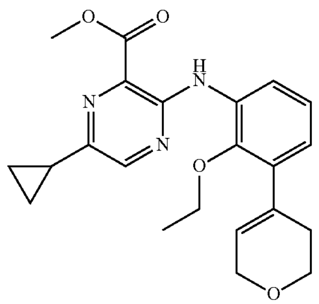 | B | 5.17 | 396 | 1H-NMR (CDCl3) δ: 10.69 (br s, 1H), 8.47 (dd, 1H, J = 8.2, 1.6 Hz), 8.21 (s, 1H), 7.08 t, 1H, J = 8.0 Hz), 6.85 (dd, 1H, J = 7.6, 1.6 Hz), 5.97-5.96 (m, 1H), 4.33 (q, 2H, J = 2.8 Hz), 4.01 (s, 3H), 3.95 (q, 2H, J = 7.2 Hz), (t, 2H, J = 5.6 Hz), 2.59-2.56 (m, 2H), 2.12-2.06 (m, 1H), 1.46 (t, 3H, J = 7.2 Hz), 1.04-0.94 (m, 4H). |

TABLE 5-2-continued
| Reference Example No. | A | B | C | LCMS Meth-od | LCMS RT (Min) | LCMS MS (M + H) | NMR |
|---|---|---|---|---|---|---|---|
| 8-22 | 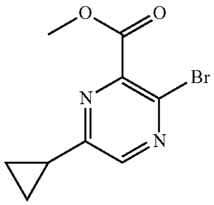 | 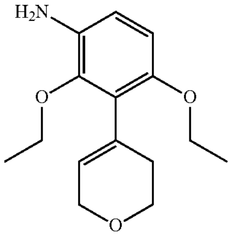 | 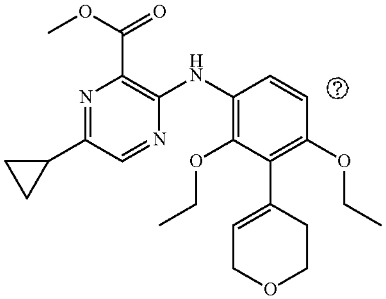 | B | 5.27 | 440 | 1H-NMR (CDCl3) δ: 10.39 (br s, 1H), 8.25 (d, 1H, J = 8.8 Hz), 8.16 (s, 1H), 6.66 (d, 1H, J = 9.2 Hz), 5.80-5.78 (m, 1H), 4.33 (q, 2H, J = 2.4 Hz), 4.00 (q, 2H, J = 6.8 Hz), 4.00 (s, 3H), 3.93 (q, 2H, J = 6.8 Hz), 3.93 (t, 2H, J = 5.6 Hz), 2.49-2.47 (m, 2H), 2.11-2.04 (m, 1H), 1.42 (t, 3H, J = 6.8 Hz), 1.38 (t, 3H, J = 6.8 Hz), 1.03-0.92 (m, 4H). |
| 8-23 | 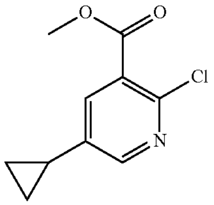 | 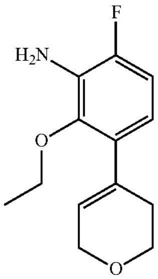 | 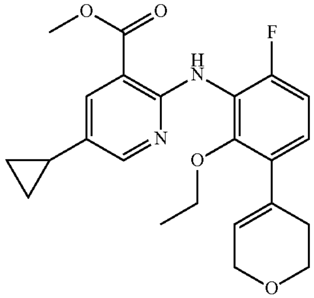 | A | 1.85 | 413 | — |
| 8-24 | 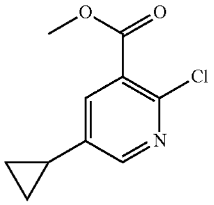 | 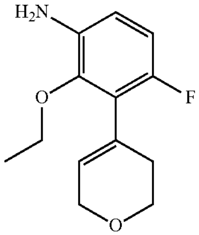 | 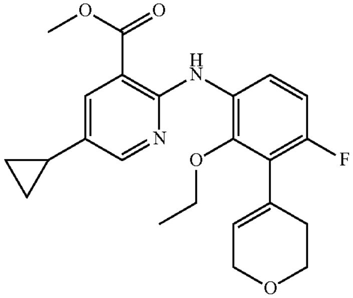 | A | 2.14 | 413 | — |

TABLE 5-2-continued
| Reference Example No. | A | B | C | LCMS Method | LCMS RT (Min) | LCMS MS (M + H) | NMR |
|---|---|---|---|---|---|---|---|
| 8-25 | 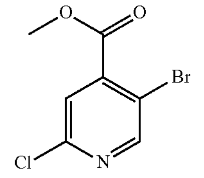 | 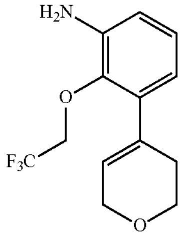 | 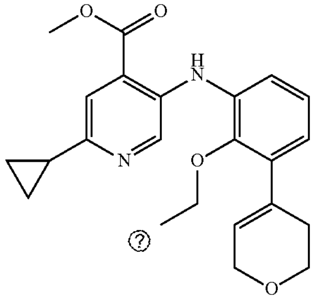 | A | 1.84 | 443 | — |
| 8-26 | 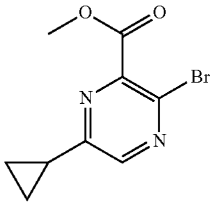 | 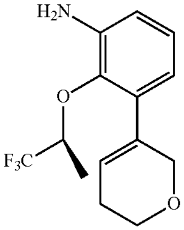 | 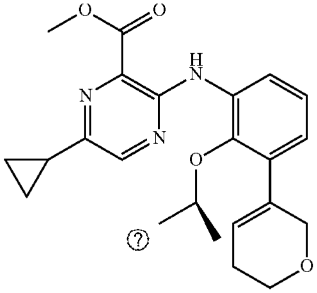 | A | 2.00 | 464 | — |
| 8-27 | 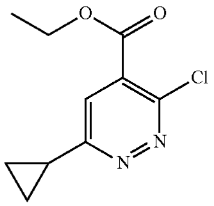 | 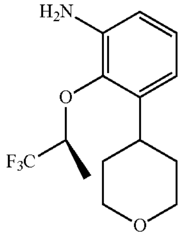 | 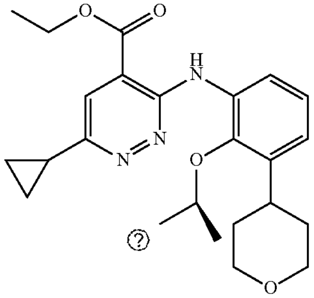 | A | 1.86 | 480 | — |

TABLE 5-2-continued
| Reference Example No. | A | B | C | LCMS Meth-od | LCMS RT (Min) | LCMS MS (M + H) | NMR |
|---|---|---|---|---|---|---|---|
| 8-28 | 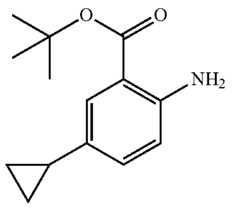 | 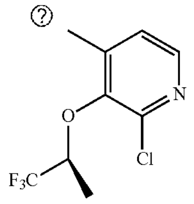 | 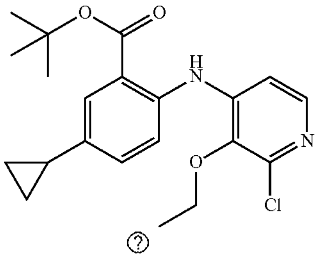 | A | 2.22 | 457 | — |
| 8-29 | 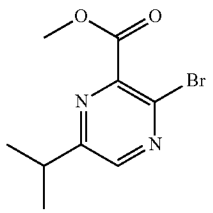 | 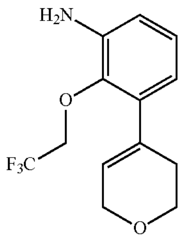 | 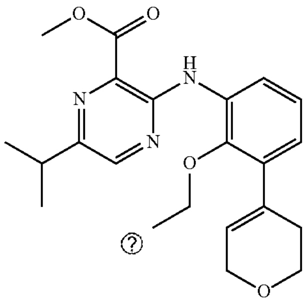 | A | 1.93 | 452 | — |

TABLE 5-2-continued
| Reference Example No. | A | B | C | LCMS Meth-od | LCMS RT (Min) | LCMS MS (M + H) | NMR |
|---|---|---|---|---|---|---|---|
| 8-30 | 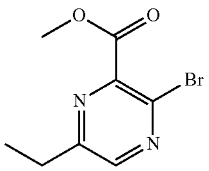 | 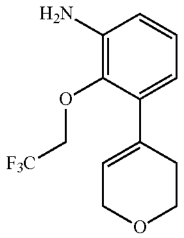 | 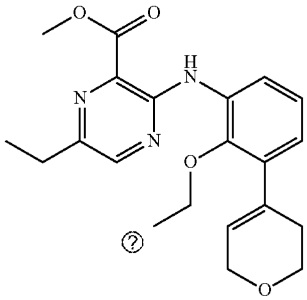 | A | 1.78 | 438 | — |
| 8-31 | 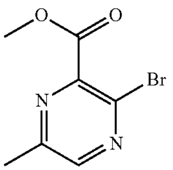 | 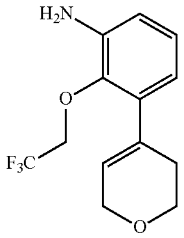 | 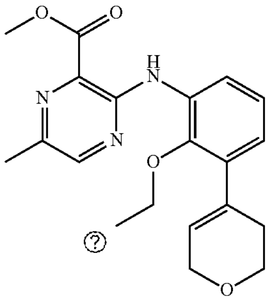 | A | 1.64 | 424 | — |

Reference Example 9
Compound C was obtained from Compound A and Compound B by changing the reaction solvent from 1,2-dimethoxyethane to toluene and the reaction temperature to 140° C. in the method of Reference Example 2-1.
TABLE 6
| Reference Example No. | A | B | C | Method | LCMS RT (min) | LCMS MS (M + H) | NMR |
|---|---|---|---|---|---|---|---|
| 9-1 | 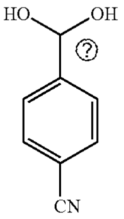 | 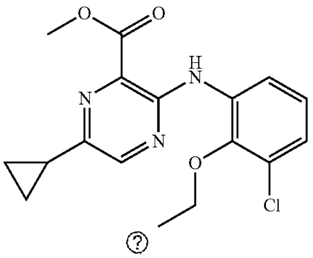 | 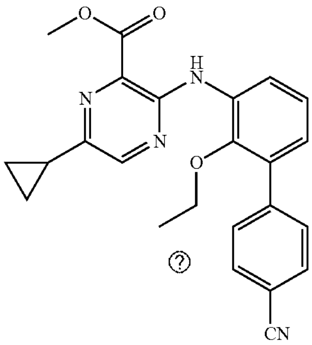 | A | 1.98 | 469 | — |
| 9-2 | 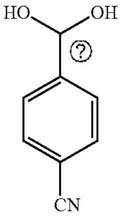 | 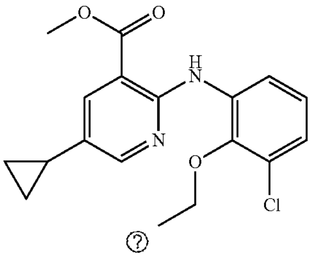 | 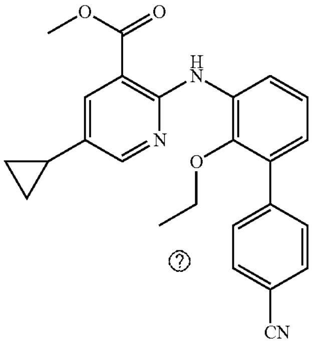 | A | 2.12 | 468 | — |
| 9-3 | 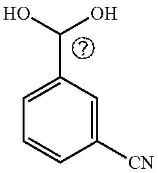 | 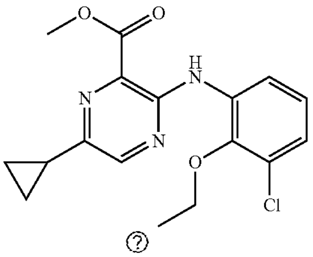 | 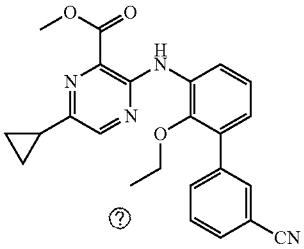 | A | 1.96 | 469 | — |
| 9-4 | 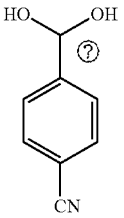 | 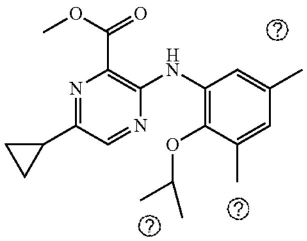 | 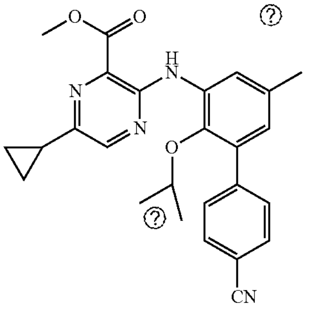 | A | 1.97 | 455 | — |

TABLE 6-continued
| Reference Example No. | A | B | C | LCMS Method | LCMS RT (min) | LCMS MS (M + H) | NMR |
|---|---|---|---|---|---|---|---|
| 9-5 | 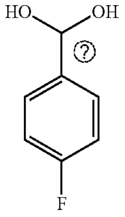 | 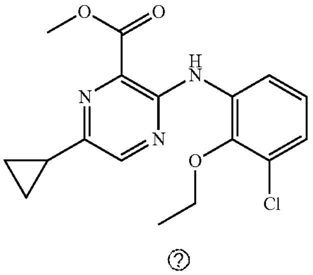 | 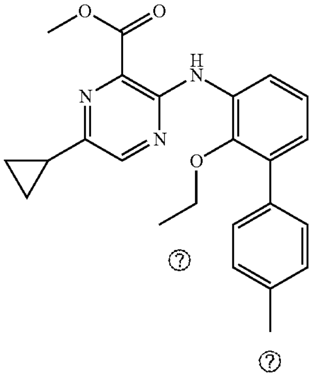 | A | 2.10 | 462 | — |
| 9-6 | 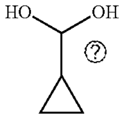 | 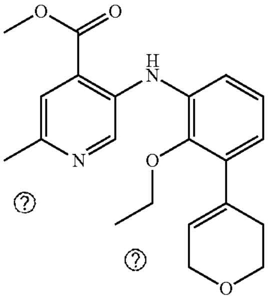 | 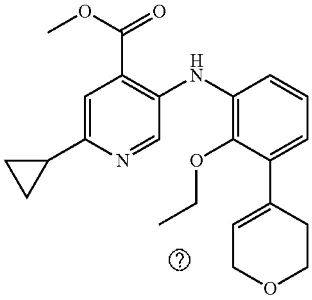 | A | 1.82 | 449 | — |
| 9-7 | 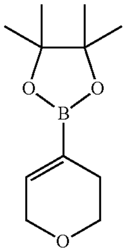 | 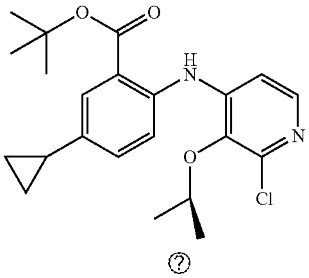 | 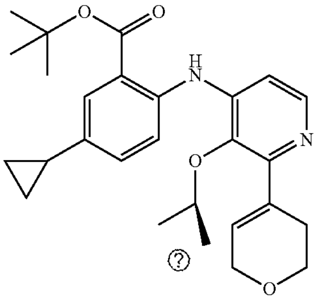 | A | 1.58 | 505 | — |
Reference Example 10
Compound B was obtained from Compound A in the same manner as in Reference Example 2-5.

TABLE 7
| Reference Example No. | A | B | LCMS Method | LCMS RT (min) | LCMS MS (M + H) | NMR |
|---|---|---|---|---|---|---|
| 10-1 | 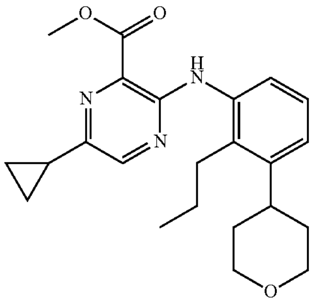 | 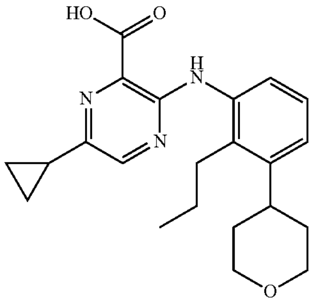 | A | 1.74 | 382 | 1H-NMR (CDCl3) δ: 9.70 (s, 1H), 8.31 (s, 1H), 7.65 (d, 1H, J = 7.9 Hz), 7.25-7.23 (m, 1H), 7.13 (d, 1H, J = 6.6 Hz), 4.10 (dd, 2H, J = 11.2, 4.0 Hz), 3.56 (t, 2H, J = 10.9 Hz), 3.08-2.96 (m, 1H), 2.71 (t, 2H, J = 8.3 Hz), 2.10-1.99 (m, 1H), 1.96-1.81 (m, 2H), 1.72-1.63 (m, 2H), 1.62-1.49 (m, 2H), 1.09-0.91 (m, 4H), 1.05 (t, 3H, J = 7.3 Hz). |
| 10-2 | 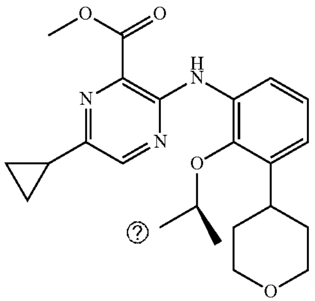 | 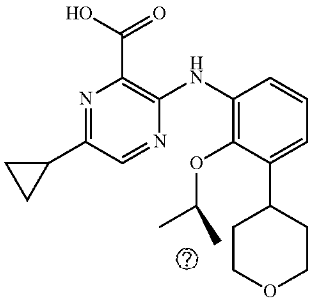 | A | 1.74 | 452 | 1H-NMR (DMSO-D6) δ: 13.45 (br s, 1H) 10.34 (br s, 1H), 8.38 (s, 1H), 8.12-8.07 (m, 1H), 7.20-7.12 (m, 1H), 7.06-7.00 (m, 1H), 4.78-4.68 (m, 1H), 4.04-3.92 (m, 2H), 3.47-3.36 (m, 2H), 3.22-3.10 (m, 1H), 2.20-2.09 (m, 1H), 1.79-1.56 (m, 4H), 1.30 (d, 3H, J = 6.6 Hz), 1.00-0.89 (m, 4H). |
| 10-3 | 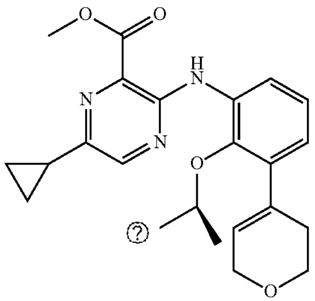 | 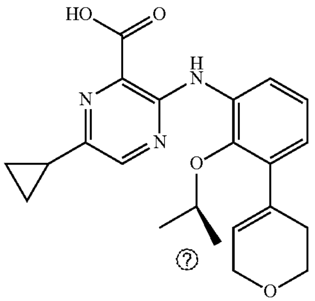 | A | 1.80 | 450 | 1H-NMR (DMSO-D6) δ: 13.45 (br s, 1H), 10.51 (br s, 1H), 8.42 (s, 1H), 8.34 (dd, 1H, J = 8.6, 1.3 Hz), 7.16 (dd, 1H, J = 7.9, 8.6 Hz), 6.91-6.88 (m, 1H), 5.96 (s, 1H), 4.73-4.57 (m, 1H), 4.23-4.16 (m, 2H), 3.82 (t, 2H, J = 5.3 Hz), 2.47-2.35 (m, 2H), 2.20-2.11 (m, 1H), 1.28 (d, 3H, J = 6.6 Hz), 1.01-0.90 (m, 4H). |

TABLE 7-continued
| Reference Example No. | A | B | LCMS Method | RT (min) | MS (M + H) | NMR |
|---|---|---|---|---|---|---|
| 10-4 | 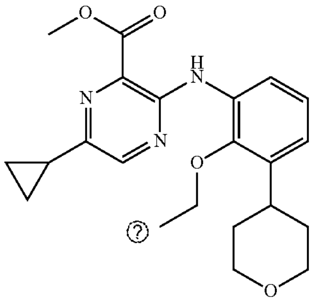 | 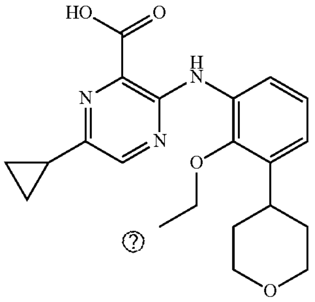 | A | 1.70 | 438 | 1H-NMr (DMSO-D6) δ: 13.46 (br s, 1H), 10.53 (br s, 1H), 8.41 (s, 1H), 8.27-8.20 (m, 1H), 7.22-7.13 (m, 1H), 7.04-6.97 (m, 1H), 453 (q, 2H, J = 9.0 Hz), 4.03-3.82 (m, 2H), 3.49-3.38 (m, 2H), 3.24-3.11 (m, 1H), 2.21-2.11 (m, 1H), 1.76-1.62 (m, 4H), 1.01-089 (m, 4H). |
| 10-5 | 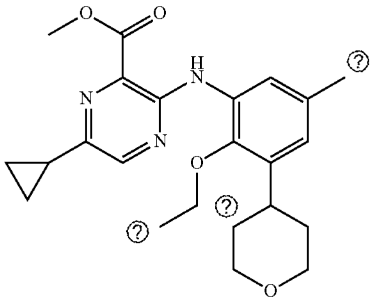 | 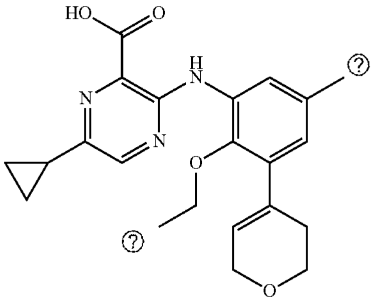 | A | 1.81 | 454 | 1H-NMR (CDCl3) δ: 10.49 (s, 1H),8.46 (s, 1H), 8.29 (dd, 1H, J = 10.9, 3.0 Hz), 6.61 (dd, 1H, J = 8.6, 3.3 Hz), 6.04 (s, 1H, 4.32 (d, 2H, J = 2.6 Hz), 4.22 (q, 2H, J = 8.4 Hz), 3.93 (t, 2H, J = 5.6 Hz), 2.50 (s, 2H), 2.20-2.03 (m, 1H), 1.15-0.96 (m, 4H). |
| 10-6 | 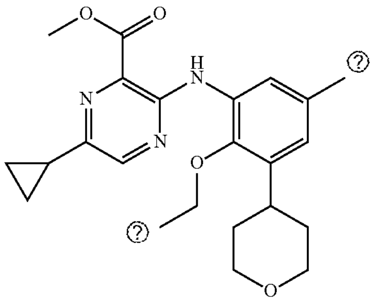 | 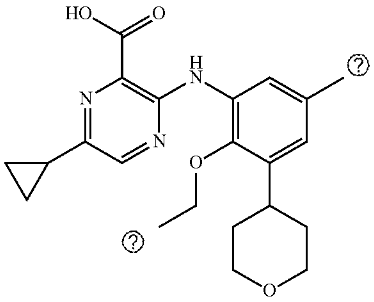 | A | 1.77 | 456 | 1H-NMR (MeOD) δ: 8.36 (s, 1H) 8.26 (dd, 1H, J = 10.9, 3.0 Hz), 6.69 (dd, 1H, J = 9.6, 3.0 Hz), 4.41 (q, 2H, J = 8.8 Hz), 4.06 (d, 2H, J = 11.2 Hz), 3.61-3.50 (m, 3H), 2.20-2.10 (m, 1H), 1.79-1.71 (m, 4H), 1.07-0.98 (m, 4H). |

TABLE 7-continued
| Reference Example No. | A | B | LCMS Method | LCMS RT (min) | LCMS MS (M + H) | NMR |
|---|---|---|---|---|---|---|
| 10-7 | 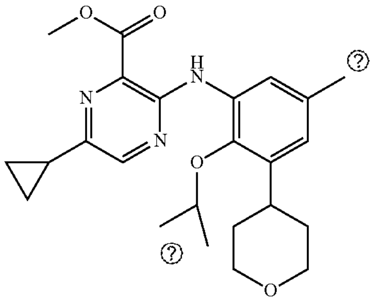 | 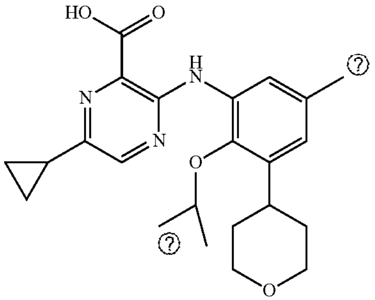 | A | 1.69 | 424 | 1H-NMR (MeOD) δ: 8.32-8.27 (m, 2H), 6.97-6.44 (m, 2H), 4.04 (d, 2H, J = 12.6 Hz), 3.61-3.50 (m, 3H), 2.24-2.05 (m, 1H), 1.73-1.70 (m, 4H), 1.07-0.95 (m, 4H). |
| 10-8 | 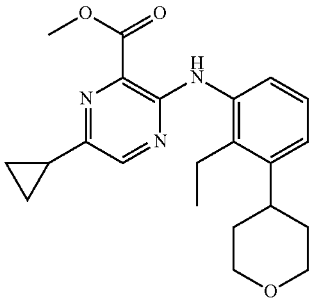 | 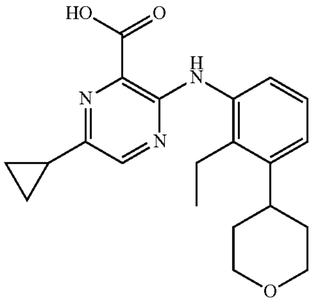 | A | 1.63 | 368 | 1H-NMR (CDCl3) δ: 9.70 (s, 1H), 8.31 (s, 1H), 7.65 (d, 1H, J = 7.9 Hz), 7.25-7.23 (m, 1H), 7.13 (d, 1H, J = 6.6 Hz), 4.10 (dd, 2H, J = 11.2, 4.0 Hz), 3.56 (t, 2H, J = 10.9 Hz), 3.08-2.96 (m, 1H), 2.71 (t, 2H, J = 8.3 Hz), 2.10-1.99 (m, 1H), 1.96-1.81 (m, 2H), 1.72-163 (m, 2H), 1.62-1.49 (m, 2H), 1.09-0.91 (m, 4H), 1.05 (t, 3H, J = 7.3 Hz). |
| 10-9 | 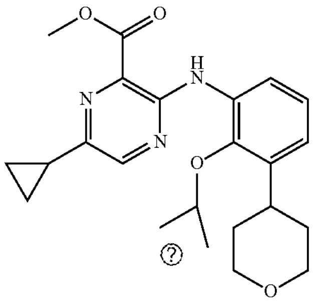 | 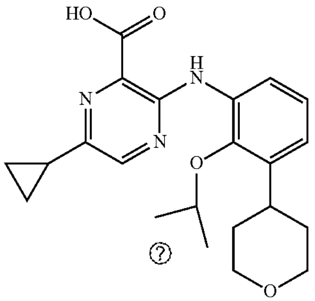 | A | 1.59 | 406 | 1H-NMR (DMSO-D6) δ: 10.52 (br s, 1H), 8.40 (s, 1H), 8.23 (d, 1H, J = 7.3 Hz), 7.28 (t, 1H, J = 7.9 Hz), 7.24-6.73 (m, 2H), 4.01-3.92 (m, 2H), 3.50-3.40 (m, 2H), 3.24-3.08 (m, 1H), 2.22-2.10 (m, 1H), 1.80-1.55 (m, 4H), 1.01-0.90 (m, 4H). |

TABLE 7-continued
| Reference Example No. | A | B | LCMS Method | LCMS RT (min) | LCMS MS (M + H) | NMR |
|---|---|---|---|---|---|---|
| 10-10 | 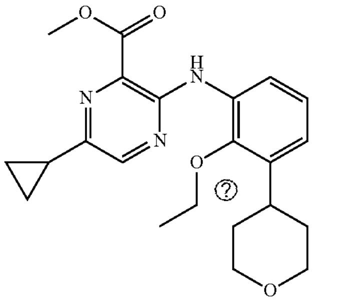 | 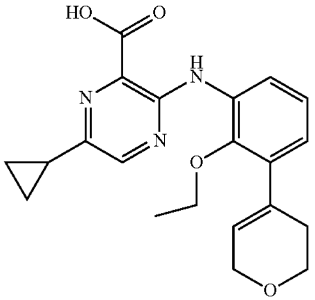 | B | 4.68 | 382 | 1H-NMr (DMSO-D6) δ: 12.30 (br s, 1H), 11.15 (br s, 1H), 8.49 (d, 1H, J = 8.4 Hz), 8.36 (br s, 1H), 7.06 (t, 1H, J = 8.0 Hz), 6.80 (dd, 1H, J = 7.6, 1.2 Hz), 5.97 (br s, 1H), 4.22 (m, 2H), 3.86-3.80 (m, 4H), 2.45 (m, 2H), 2.14 (br s, 1H), 1.37 (t, 3H, J =6.8 Hz), 0.92 (br s, 4H). |
| 10-11 | 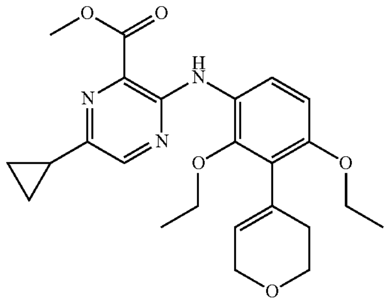 | 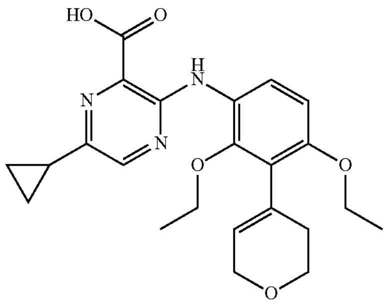 | B | 4.78 | 426 | 1H-NMR (DMSO-D6) δ: 10.71 (br s, 1H) 8.35 (s, 1H), 8.31 (d, 1H, J = 9.2 Hz), 6.75 (d, 1H, J = 9.2 Hz), 5.69 (s, 1H) 4.20 (d, 2H, J = 2.4 Hz), 3.96 (d, 2H, J = 6.8 Hz), 3.84-3.79 (m, 4H). 2.33 (m. 2H), 2.12 (m, 1H) 1.33 (t, 3H. J = 6.8 Hz), 1.29 (t, 3H, J = 6.8 Hz). 0.91 (m, 4H). |
| 10-12 | 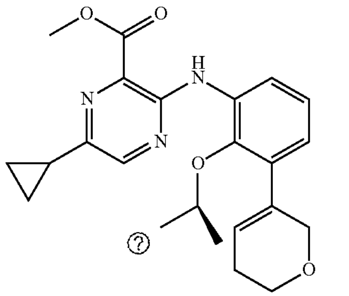 | 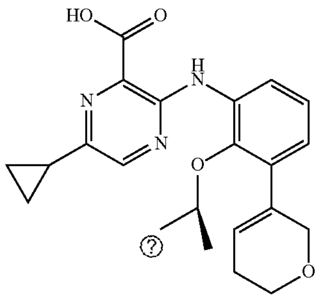 | A | 1.83 | 450 | 1H-NMR (DMSO-D6) δ: 13.46 (br s, 1H) 10.56 (br s, 1H), 8.41 (s, 1H), 8.35 (dd, 1H J = 7.9, 1.8 Hz), 7.15 (t 1H, .J = 7.9 Hz), 6.86 (dd, 1H, J = 76, 1.7 Hz)., 6.02 (br s, 1H). 4.75-4.63 (m, 1H), 4.34 (d, 1H. J = 15.9 Hz), 4.22 (d, 1H, J = 15.9 Hz), 3.77 (t, 2H, J = 5.3 Hz), 2.30-2.20 (m, 2H), 2.20-2.10 m, 1H) 1.29 (d 3H. J = 6.6 Hz). 0.99-0.90 (m, 4H). |

TABLE 7-continued
| Reference Example No. | A | B | LCMS Method | RT (min) | MS (M + H) | NMR |
|---|---|---|---|---|---|---|
| 10-13 | 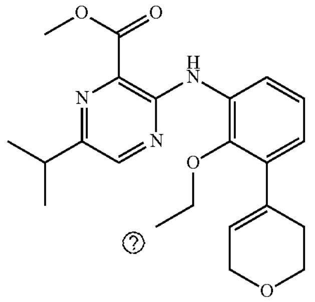 | 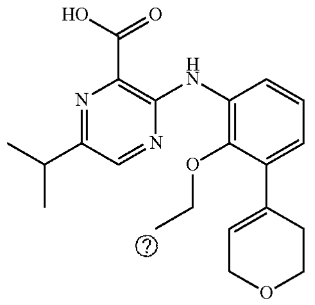 | A | 1.79 | 438 | 1H-NMR (CDCl3) δ: 10.97 (s, 1H), 10.32 (s, 1H), 8.40 (s, 1H, 8.30 (dd, 1H, J = 8.3, 1.5 Hz), 7.16 (t, 1H. J = 8.0 Hz), 6.93 (dd, 1H, J = 7.8, 1.5 Hz), 5.00 (s, 1H). 4.32 (q, 2H, J = 2.7 Hz), 4.24 (q, 2H, J = 8.4 Hz), 3.94 (t, 2H, J = 5.4 Hz), 3.14-3.07 (m, 1H), 2.55-2.49 (m, 2H), 1.34 (d, 6H, J = 6.8 Hz). |
| 10-14 | 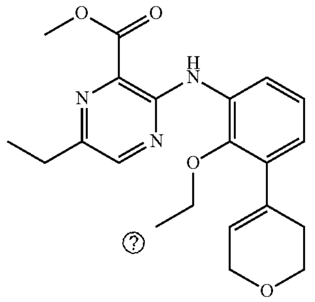 | 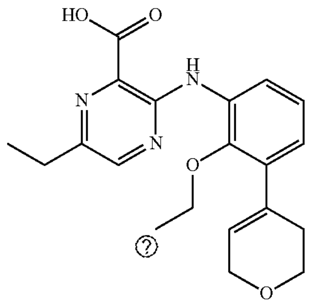 | A | 1.65 | 424 | 1H-NMR (DMSO-D6) δ: 13.54 (br s, 1H) 10.55 (br s, 1H), 3.38 (s, 1H), 8.36 (d, 1H, J = 8.3 Hz), 7.17 (t, 1H, J = 8.0 Hz), 6.90 (dd, 1H, J = 7.6, 1.4 Hz), 5.97 (s, 1H) 4.43 (q, 2H, J = 8.9 Hz), 4.20 (d, 2H, J = 2.3 Hz), 3.82 (t, 2H. J = 5.3 Hz), 2.74 (q 2H, J = 7.6 Hz), 245-2.38 (m 2H), 1.24 (t, 3H, J = 7.6 Hz). |
| 10-15 | 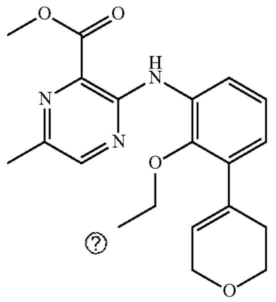 | 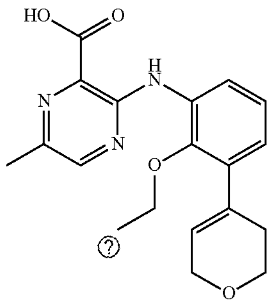 | A | 1.51 | 410 | 1H-NMR (DMSO-D6) δ: 13.52 (br s, 1H), 10.68 (br s, 1H), 8.36-8.33 (m 2H) 7.17 (t, 1H. J = 8.0 Hz). 6.90 (dd, 1H, J = 7.9, 1.4 Hz), 5.97 (s. 1H), 4.43 (q 2H, J = 9.0 Hz), 4.23-4.18 (m, 2H), 3.82 (t, 2H, J = 5.3 Hz), 2.46- 2.38 (m 2H), 2.44 (s, 3H). |

Example 1-1

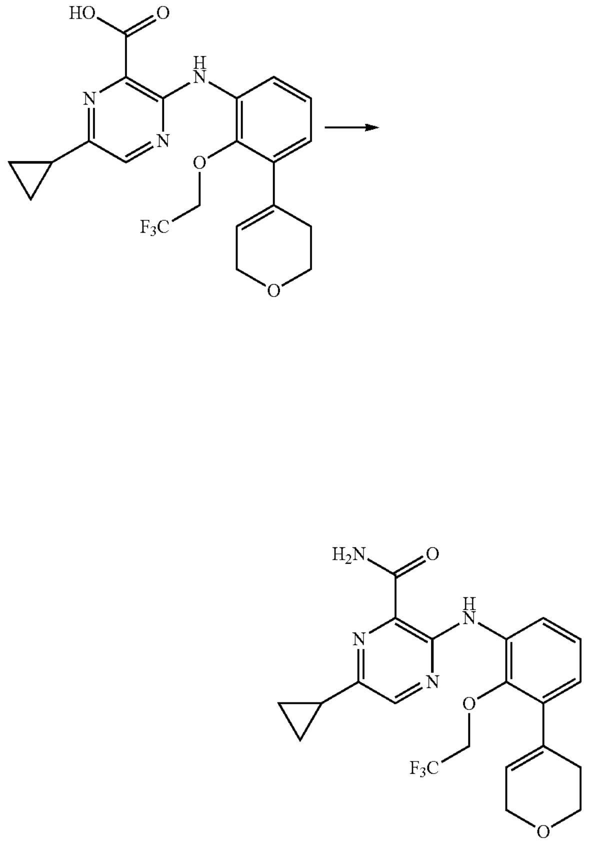 [SMILES: O=C(O)c1nc(C2CC2)cnc1Nc1cccc(C2=CCOCC2)c1OCC(F)(F)F ; NC(=O)c1nc(C2CC2)cnc1Nc1cccc(C2=CCOCC2)c1OCC(F)(F)F]

A mixture of 6-cyclopropyl-3-((3-(3,6-dihydro-2H-pyran-4-yl)-2-(2,2,2-trifluoroethoxy)phenyl)amino)pyrazine-2-carboxylic acid (30 mg), 1,1'-carbonyldiimidazole (15 mg), and tetrahydrofuran (0.80 mL) was stirred at room temperature for 30 minutes. 1,1'-Carbonyldiimidazole (8.1 mg) was added to the mixture which was then stirred for 15 minutes. 1,1'-Carbonyldiimidazole (23 mg) was added to the mixture which was then stirred for 10 minutes. A 7 mol/L ammonia methanol solution (0.30 mL) was added to the mixture which was then stirred for 30 minutes. An aqueous sodium chloride solution was added to the mixture which was then extracted twice with ethyl acetate. The solvent of the organic layer was distilled off under reduced pressure, and the obtained residue was purified by silica gel column chromatography (hexane:ethyl acetate gradient elution=100:0 to 70:30) to obtain 6-cyclopropyl-3-((3-(3,6-dihydro-2H-pyran-4-yl)-2-(2,2,2-trifluoroethoxy)phenyl)amino)pyrazine-2-carboxamide (27 mg) as a yellow solid.

1H-NMR (DMSO-D6) δ: 11.30 (br s, 1H), 8.42-8.36 (m, 2H), 8.20 (br s, 1H), 7.94 (br s, 1H), 7.15 (t, 1H, J=7.9 Hz), 6.86 (d, 1H, J=7.9 Hz), 5.95 (br s, 1H), 4.40 (q, 2H, J=9.0 Hz), 4.22-4.17 (m, 2H), 3.82 (t, 2H, J=5.3 Hz), 2.44-2.37 (m, 2H), 2.20-2.07 (m, 1H), 1.08-0.87 (m, 4H).

LCMS (Method A)

MS (ESI m/z): 435 (M+H)

RT (min): 1.74

Example 1-2

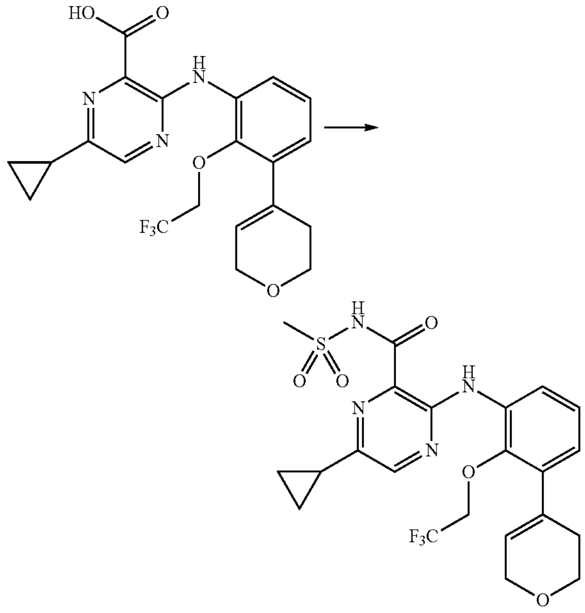

A mixture of 6-cyclopropyl-3-((3-(3,6-dihydro-2H-pyran-4-yl)-2-(2,2,2-trifluoroethoxy)phenyl)amino)pyrazine-2-carboxylic acid (100 mg), 1,1'-carbonyldiimidazole (150 mg), and tetrahydrofuran (2.0 mL) was stirred at room temperature for 1 hour. 1,1'-Carbonyldiimidazole (37 mg) was added to the mixture which was then stirred for 30 minutes. Methanesulfonamide (87 mg) and 1,8-diazabicyclo [5.4.0]-7-undecene (140 mg) were added to the mixture which was then stirred for 30 minutes. The pH was adjusted to 5 with 1 mol/L hydrochloric acid. An aqueous sodium chloride solution and ethyl acetate were added thereto, and the solid matter was collected by filtration. The filtrate was extracted twice with ethyl acetate, the solvent of the organic layer was distilled off under reduced pressure, and the residue was combined with the solid matter. Methanol (3.0 mL) was added to the obtained residue which was then suspended and stirred. Water (3.0 mL) was added thereto, followed by stirring, and the solid matter was collected by filtration. The obtained solid matter was purified by silica gel column chromatography (hexane:ethyl acetate gradient elution=100:0 to 0:100-methanol:ethyl acetate gradient elution=20:80) to obtain 6-cyclopropyl-3-((3-(3,6-dihydro-2H-pyran-4-yl)-2-(2,2,2-trifluoroethoxy)phenyl)amino)-N-(methylsulfonyl)pyrazine-2-carboxamide (72 mg) as a pale yellow solid.

1H-NMR (DMSO-D6) δ: 11.58 (br s, 1H), 10.53 (br s, 1H), 8.51 (s, 1H), 8.29 (d, 1H, J=7.6 Hz), 7.18 (t, 1H, J=7.6 Hz), 6.93 (d, 1H, J=7.6 Hz), 5.99 (br s, 1H), 4.45 (q, 2H, J=8.8 Hz), 4.25-4.18 (m, 2H), 3.83 (t, 2H, J=5.3 Hz), 3.38 (s, 3H), 2.47-2.38 (m, 2H), 2.25-2.12 (m, 1H), 1.17-1.09 (m, 2H), 1.02-0.92 (m, 2H).

LCMS (Method A)

MS (ESI m/z): 513 (M+H)

RT (min): 1.74

Example 1-3

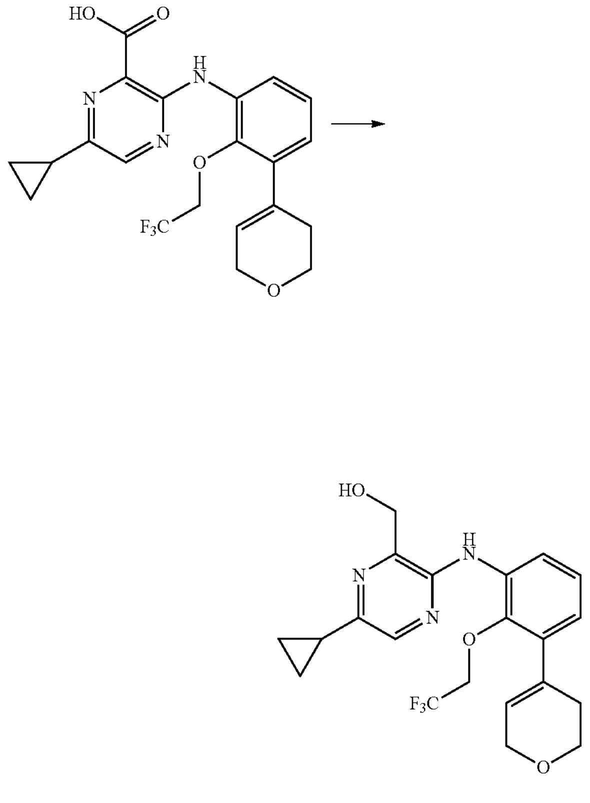

A mixture of 6-cyclopropyl-3-((3-(3,6-dihydro-2H-pyran-4-yl)-2-(2,2,2-trifluoroethoxy)phenyl)amino)pyrazine-2-carboxylic acid (30 mg), 1,1'-carbonyldiimidazole (34 mg), and tetrahydrofuran (1.0 mL) was stirred at room temperature for 30 minutes. Sodium borohydride (16 mg) and 2-propanol (0.20 mL) were added to the mixture which was then stirred for 1 hour. A mixture of sodium borohydride (16 mg) and methanol (0.30 mL) was added dropwise thereto, followed by stirring for 1 hour. An aqueous sodium chloride solution was added to the mixture which was then extracted twice with ethyl acetate. The solvent of the organic layer was distilled off under reduced pressure, and the obtained residue was purified by silica gel column chromatography (hexane:ethyl acetate gradient elution=100:0 to 50:50) to obtain 6-cyclopropyl-3-((3-(3,6-dihydro-2H-pyran-4-yl)-2-(2,2,2-trifluoroethoxy)phenyl)amino)pyrazin-2-yl)methanol (16 mg) as a yellow solid.

1H-NMR (DMSO-D6) δ: 8.86 (br s, 1H), 8.26 (d, 1H, J=7.9 Hz), 8.07 (s, 1H), 7.12 (t, 1H, J=7.9 Hz), 6.82 (d, 1H, J=7.9 Hz), 6.10-5.91 (m, 2H), 4.65 (s, 2H), 4.38 (q, 2H, J=9.0 Hz), 4.24-4.15 (m, 2H), 3.81 (t, 2H, J=5.3 Hz), 2.45-2.36 (m, 2H), 2.13-2.00 (m, 1H), 1.00-0.77 (m, 4H).

LCMS (Method A)

MS (ESI m/z): 422 (M+H)

RT (min): 1.71

Example 1-4

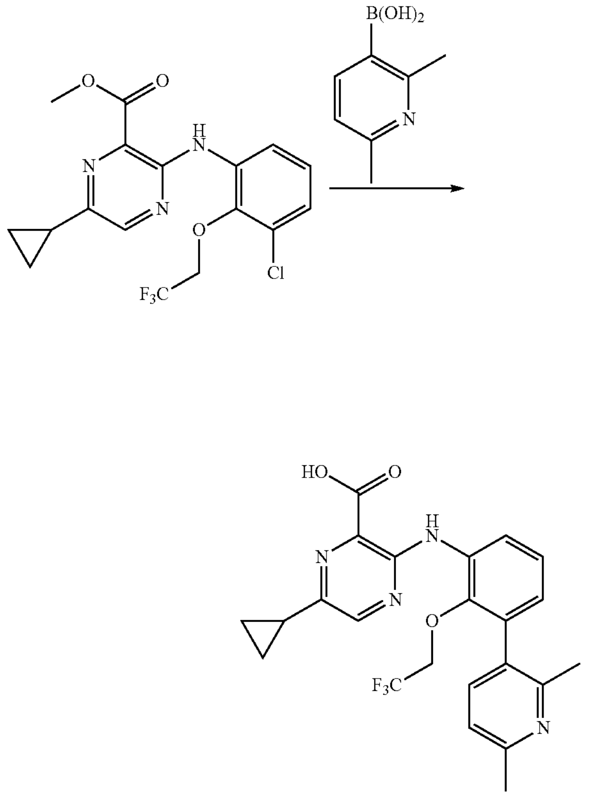

A mixture of methyl 3 #3-chloro-2-(2,2,2-trifluoroethoxy) phenyl)amino)-6-cyclopropylpyrazine-2-carboxylate (100 mg), 2,6-dimethylpyridine-3-boronic acid (42 mg), potassium phosphate (110 mg), bis(di-tert-butyl(4-dimethylaminophenyl)phosphine)dichloropalladium (II) (9.1 mg), 1,2-dimethoxyethane (3.0 mL), and water (1.0 mL) was irradiated with microwaves (microwave reactor, 135° C., 1 hour, 2.45 GHz, 0 to 240 W). An aqueous sodium chloride solution and 1 mol/L hydrochloric acid were added to the reaction liquid which was then extracted twice with ethyl acetate. The organic layer was dried over magnesium sulfate, and the solvent was distilled off under reduced pressure. The obtained residue was purified by silica gel column chromatography to obtain 6-cyclopropyl-3-((3-(2,6-dimethylpyridin-3-yl)-2-(2,2,2-trifluoroethoxy)phenyl)amino) pyrazine-2-carboxylic acid (12 mg) as a yellow oil.

1H-NMR (CDCl3) δ: 10.43 (br s, 1H), 8.48-8.35 (m, 2H), 7.52 (d, 1H, J=7.9 Hz), 7.31-7.19 (m, 1H), 7.10 (d, 1H, J=7.9 Hz), 6.92 (d, 1H, J=5.9 Hz), 3.97-3.66 (m, 2H), 2.62 (s, 3H), 2.46 (s, 3H), 2.17-2.01 (m, 1H), 1.26-0.86 (m, 4H).

LCMS (Method A)

MS (ESI m/z): 459 (M+H)

RT (min): 1.15

Example 1-5

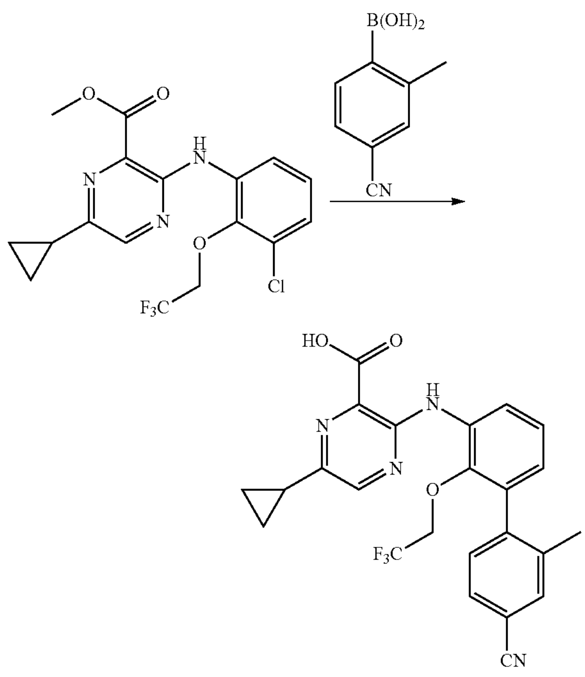

In the same manner as in Example 1-4, 3-((4'-cyano-2'-methyl-2-(2,2,2-trifluoroethoxy)-[1,1'-biphenyl]-3-yl)amino)-6-cyclopropylpyrazine-2-carboxylic acid was obtained as a yellow solid by changing 2,6-dimethylpyridine-3-boronic acid to 4-cyano-2-methylphenylboronic acid.

1H-NMR (DMSO-D6) δ: 13.72-13.09 (m, 1H), 10.73 (br s, 1H), 8.54 (d, 1H, J=8.6 Hz), 8.45 (s, 1H), 7.83 (s, 1H), 7.75 (d, 1H, J=9.2 Hz), 7.48 (d, 1H, J=7.9 Hz), 7.30 (t, 1H, J=7.9 Hz), 6.89 (d, 1H, J=7.9 Hz), 4.32-3.84 (m, 2H), 2.24-2.11 (m, 4H), 1.03-0.85 (m, 4H).

LCMS (Method A)

MS (ESI m/z): 469 (M+H)

RT (min): 1.89

Example 1-6

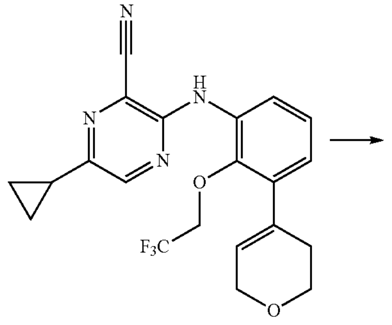

-continued

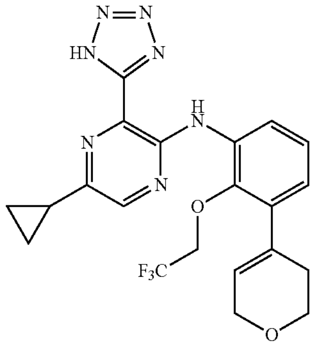

A mixture of 6-cyclopropyl-3-((3-(3,6-dihydro-2H-pyran-4-yl)-2-(2,2,2-trifluoroethoxy)phenyl)amino)pyrazine-2-carbonitrile (100 mg), N,N-dimethylformamide (5.0 mL), ammonium chloride (17 mg), and sodium azide (21 mg) was stirred at 80° C. for 6 hours and 30 minutes. Water was added to the mixture which was then extracted with ethyl acetate. The organic layer was separated twice with an aqueous sodium chloride solution and dried over sodium sulfate, and the solvent was distilled off under reduced pressure. 50% aqueous methanol was added to the obtained residue which was then stirred. The solid was collected by filtration to obtain 5-cyclopropyl-N-((3-(3,6-dihydro-2H-pyran-4-yl)-2-(2,2,2-trifluoroethoxy)phenyl)-3-(1H-tetrazol-5-yl)pyrazine-2-amine (76 mg) as a yellow solid.

1H-NMR (DMSO-D6) δ: 10.36 (br s, 1H), 8.41 (s, 1H), 8.34 (dd, 1H, J=8.3, 1.5 Hz), 7.20 (t, 1H, J=7.9 Hz), 6.93 (dd, 1H, J=7.7, 1.6 Hz), 6.00 (br s, 1H), 4.45 (q, 2H, J=9.0 Hz), 4.25-4.19 (m, 2H), 3.84 (t, 2H, J=5.4 Hz), 2.48-2.40 (m, 2H), 2.26-2.16 (m, 1H), 1.12-1.06 (m, 2H), 1.04-0.96 (m, 2H).

LCMS (Method B)

MS (ESI m/z): 460 (M+H)

RT (min): 4.62

Example 1-7

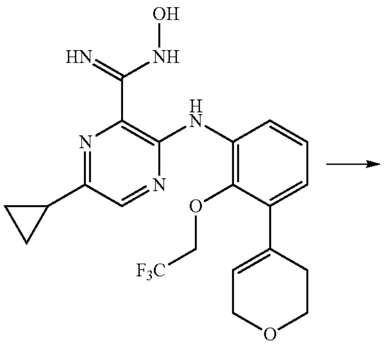

-continued

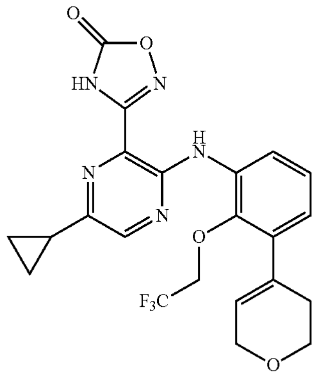

-continued

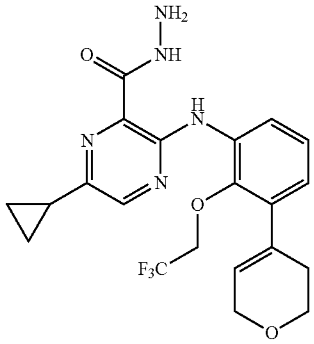

A mixture of 6-cyclopropyl-3-((3-(3,6-dihydro-2H-pyran-4-yl)-2-(2,2,2-trifluoroethoxy)phenyl)amino)-N-hydroxypyrazine-2-carboximidamide (99 mg), N,N-dimethylformamide (5.0 mL), and 1,1'-carbonyldiimidazole (36 mg) was stirred at 40° C. for 2 hours. The mixture was stirred at 80° C. for 7 hours. The mixture was cooled to room temperature, and the solvent was distilled off under reduced pressure. The obtained residue was purified by silica gel column chromatography (hexane:ethyl acetate gradient elution=90:10 to 75:25) to obtain 3-(6-cyclopropyl-3-((3-(3,6-dihydro-2H-pyran-4-yl)-2-(2,2,2-trifluoroethoxy)phenyl)amino)pyrazin-2-yl)-1,2,4-oxadiazol-5(4H)-one (43 mg) as a yellow solid.

1H-NMR (DMSO-D6) δ: 13.06 (br s, 1H), 9.24 (s, 1H), 8.45 (s, 1H), 8.33 (dd, 1H, J=7.9, 1.5 Hz), 7.19 (t, 1H, J=7.9 Hz), 6.94 (dd, 1H, J=7.6, 1.5 Hz), 5.98 (s, 1H), 4.42 (q, 2H, J=9.0 Hz), 4.23-4.18 (m, 2H), 3.82 (t, 2H, J=5.3 Hz), 2.45-2.38 (m, 2H), 2.23-2.14 (m, 1H), 1.13-1.07 (m, 2H), 0.99-0.93 (m, 2H).

LCMS (Method B)

MS (ESI m/z): 476 (M+H)

RT (min): 4.69

Example 1-8

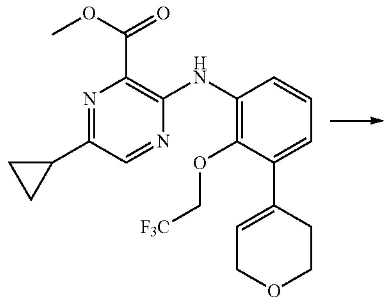

A mixture of methyl 6-cyclopropyl-3-((3-(3,6-dihydro-2H-pyran-4-yl)-2-(2,2,2-trifluoroethoxy)phenyl)amino)pyrazine-2-carboxylate (150 mg), ethanol (10 mL), and hydrazine monohydrate (84 mg) was stirred at room temperature for 2 hours. The mixture was stirred at 50° C. for 1 hour and was stirred for 15 hours under heating and reflux conditions. The mixture was stirred for 20 minutes under ice cooling, and the precipitated solid was collected by filtration and dried to obtain 6-cyclopropyl-3-((3-(3,6-dihydro-2H-pyran-4-yl)-2-(2,2,2-trifluoroethoxy)phenyl)amino)pyrazine-2-carbohydrazide (123 mg) as a yellow solid.

1H-NMR (DMSO-D6) δ: 11.09 (s, 1H), 9.96 (br s, 1H), 8.38 (s, 1H), 8.32 (dd, 1H, J=8.3, 1.5 Hz), 7.14 (t, 1H, J=8.1 Hz), 6.86 (dd, 1H, J=7.7, 1.6 Hz), 5.95 (br s, 1H), 4.63 (br s, 2H), 4.42 (q, 2H, J=9.0 Hz), 4.23-4.18 (m, 2H), 3.82 (t, 2H, J=5.4 Hz), 2.45-2.38 (m, 2H), 2.16-2.08 (m, 1H), 1.09-1.04 (m, 2H), 0.95-0.89 (m, 2H).

LCMS (Method B)

MS (ESI m/z): 450 (M+H)

RT (min): 3.96

Example 1-9

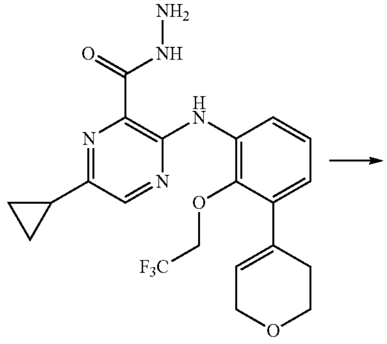

-continued

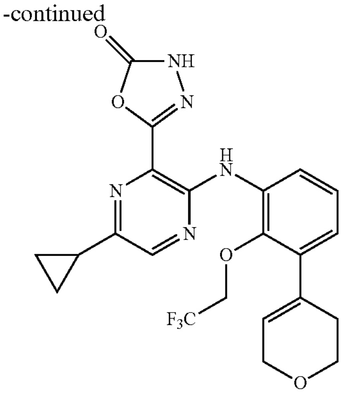

1,1'-Carbonyldiimidazole (42 mg) was added to a mixture of 6-cyclopropyl-3-((3-(3,6-dihydro-2H-pyran-4-yl)-2-(2,2,2-trifluoroethoxy)phenyl)amino)pyrazine-2-carbohydrazide (120 mg), N,N-dimethylformamide (4.0 mL), and triethylamine (36 μL) under ice cooling. The mixture was stirred at room temperature for 16 hours. The solvent was distilled off from the mixture under reduced pressure. The obtained residue was purified by silica gel column chromatography (hexane:ethyl acetate gradient elution=90:10 to 75:25) to obtain 5-(6-cyclopropyl-3-((3-(3,6-dihydro-2H-pyran-4-yl)-2-(2,2,2-trifluoroethoxy)phenyl)amino)pyrazin-2-yl)-1,3,4-oxadiazol-2(3H)-one (110 mg) as a yellow solid.

1H-NMR (DMSO-D6) δ: 13.04 (br s, 1H), 9.42 (s, 1H), 8.36 (s, 1H), 8.26 (dd, 1H, J=8.3, 1.5 Hz), 7.19 (t, 1H, J=7.9 Hz), 6.94 (dd, 1H, J=7.6, 1.5 Hz), 5.98 (br s, 1H), 4.40 (q, 2H, J=9.0 Hz), 4.23-4.18 (m, 2H), 3.83 (t, 2H, J=5.3 Hz), 2.46-2.38 (m, 2H), 2.24-2.15 (m, 1H), 1.03-0.97 (m, 2H), 0.94-0.88 (m, 2H).

LCMS (Method B)

MS (ESI m/z): 476 (M+H)

RT (min): 4.59

Example 1-10

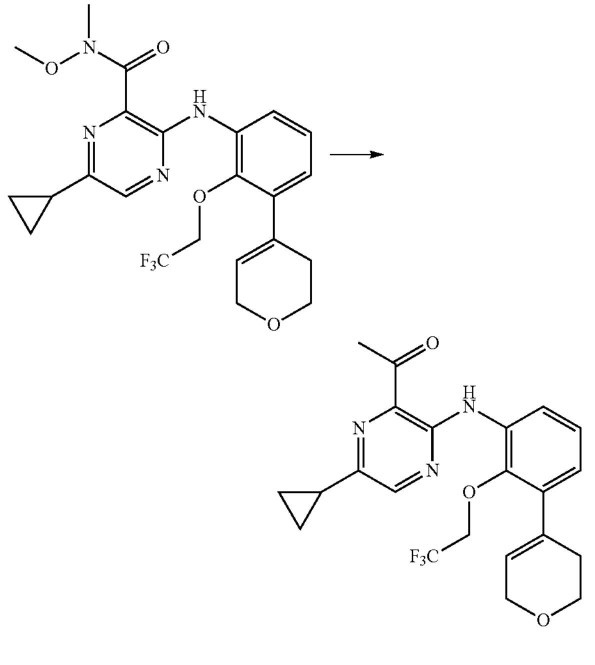

Under ice cooling, a 3 mol/L methylmagnesium bromide diethyl ether solution (0.77 mL) was added to a mixture of 6-cyclopropyl-3-((3-(3,6-dihydro-2H-pyran-4-yl)-2-(2,2,2-trifluoroethoxy)phenyl)amino)-N-methoxy-N-methylpyrazine-2-carboxamide (440 mg) and tetrahydrofuran (9.0 mL) which was then stirred for 1 hour and 30 minutes. An aqueous ammonium chloride solution was added to the mixture which was then extracted with ethyl acetate. The organic layer was washed with an aqueous sodium chloride solution and dried over sodium sulfate. The solvent of the organic layer was distilled off under reduced pressure, and the obtained residue was purified by silica gel column chromatography (hexane:ethyl acetate gradient elution=90:10 to 80:20) to obtain 1-(6-cyclopropyl-3-((3-(3,6-dihydro-2H-pyran-4-yl)-2-(2,2,2-trifluoroethoxy)phenyl)amino)pyrazin-2-yl)ethan-1-one (373 mg) as a yellow solid.

1H-NMR (CDCl3) δ: 10.90 (br s, 1H), 8.33-8.27 (m, 2H), 7.14 (t, 1H, J=7.9 Hz), 6.89 (dd, 1H, J=7.6, 1.5 Hz), 5.98 (br s, 1H), 4.32 (q, 2H, J=2.7 Hz), 4.22 (q, 2H, J=8.5 Hz), 3.93 (t, 2H, J=5.4 Hz), 2.70 (s, 3H), 2.56-2.49 (m, 2H), 2.10-2.02 (m, 1H), 1.04-0.99 (m, 4H).

LCMS (Method B)

MS (ESI m/z): 434 (M+H)

RT (min): 5.50

Example 1-11

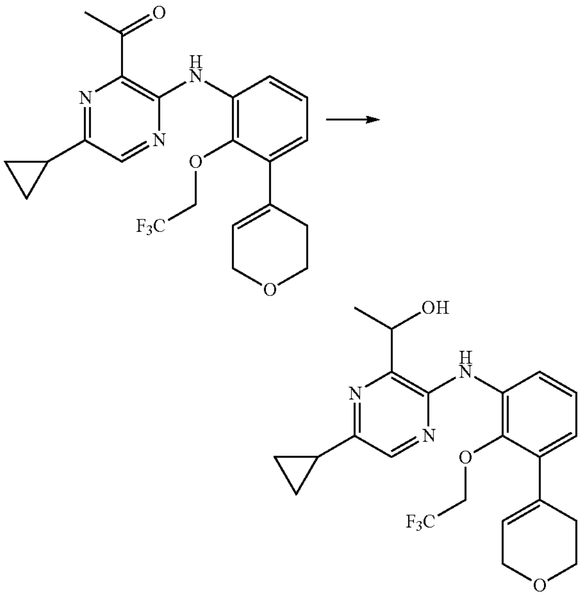

Lithium aluminum hydride (14 mg) was added to a mixture of 1-(6-cyclopropyl-3-((3-(3,6-dihydro-2H-pyran-4-yl)-2-(2,2,2-trifluoroethoxy)phenyl)amino)pyrazin-2-yl)ethan-1-one (80 mg) and tetrahydrofuran (4.0 mL) which was then stirred at room temperature for 30 minutes. A 1 mol/L aqueous sodium hydroxide solution and water were added to the mixture which was then extracted with ethyl acetate. The organic layer was washed with an aqueous sodium chloride solution and dried over sodium sulfate. The solvent of the organic layer was distilled off under reduced pressure, and the obtained residue was purified by silica gel column chromatography (hexane:ethyl acetate gradient elution=90:10 to 80:20) to obtain 1-(6-cyclopropyl-3-((3-(3,6- dihydro-2-H-pyran-4-yl)-2-(2,2,2-trifluoroethoxy)phenyl) amino)pyrazin-2-yl)ethan-1-ol (77 mg) as a yellow solid.

1H-NMR (DMSO-D6) δ: 9.25 (br s, 1H), 8.28 (dd, 1H, J=8.3, 1.7 Hz), 8.04 (s, 1H), 7.11 (t, 1H, J=7.9 Hz), 6.80 (dd, 1H, J=7.7, 1.6 Hz), 6.25 (s, 1H), 5.94 (br s, 1H), 4.90-4.80 (m, 1H), 4.42-4.31 (m, 2H), 4.22-4.17 (m, 2H), 3.81 (t, 2H, J=5.4 Hz), 2.44-2.37 (m, 2H), 2.10-2.01 (m, 1H), 1.42 (d, 3H, J=6.6 Hz), 0.94-0.87 (m, 2H), 0.84-0.79 (m, 2H).

LCMS (Method B)

MS (ESI m/z): 436 (M+H)

RT (min): 4.80

Example 1-12

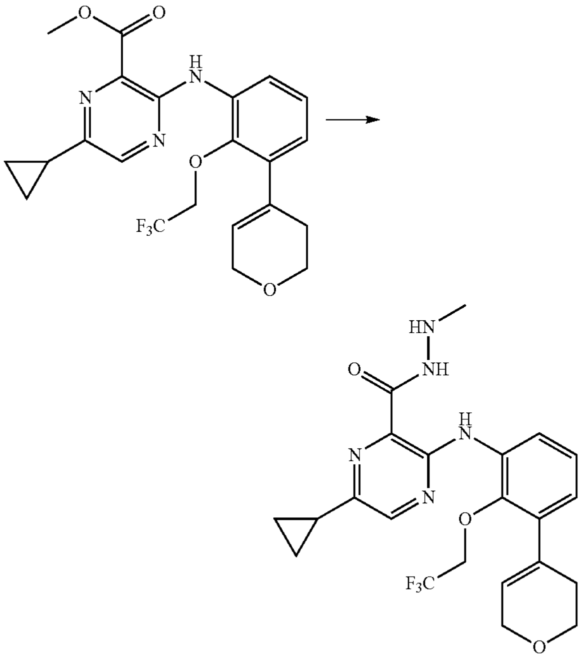

A mixture of methyl 6-cyclopropyl-3-((3-(3,6-dihydro-2H-pyran-4-yl)-2-(2,2,2-trifluoroethoxy)phenyl)amino) pyrazine-2-carboxylate (100 mg), methanol (3 mL), and methylhydrazine (100 mg) was stirred in a sealed container at 80° C. for 18 hours. The obtained residue was purified by silica gel column chromatography (hexane:ethyl acetate gradient elution=95:5 to 80:20). 50% aqueous ethanol was added to the purified product which was then suspended and stirred, and the solid matter was collected by filtration and dried to obtain 6-cyclopropyl-3-((3-(3,6-dihydro-2H-pyran-4-yl)-2-(2,2,2-trifluoroethoxy)phenyl)amino)-N'-methylpyrazine-2-carbohydrazide (65 mg) as a yellow solid.

1H-NMR (DMSO-D6) δ: 11.05 (s, 1H), 10.14 (br s, 1H), 8.38 (s, 1H), 8.30 (dd, 1H, J=8.2, 1.6 Hz), 7.15 (t, 1H, J=8.1 Hz), 6.87 (dd, 1H, J=7.7, 1.6 Hz), 5.96 (br s, 1H), 5.20-5.08 (m, 1H), 4.41 (q, 2H, J=9.0 Hz), 4.23-4.17 (m, 2H), 3.82 (t, 2H, J=5.4 Hz), 2.57 (d, 3H, J=4.4 Hz), 2.45-2.38 (m, 2H), 2.17-2.08 (m, 1H), 1.10-1.03 (m, 2H), 0.96-0.89 (m, 2H).

LCMS (Method B)

MS (ESI m/z): 464 (M+H)

RT (min): 3.99

Example 1-13

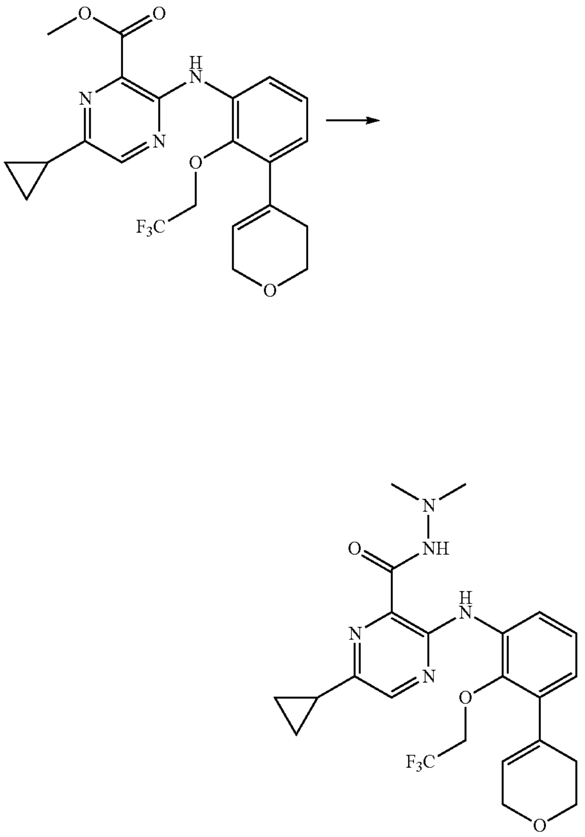

A mixture of methyl 6-cyclopropyl-3-((3-(3,6-dihydro-2H-pyran-4-yl)-2-(2,2,2-trifluoroethoxy)phenyl)amino) pyrazine-2-carboxylate (100 mg), methanol (2.0 mL), and 1,1-dimethylhydrazine (340 μL) was irradiated with microwaves (microwave reactor, 120° C., 7 hours, 2.45 GHz, 0 to 240 W). 4-(4,6-dimethoxy-1,3,5-triazin-2-yl)-4-methylmorpholinium chloride (125 mg) was added to the mixture which was then stirred at room temperature for 5 hours. The mixture was stirred at 40° C. for 3 hours. 4-(4,6-dimethoxy-1,3,5-triazin-2-yl)-4-methylmorpholinium chloride (125 mg) was added to the mixture which was then stirred at 40° C. for 17 hours. The solvent was distilled off under reduced pressure, and the obtained residue was purified by reverse phase silica gel column chromatography (KP-C18-HS, 0.1% aqueous trifluoroacetic acid:methanol gradient elution=70:30 to 30:70). Fractions containing a desired product were combined and the solvent was distilled off under reduced pressure. An aqueous sodium hydrogen carbonate solution was added to the obtained residue which was then extracted with ethyl acetate. The organic layer was washed with brine and dried over sodium sulfate, and the solvent was distilled off under reduced pressure. The residue was purified by silica gel column chromatography (hexane:ethyl acetate gradient elution=90:10 to 80:20). Purification by preparative thin layer chromatography (hexane:ethyl acetate=75:25) was carried out to obtain 6-cyclopropyl-3-((3-(3,6-dihydro-2H-pyran-4-yl)-2-(2,2,2-trifluoroethoxy)phenyl)amino)-N,N-dimethylpyrazine-2-carbohydrazide (21 mg) as a yellow solid.

1H-NMR (DMSO-D6) δ: 11.05 (s, 1H), 9.46 (s, 1H), 8.36 (s, 1H), 8.30 (dd, 1H, J=7.9, 1.5 Hz), 7.14 (t, 1H, J=7.9 Hz), 6.87 (dd, 1H, J=7.6, 1.5 Hz), 5.96 (br s, 1H), 4.41 (q, 2H, J=9.0 Hz), 4.23-4.18 (m, 2H), 3.82 (t, 2H, J=5.3 Hz), 2.63 (s, 6H), 2.45-2.38 (m, 2H), 2.18-2.09 (m, 1H), 1.06-1.00 (m, 2H), 0.99-0.92 (m, 2H).

LCMS (Method B)

MS (ESI m/z): 478 (M+H)

RT (min): 4.31

Example 1-14

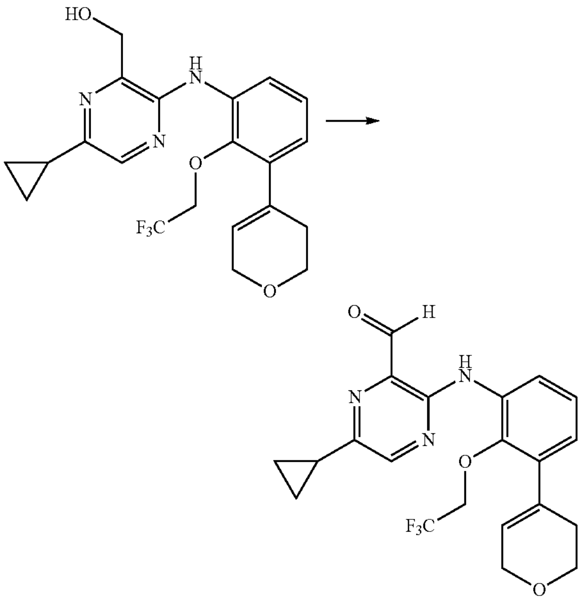

Under ice cooling, a Dess-Martin reagent (12 mg) was added to a mixture of 6-cyclopropyl-3-((3-(3,6-dihydro-2H-pyran-4-yl)-2-(2,2,2-trifluoroethoxy)phenyl)amino)pyrazin-2-yl)methanol (12 mg) and dichloromethane (1.0 mL) which was then stirred at room temperature for 1 hour. The Dess-Martin reagent (6 mg) was added to the mixture which was then stirred at room temperature for 30 minutes. The Dess-Martin reagent (6 mg) was added to the mixture which was then stirred at room temperature for 30 minutes. The Dess-Martin reagent (6 mg) was added to the mixture which was then stirred at room temperature for 30 minutes. An aqueous sodium hydrogen carbonate solution and an aqueous sodium sulfite solution were added to the mixture which was then extracted twice with ethyl acetate. The solvent of the organic layer was distilled off under reduced pressure, and the obtained residue was purified by silica gel column chromatography (hexane:ethyl acetate gradient elution=100:0 to 80:20) to obtain 6-cyclopropyl-3-((3-(3,6-dihydro-2H-pyran-4-yl)-2-(2,2,2-trifluoroethoxy)phenyl)amino)pyrazine-2-carbaldehyde (9.2 mg) as a yellow solid.

1H-NMR (DMSO-D6) δ: 10.41 (br s, 1H), 9.95 (s, 1H), 8.53 (s, 1H), 8.36 (d, 1H, J=7.9 Hz), 7.20 (t, 1H, J=7.9 Hz), 6.96 (d, 1H, J=7.9 Hz), 6.00 (br s, 1H), 4.45 (q, 2H, J=9.0 Hz), 4.26-4.17 (m, 2H), 3.83 (t, 2H, J=5.3 Hz), 2.47-2.38 (m, 2H), 2.32-2.18 (m, 1H), 1.06-0.93 (m, 4H).

LCMS (Method A)

MS (ESI m/z): 420 (M+H)

RT (min): 1.96

Example 1-15

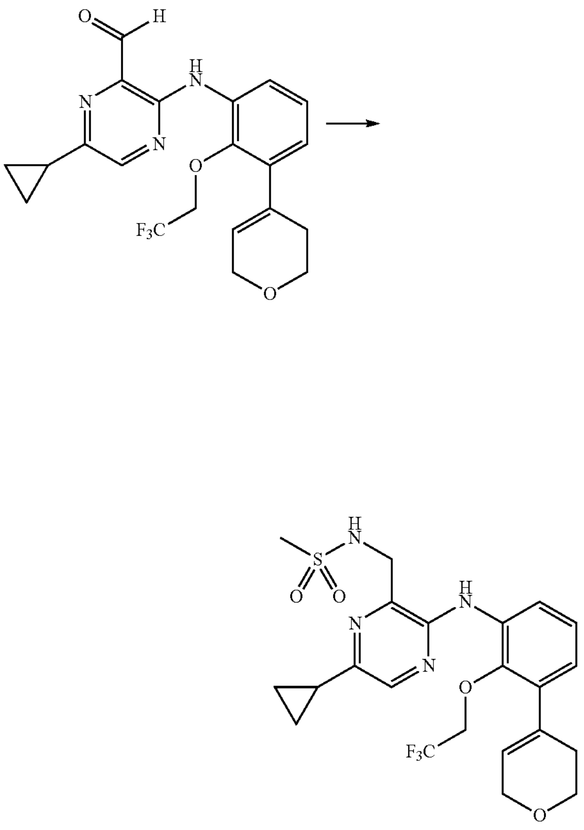 [SMILES: O=Cc1nc(C2CC2)cnc1Nc1cccc(C2=CCOCC2)c1OCC(F)(F)F ; CS(=O)(=O)NCc1nc(C2CC2)cnc1Nc1cccc(C2=CCOCC2)c1OCC(F)(F)F]

Sodium triacetoxyborohydride (130 mg) was added to a mixture of 6-cyclopropyl-3-((3-(3,6-dihydro-2H-pyran-4-yl)-2-(2,2,2-trifluoroethoxy)phenyl)amino)pyrazine-2-carbaldehyde (100 mg), methanesulfonamide (34 mg), dichloroethane (4.0 mL), and triethylamine (67 μL) which was then stirred at room temperature for 23 hours. 1 mol/L hydrochloric acid was added thereto, and the organic layer was separated. The aqueous layer was extracted with dichloromethane. The organic layers were combined, washed with an aqueous sodium hydrogen carbonate solution, and dried over sodium sulfate.

The obtained residue was purified by silica gel column chromatography (hexane:ethyl acetate gradient elution=90:10 to 65:35). A mixed solution of heptane/ethyl acetate (10/1) was added to the purified product which was then suspended and stirred. The solid matter was collected by filtration to obtain N-((6-cyclopropyl-3-((3-(3,6-dihydro-2H-pyran-4-yl)-2-(2,2,2-trifluoroethoxy)phenyl)amino)pyrazin-2-yl)methyl)methanesulfonamide (100 mg) as a white solid.

1H-NMR (DMSO-D6) δ: 8.02 (s, 1H), 7.72 (br s, 1H), 7.63 (dd, 1H, J=8.1, 1.7 Hz), 7.47 (br s, 1H), 7.13 (t, 1H, J=7.9 Hz), 6.93 (dd, 1H, J=7.7, 1.6 Hz), 5.93 (br s, 1H), 4.40-4.31 (m, 4H), 4.22-4.18 (m, 2H), 3.81 (t, 2H, J=5.4 Hz), 2.96 (s, 3H), 2.44-2.37 (m, 2H), 2.10-2.01 (m, 1H), 0.94-0.86 (m, 4H).

LCMS (Method B)

MS (ESI m/z): 499 (M+H)

RT (min): 4.52

Example 1-16

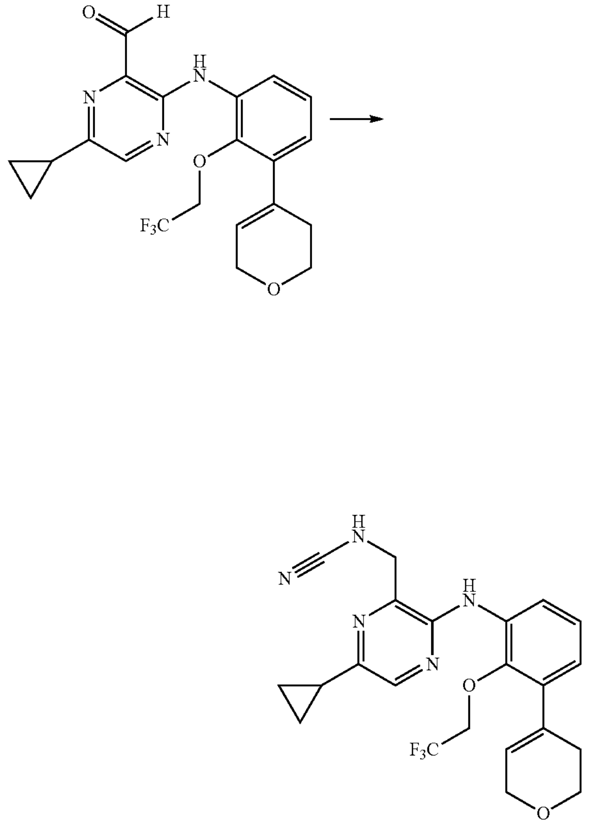 [SMILES: O=Cc1nc(C2CC2)cnc1Nc1cccc(C2=CCOCC2)c1OCC(F)(F)F ; N#CNCc1nc(C2CC2)cnc1Nc1cccc(C2=CCOCC2)c1OCC(F)(F)F]

A mixture of 6-cyclopropyl-3-((3-(3,6-dihydro-2H-pyran-4-yl)-2-(2,2,2-trifluoroethoxy)phenyl)amino)pyrazine-2-carbaldehyde (100 mg), cyanamide (20 mg), methanol (2.0 mL), dichloromethane (2.0 mL), and p-toluenesulfonic acid monohydrate (9.0 mg) was stirred at room temperature for 1 hour. Sodium cyanoborohydride (38 mg) was added to the mixture which was then stirred for 16 hours. The solvent was distilled off under reduced pressure, and an aqueous sodium hydrogen carbonate solution was added to the mixture which was then extracted with ethyl acetate. The organic layer was washed with an aqueous sodium chloride solution and dried over sodium sulfate. The solvent of the organic layer was distilled off under reduced pressure, and the obtained residue was purified by NH silica gel column chromatography (hexane:ethyl acetate gradient elution=80:20 to 55:45). The purified product was purified by silica gel column chromatography (dichloromethane: ethyl acetate gradient elution=100:0 to 65:35). N-((6-cyclopropyl-3-((3-(3,6-dihydro-2H-pyran-4-yl)-2-(2,2,2-trifluoroethoxy)phenyl)amino)pyrazin-2-yl)methyl)cyanamide (11 mg) was obtained.

LCMS (Method B)

MS (ESI m/z): 446 (M+H)

RT (min): 2.87

Example 1-17

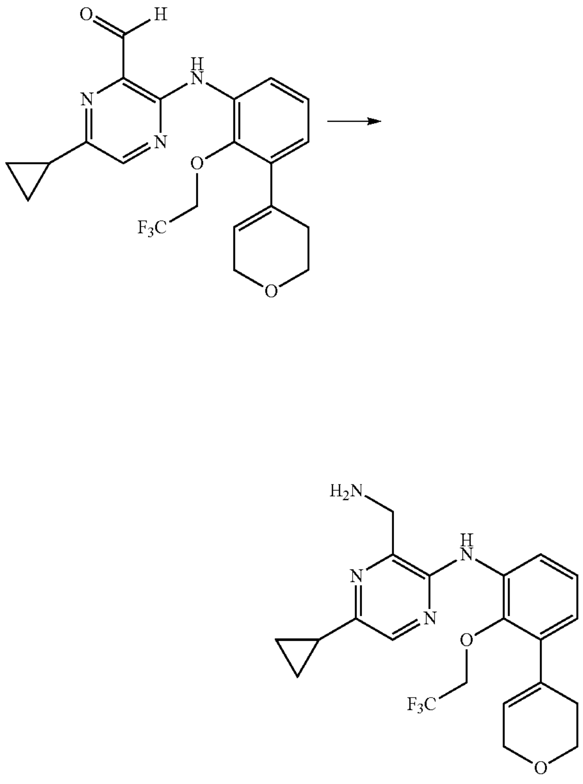

A mixture of 6-cyclopropyl-3-((3-(3,6-dihydro-2H-pyran-4-yl)-2-(2,2,2-trifluoroethoxy)phenyl)amino)pyrazine-2-carbaldehyde (100 mg), ammonium acetate (190 mg), methanol (8.0 mL), and dichloromethane (8.0 mL) was stirred at room temperature for 1 hour. Sodium cyanoborohydride (41 mg) was added to the mixture which was then stirred for 22 hours. The solvent was distilled off under reduced pressure, and a 1 mol/L aqueous sodium hydroxide solution was added to the mixture which was then extracted with ethyl acetate. The organic layer was washed with an aqueous sodium chloride solution and dried over sodium sulfate. The solvent of the organic layer was distilled off under reduced pressure, and the obtained residue was purified by silica gel column chromatography (hexane:ethyl acetate gradient elution=90:10 to 60:40) to obtain 3-(aminomethyl)-5-cyclopropyl-N-(3-(3,6-dihydro-2H-pyran-4-yl)-2-(2,2,2-trifluoroethoxy)phenyl)pyrazine-2-amine (28 mg) as an orange oil.

1H-NMR (DMSO-D6) δ: 10.61 (br s, 1H), 8.25 (dd, 1H, J=8.2, 1.6 Hz), 8.00 (s, 1H), 7.10 (t, 1H, J=7.9 Hz), 6.78 (dd, 1H, J=7.6, 1.7 Hz), 5.92 (br s, 1H), 4.39 (q, 2H, J=9.0 Hz), 4.22-4.16 (m, 2H), 3.96 (s, 2H), 3.80 (t, 2H, J=5.4 Hz), 2.44-2.36 (m, 2H), 2.08-2.00 (m, 1H), 0.92-0.77 (m, 4H).

LCMS (Method B)

MS (ESI m/z): 421 (M+H)

RT (min): 3.30

Example 1-18

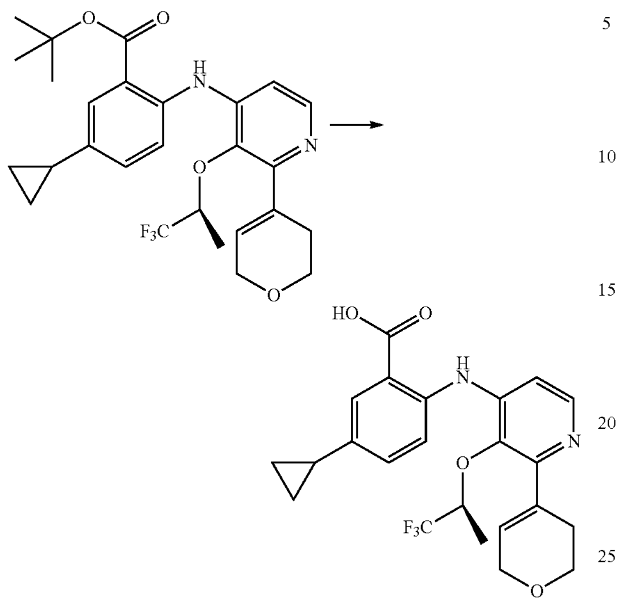

A mixture of tert-butyl (S)-5-cyclopropyl-2-((2-(3,6-dihydro-2H-pyran-4-yl)-3-((1,1,1-trifluoropropan-2-yl)oxy)

pyridin-4-yl)amino)benzoate (13 mg), dichloromethane (0.20 mL), and trifluoroacetic acid (70 μL) was stirred at room temperature for 1 hour. Water and ethyl acetate were added the mixture to which an aqueous sodium hydrogen carbonate solution was then added to make the pH=2.1. The organic layer was separated, washed with an aqueous sodium chloride solution, and dried over sodium sulfate. The solvent of the organic layer was distilled off under reduced pressure, and the obtained residue was purified by silica gel column chromatography (hexane:ethyl acetate gradient elution=90:10 to 0:100). Ethyl acetate and hexane were added to the obtained solid which was then stirred, and the solid matter was collected by filtration to obtain (S)-5-cyclopropyl-24(2-(3,6-dihydro-2H-pyran-4-yl)-3-((1,1,1-trifluoropropan-2-yl)oxy)pyridin-4-yl)amino)benzoic acid (13 mg) as a white solid.

1H-NMR (CDCl3) δ: 9.72 (br s, 1H), 8.18 (d, 1H, J=5.3 Hz), 7.83 (d, 1H, J=2.0 Hz), 7.43 (d, 1H, J=8.6 Hz), 7.28-7.19 (m, 2H), 6.36 (s, 1H), 4.61-4.46 (m, 1H), 4.33 (d, 2H, J=2.6 Hz), 3.95 (t, 2H, J=5.3 Hz), 2.79-2.49 (m, 2H), 1.99-1.84 (m, 1H), 1.39 (d, 3H, J=6.6 Hz), 1.03-0.93 (m, 2H), 0.75-0.64 (m, 2H).

LCMS (Method A)

MS (ESI m/z): 449 (M+H)

RT (min): 1.13

Example 2

Compound B was obtained from Compound A in the same manner as in Reference Example 2-5.

TABLE 8
| Example No. | A | B | LCMS Method | LCMS RT (min) | LCMS MS (M + H) | NMR |
|---|---|---|---|---|---|---|
| 2-1 | 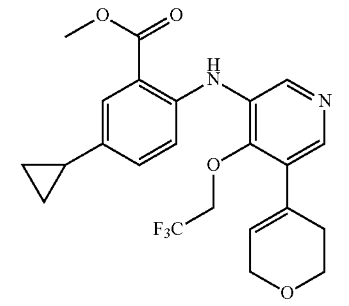 | 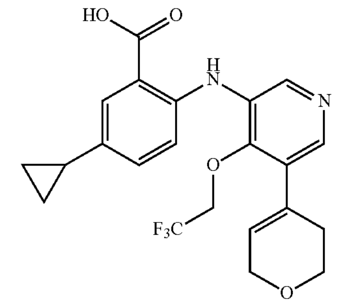 | A | 1.28 | 435 | 1H-NMR (CDCl3) δ: 9.32 (br s, 1H), 8.61 (s, 1H), 8.18 (s, 1H), 7.61 (d, 1H, J = 2.0 Hz), 7.21-7.14 (m, 1H), 7.05 (d, 1H, J = 8.8 Hz), 6.02 (s, 1H), 4.36-4.21 (m, 4H), 3.93 (t, 2H, J = 5.3 Hz), 2.52 (s, 2H), 1.94-1.63 (m, 1H), 0.99-.087 (m, 2H), 0.71-0.60 (m, 2H). |
| 2-2 | 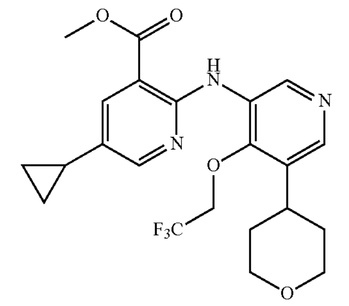 | 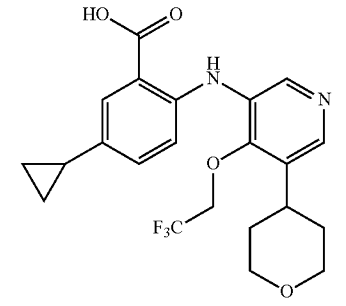 | A | 1.58 | 437 | 1H-NMR (DMSO-D6) δ: 13.65 (br s, 1H), 10.63 (br s, 1H), 8.43 (d, 1H, J = 7.9 Hz), 8.25 (d, 1H, J = 2.6 Hz), 7.92 (d, 1H, J = 2.6 Hz), 7.15 (t, 1H, J = 7.9 Hz), 6.94 (d, 1H, J = 7.9 Hz), 4.51 (q, 2H, J = 6.8 Hz), 4.05-3.91 (m, 2H), 3.49-3.38 (m, 2H), 3.25-3.10 (m, 1H), 2.03-1.87 (m, 1H), 1.75-1.61 (m, 4H), 0.98-0.88 (m, 2H), 0.72-0.62 (m, 2H). |
| 2-3 | 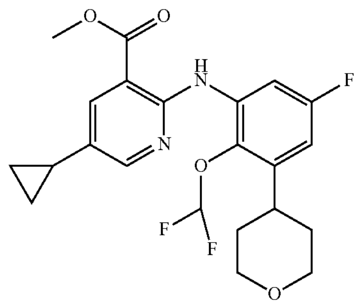 | 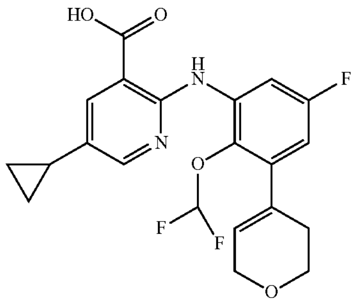 | A | 1.73 | 423 | 1H-NMR (DMSO-D6) δ: 13.81 (br s, 1H), 10.90 (br s, 1H), 8.48 (dd, 1H, J = 11.6, 3.1 Hz), 8.32 (d, 1H, J = 2.5 Hz), 7.96 (d, 1H, J = 2.5 Hz), 6.99 (t, 1H, J = 73.8 Hz), 6.56 (dd, 1H, J = 9.5, 3.0 Hz), 4.00-3.92 (m, 2H), 3.46-3.37 (m, 2H), 3.22-3.09 (m, 1H), 1.99-1.93 (m, 1H), 1.76-1.59 (m, 4H), 0.98-0.93 (m, 2H), 0.72-0.64 (m, 2H). |

TABLE 8-continued
| Example No. | A | B | LCMS Method | LCMS RT (min) | LCMS MS (M + H) | NMR |
|---|---|---|---|---|---|---|
| 2-4 | 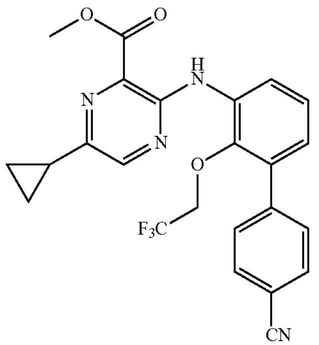 | 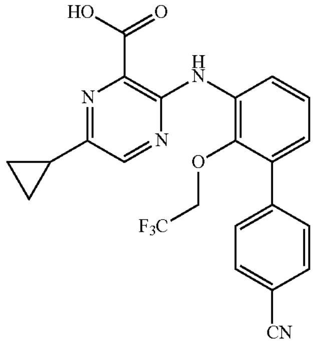 | A | 1.32 | 455 | 1H-NMR (DMSO-D6) δ: 13.46 (br s, 1H), 10.79 (br s, 1H), 8.50 (d, 1H, J = 7.3 Hz), 8.42 (s, 1H), 7.94 (d, 2H, J = 8.6 Hz), 7.74 (d, 2H, J = 7.9 Hz), 7.31 (t, 1H, J = 7.9 Hz), 7.99-7.65 (m, 1H), 4.13-4.08 (m, 2H), 2.23-2.10 (m, 1H), 1.00 0.89 (m, 4H). |
| 2-5 | 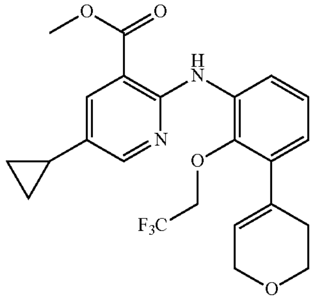 | 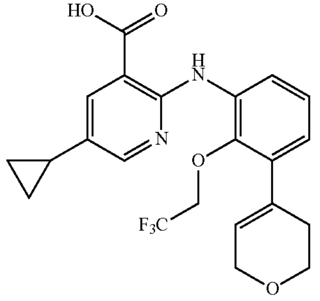 | A | 1.46 | 435 | 1H-NMR (DMSO-D6) δ: 13.60 (br s, 1H), 10.68 (br s, 1H), 8.54 (d, 1H, J = 7.9 Hz), 6.26 (d, 1H, J = 2.6 Hz), 7.92 (d, 1H, J = 2.6 Hz), 7.14 (t, 1H, J = 7.9 Hz), 6.83 (d, 1H, J = 7.6 Hz), 5.96 (br s, 1H), 4.40 (q, 2H, J = 9.0 Hz), 4.23-4.17 (m, 2H), 3.82 (t, 2H, J = 5.3 Hz), 2.46-2.37 (m, 2H), 2.00-1.88 (m, 1H), 0.99-0.89 (m, 2H), 0.72-0.64 (m, 2H). |
| 2-6 | 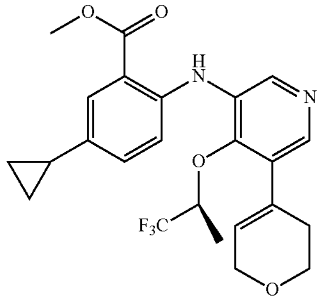 | 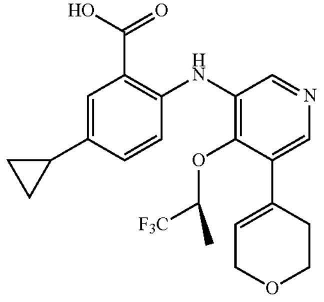 | A | 1.34 | 4.49 | 1H-NMR (DMSO-D6) δ: 13.21 (br s, 1H), 9.60 (br s, 1H), 8.54 (s, 1H), 8.12 (s, 1H), 7.65 (d, 1H, J = 2.0 Hz), 7.14 (dd, 1H, J = 5.6, 2.0 Hz), 7.03 (d, 1H, J = 8.86 Hz), 6.02 (s, 1H), 4.85-4.70 (m, 1H), 4.21 (s, 2H), 3.81 (t, 2H, J = 5.3 Hz), 2.42-2.24 (m, 2H), 1.99-1.85 (m, 1H), 1.26 (d, 3H, J = 5.9 Hz), 0.94-0.83 (m, 2H), 0.61-0.56 (m, 2H). |

TABLE 8-continued
| Example No. | A | B | LCMS Method | LCMS RT (min) | LCMS MS (M + H) | NMR |
|---|---|---|---|---|---|---|
| 2-7 | 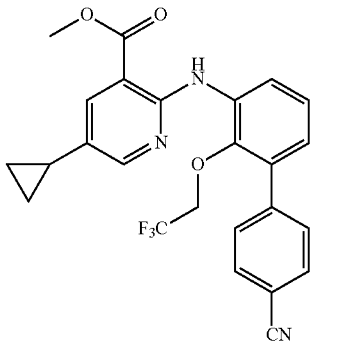 | 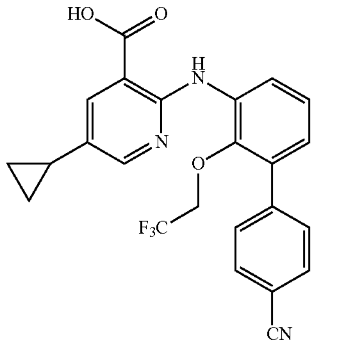 | A | 1.81 | 454 | 1H-NMR (DMSO-D6) δ: 10.95 (br s, 1H), 8.72 (d, 1H, J = 8.3 Hz), 8.30-8.24 (m, 1H), 7.97-7.89 (m, 3H), 7.74 (d, 2H, J = 8.3 Hz), 7.29 (t, 1H, J = 7.9 Hz), 7.01 (d, 1H, J = 7.9 Hz), 4.13 (q, 2H, J = 9.0 Hz), 2.02-1.88 (m, 1H), 0.98-0.90 (m, 2H), 0.74-0.64 (m, 2H). |
| 2-8 | 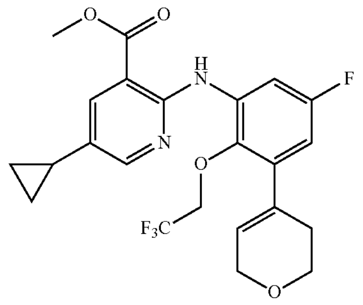 | 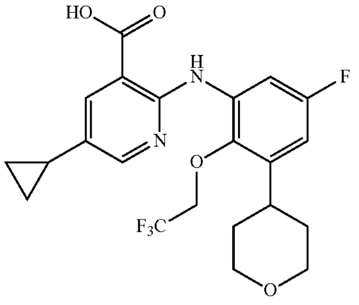 | A | 1.80 | 455 | 1H-NMR (DMSO-D6) δ: 10.97 (br s, 1H), 8.47 (dd, 1H, J = 11.9, 3.3 Hz), 6.31 (d, 1H, J = 2.6 Hz), 7.95 (d, 1H, J = 2.6 Hz), 6.74 (dd, 1H, J = 9.6, 3.0 Hz), 4.54 (q, 2H, J = 9.0 Hz), 3.97 (d, 2H, J = 11.2 Hz), 3.52-3.10 (m, 3H), 2.00-1.91 (m, 1H), 1.75-1.57 (m, 4H), 0.98-0.92 (m, 2H), 0.72-0.66 (m, 2H). |
| 2-9 | 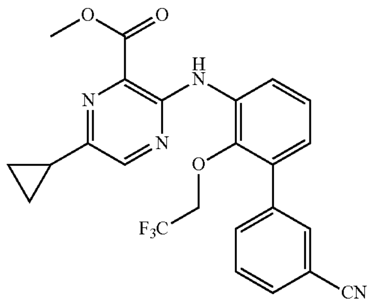 | 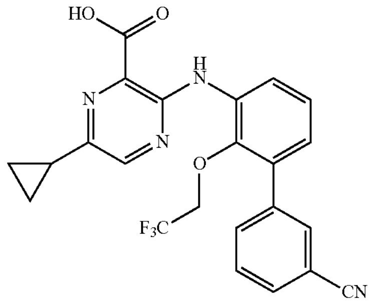 | A | 1.81 | 455 | 1H-NMR (DMSO-D6) δ: 10.73 (br s, 1H), 8.51 (d, 1H, J = 8.6 Hz), 8.45 (s, 1H), 8.00 (s, 1H), 7.94-7.84 (m, 2H), 7.68 (t, 1H, J = 7.9 Hz), 7.31 (t, 1H, J = 6.3 Hz), 7.10 (d, 1H, J = 7.3 Hz), 4.15 (q, 2H, J = 9.8 Hz), 2.24-2.10 (m, 1H), 1.03-0.88 (m, 4H). |

TABLE 8-continued
| Example No. | A | B | LCMS Method | LCMS RT (min) | LCMS MS (M + H) | NMR |
|---|---|---|---|---|---|---|
| 2-10 | 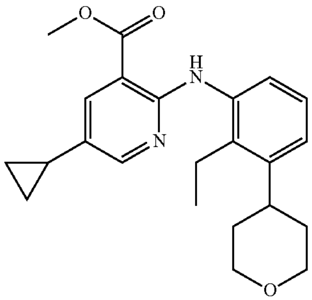 | 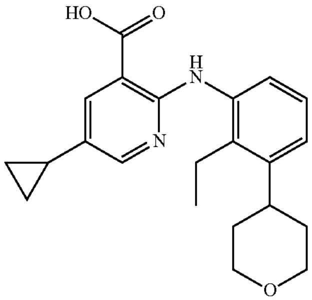 | A | 1.11 | 367 | 1H-NMR (CDCl3) δ: 9.68 (br s, 1H), 8.19 (d, 1H, J = 2.5 Hz), 7.97 (d, 1H, J = 2.6 Hz), 7.64 (d, 1H, J = 7.9 Hz), 7.23 (d, 1H, J = 7.9 Hz), 7.10 (d, 1H, J = 7.9 Hz), 4.11 (dd, 2H, J = 11.2, 4.6 Hz), 3.57 (t, 2H, J = 11.2 Hz), 3.03 (t, 1H, J = 11.8 Hz), 2.77 (q, 2H, J = 7.5 Hz), 2.02-1.60 (m, 9H), 1.35-1.09 (m, 3H), 1.04-0.86 (m, 2H), 0.74-0.67 (m, 2H). |
| 2-11 | 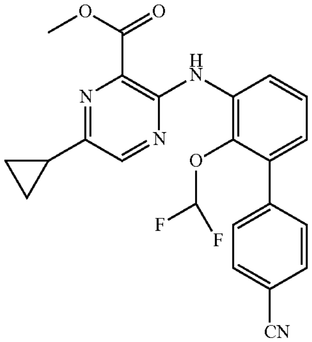 | 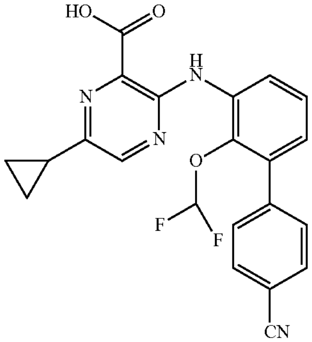 | A | 1.74 | 423 | 1H-NMR (DMSO-D6) δ: 13.58 (br s, 1H), 10.75 (br s, 1H), 8.55 (dd, 1H. J = 6.5, .1.3 Hz), 8.47 (s, 1H), 7.95 (s, 2H, J = 8.5 Hz), 7.72 (d, 2H, J = 8.5 Hz), 7.44 (t, 1H, J = 8.0 Hz), 7.14 (d, 1H, J = 8.0 Hz), 6.65 (t, 1H, J = 73.2 Hz), 2.22-2.14 (m, 1H), 1.01-0.92 (m, 4H). |
| 2-12 | 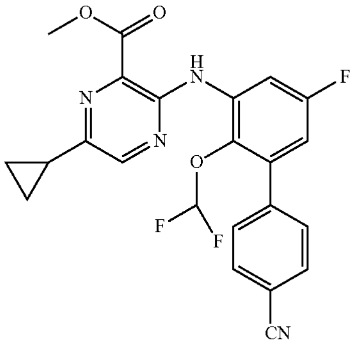 | 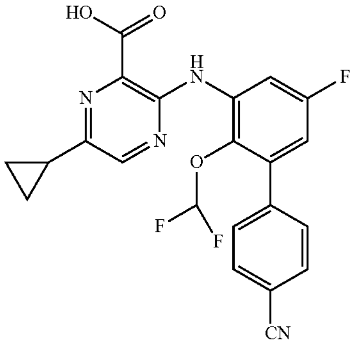 | A | 1.81 | 441 | 1H-NMR (DMSO-D6) δ: 11.15 (br s, 1H), 8.57-8.51 (m, 2H), 7.96 (d, 2H, J = 8.5 Hz), 7.74 (d, 2H, J = 8.0 Hz), 7.02 (dd, 1H, J = 8.9, 3.1 Hz),. 6.66 (t, 3H, J = 73.2 Hz), 2.28 - 2.08 (m, 1H), 1.00-0.95 (m, 4H). |

TABLE 8-continued
| Example No. | A | B | LCMS Method | LCMS RT (min) | LCMS MS (M + H) | NMR |
|---|---|---|---|---|---|---|
| 2-13 | 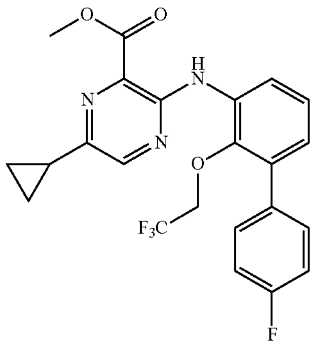 | 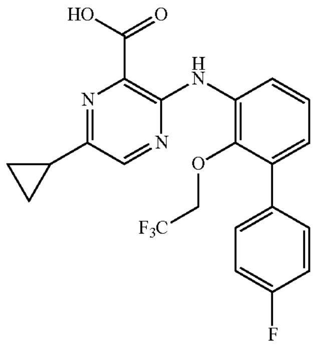 | A | 1.94 | 448 | 1H-NMR (DMSO-D6) δ: 13.44 (br s, 1H), 10.67 (br s., 1H), 8.48-8.42 (m, 2H), 7.60-7.55 (m 2H), 7.34-7.24 (m, 3H), 7.03 (d, 1H. J = 7.6 Hz), 4.08 (q, 2H, J = 8.8 Hz), 2.20-2.13 (m , 1H), 1.00-0.89 (m, 4H) |
| 2-14 | 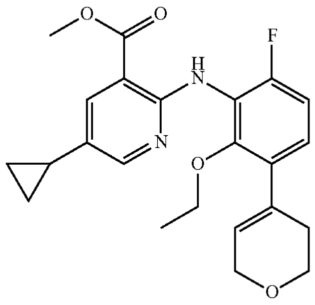 | 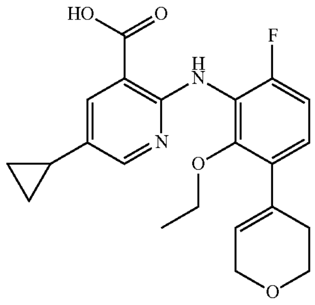 | A | 1.33 | 399 | 1H-NMR (DMSO-D6) δ: 13.55 (br s, 1H), 9.40 (br s, 1H), 8.08 (d, 1H, J = 2.3 Hz), 7.84 (d, 1H, J = 2.3 Hz), 7.09-6.95 m, 2H), 5.93 (br s, 1H ), 4.23-4.17 (m, 2H), 3.79 (t, 2H, J = 5.3 Hz), 3.72 (q, 2H, J = 6.9 Hz), 2.47-2.37 (m, 2H), 1.93-1.84 (m, 1H), 1.13 (t, 3H, J = 7.1 Hz), 0.94-0.86 (m, 2H), 0.67-0.60 (m, 2H) |
| 2-15 | 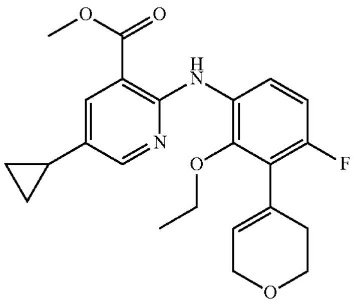 | 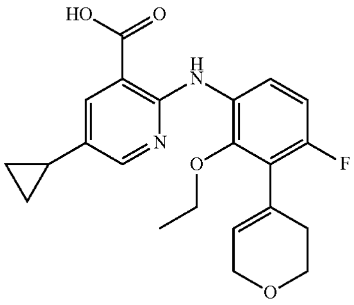 | A | 1.68 | 399 | 1H-NMR (DMSO-D6) δ: 11.12 (br s, 1H). 8.63 (dd, 1H, J = 9.2, 6.6 Hz), 8.21-8,19 (m, 1H), 7.89 (d, 1H, J = 2.6 Hz), 6.94 (t, 1H, J = 9.2 Hz), 5.87 (br s,1H), 4.25-4.19 (m, 2H), 3.88 (q, 2H, J = 6.9 Hz), 3.83 (t., 2H, J = 5.3 Hz), 2.42-2.30 (m, 2H), 1.97-1.85 (m, 1H), 1.37 (t. 2H, J = 6.9 Hz), 0.97-0.87 (m, 2H), 0.69-0.60 (m, 2H). |

TABLE 8-continued
| Example No. | A | B | LCMS Method | LCMS RT (min) | LCMS MS (M + H) | NMR |
|---|---|---|---|---|---|---|
| 2-16 | 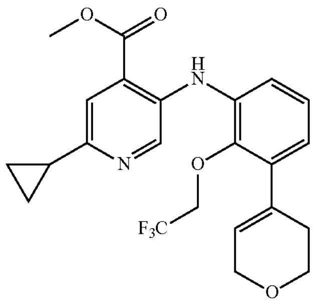 | 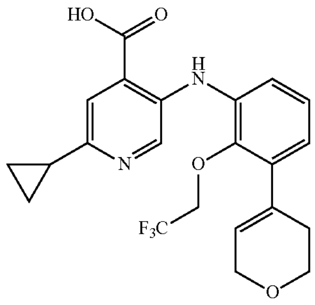 | A | 1.18 | 435 | 1H-NMR (DMSO-D6) δ: 13.81 (br s, 1H), 9.18 (br s, 1H), 8.48 (s, 1H), 7.63 (s, 1H), 7.36 (d, 1H, J = 7.3 Hz), 7.13 (t, 1H, J = 7.9 Hz), 6.90 (d, 1H, J = 7.6 Hz), 5.97 (br s, 1H), 4.38 (q, 2H, J = 9.0 Hz), 4.25-4.17 (m, 2H), 3.81 (t, 2H, J = 5.3 Hz), 2.46-2.37 (m, 2H), 2.16-2.03 (m, 1H), 0.95-0.78 (m, 4H). |
| 2-17 | 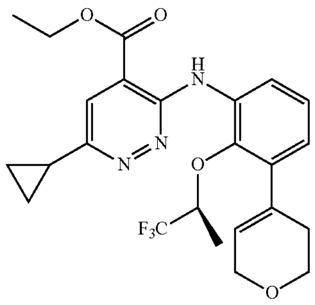 | 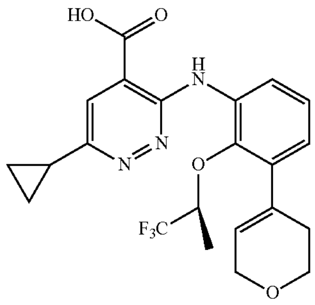 | A | 1.09 | 452 | 1H-NMR (DMSO-D6) δ: 10.27 (br s, 1H), 8.32 (d, 1H, J = 7.3 Hz), 7.79 (s, 1H), 7.17 (t, 1H, J = 8.3 Hz), 7.02 (d, 1H, J = 6.5 Hz), 4.84-4.65 (m, 1H), 4.08-3.89 (m, 2H) 3.49-3.06 (m, 3H), 2.36-2.17 (m, 1H), 1.86-1.54 (m, 4H), 1.30 (d, 3H, J = 6.6 Hz), 1.09-0.92 (m, 4H). |

Example 3

Compound C was obtained from Compound A and Compound B in the same manner as in Example 1-2.

TABLE 9
| Example No. | A | B | C | LCMS Method | LCMS RT (min) | LCMS MS (M + H) | NMB |
|---|---|---|---|---|---|---|---|
| 3-1 | 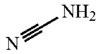 | 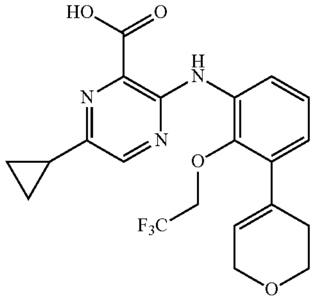 | 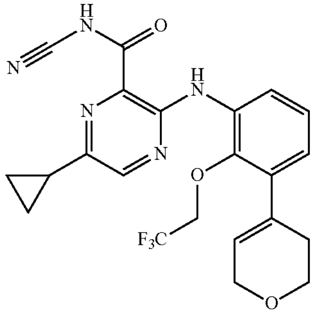 | A | 1.77 | 460 | 1H-NMR (DMSO-D6) δ: 10.37 (br s, 1H), 8.63 (s, 1H,), 8.24 (dd, 1H, J = 7.9, 1.3 Hz), 7.18 (t, 1H, J = 7.9 Hz), 6.94 (dd, 1H, J = 7.9. 1.3 Hz), 5.98 (br s, 1H), 4.43 (q, 2H, J = 9.0 Hz), 4.25-4.17 (m, 2H), 3.82 (t, 2H, J = 5.3 Hz), 2.46-2.37 (m, 2H), 2.22-2.13 (m, 1H), 1.12-0.92 (m, 4H). |
| 3-2 | 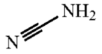 | 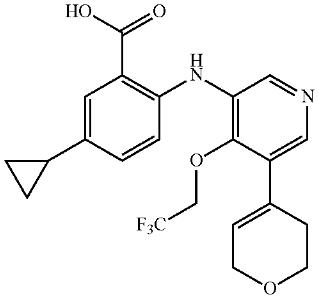 | 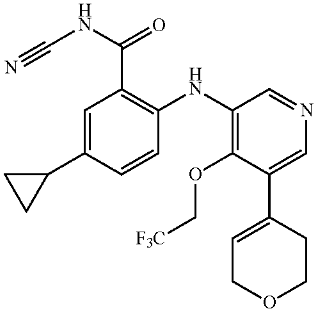 | A | 1.13 | 459 | 1H-NMR (DMSO-D6) δ: 10.66 (br s, 1H), 8.50 (s, 1H), 8.65 (s, 1H), 2.65 (s, 1H), 2.02 (s, 2.10, 6.03 (s, 1H), 4.55 (q, 3H, J = 9.0 Hz), 4.22 (s, 2H), 3.81 (t, 2H, J = 5.0 Hz), 2.43 (s, 2H), 1.93-1.80 (m, 1H), 0.93-0.80 (m, 2H), 0.64-0.52 (m, 2H). |
| 3-3 | 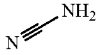 | 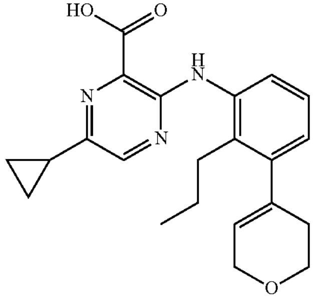 | 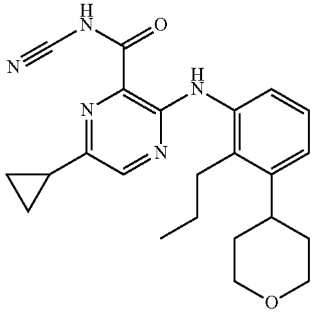 | A | 1.79 | 408 | 1H-NMR (DMSO-D6) δ: 9.93 (br s, 1H), 8.40 (s, 1H,), 7.65 (d, 1H, J = 7.8 Hz), 7.21-7.07 (m, 2H), 4.01-3.90 (m, 2H), 3.57-3.23 (m, 2H), 3.08-2.93 (m, 1H), 2.74-2.61 (m, 2H), 2.18-2.08 (m, 1H), 1.78-1.44 (m, 3H), 1.05-0.91 (m, 1H). |

TABLE 9-continued
| Example No. | A | B | C | LCMS Method | LCMS RT (min) | LCMS MS (M + H) | NMB |
|---|---|---|---|---|---|---|---|
| 3-4 | 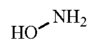 | 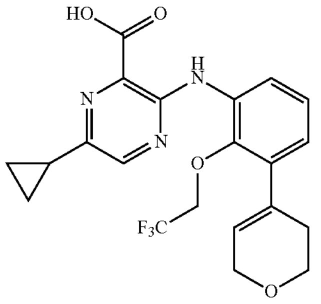 | 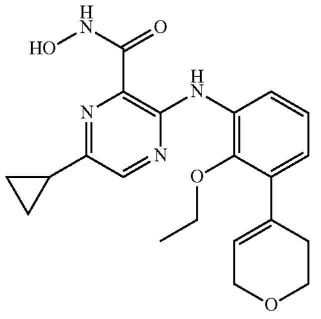 | A | 1.80 | 451 | 1H-NMR (DMSO-D6) δ: 11.34 (br s, 1H), 10.98 (br s, 1H), 9.24 (br s, 1H), 3.57 (s, 1H), 5.31 (d, 1H, J = 7.8 Hz), 7.14 (t, 1H, J = 7.9 Hz), 6.88 (d, 1H, J = 7.3 Hz), 6.95 (br s, 1H), 4.42 (q, 2H, J = 9.0 Hz), 4.24-4.16 (m, 2H), 3.62 (t, 2H, J = 5.3 Hz), 2.46-2.36 (m, 2H), 2.16-2.04 (m, 1H), 1.12-1.01 (m, 2H), 0.97-0.82 (m, 2H). |
| 3-5 | 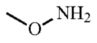 | 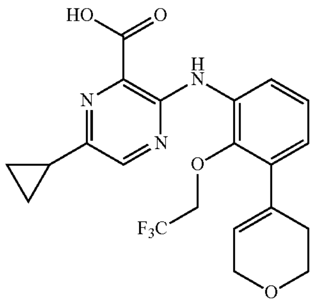 | 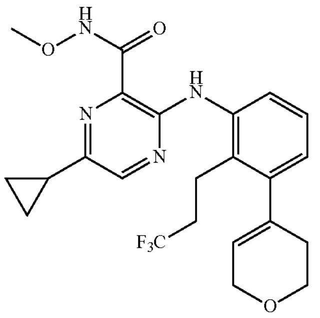 | A | 1.50 | 465 | 1H-NMR (DMSO-D6) δ: 11.36 (br s, 1H), 10.87 (br s, 1H), 8.40 (s, 1H, 8.30 (d, 1H, J = 7.9 Hz), 7.15 (t, 1H, J = 7.9 Hz), 6.88 (d, 1H, J = 7.9 Hz), 5.97 (br s, 1H), 4.41 (q, 2H, J = 9.0 Hz), 4.26-4.16 (m, 2H), 3.82 (t, 2H, J = 5.3 Hz), 3.73 (s, 3H), 2.46-2.37 (m, 2H), 2.18-2.03 (m, 1H), 1.11-1.01 (m, 2H), 0.98-0.88 (m, 2H). |
| 3-6 | 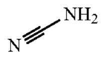 | 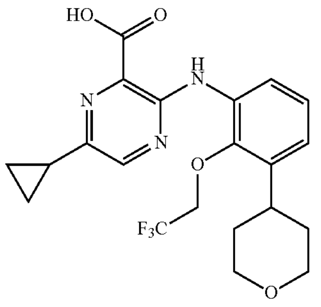 | 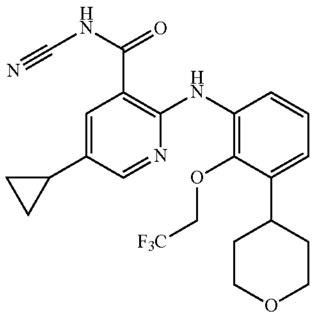 | A | 1.19 | 461 | 1H-NMR (DMSO-D6) δ: 11.73 (br s, 1H), 8.39 (d, 1H, J = 7.9 Hz), 8.03 (s, 1H), 8.04 (d, 1H, J = 2.6 Hz), 7.98 (d, 1H, J = 2.6 Hz), 7.98 (t, 1H, J = 7.9 Hz), 6.95 (s, 1H, J = 7.9 Hz), 4.52 (q, 2H, J = 9.8 Hz), 4.03-3.91 (m, 2H), 3.49-3.12 (m, 3H), 1.96-1.78 (m, 1H), 1.75-1.57 (m, 4H), 0.97-0.78 (m, 2H), 0.67-0.54 (m, 2H). |

TABLE 9-continued
| Example No. | A | B | C | LCMS Method | LCMS RT (min) | LCMS MS (M + H) | NMB |
|---|---|---|---|---|---|---|---|
| 3-7 | 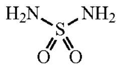 | 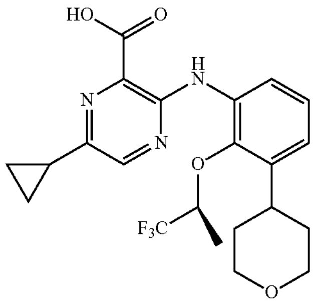 | 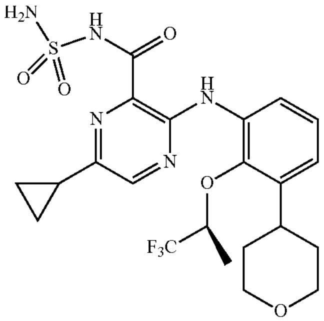 | A | 1.82 | 530 | 1H-NMR (DMSO-D6) δ: 11.22 (br s, 1H), 10.05 (br s, 1H), 8.43 (s, 1H), 7.83 (d, 1H, J = 7.9 Hz), 7.68 (br s, 2H), 7.21-6.33 (m, 2H), 4.75-4.56 (m, 1H), 4.07-3.88 (m, 3H), 3.52-2.28 (m, 2H), 3.27-3.08 (m, 1H), 2.23-2.06 (m, 3H), 1.65-1.52 (m, 4H), 1.33 (d, 3H, J = 5.6 Hz), 1.15-0.88 (m, 4H). |
| 3-8 | 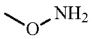 | 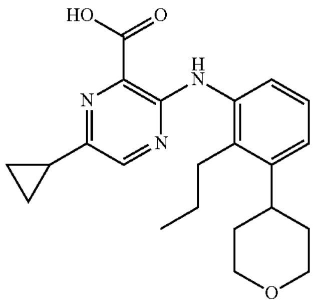 | 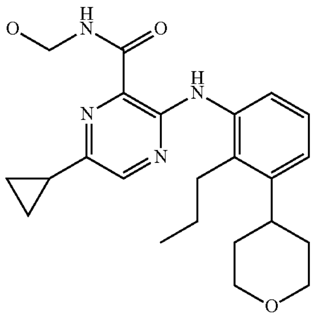 | A | 1.79 | 411 | 1H-NMR (DMSO-D6) δ: 11.87 (s, 1H), 10.44 (s, 1H,), 8.28 (s, 1H), 7.15 (d, 1H, J = 7.3 Hz), 7.16 (t, 1H, J = 7.8 Hz), 7.83 (d, 1H, J = 7.3 Hz), 3.95 (dd, 2H, J = 11.2, 3.3 Hz), 3.74 (s, 2H), 3.48 (t, 2H, J = 10.9 Hz), 3.08-2.93 (m, 1H), 2.88 (t, 2H, J = 7.9 Hz), 2.11-2.93 (m, 1H), 1.79-1.44 (m, 6H), 1.06-0.87 (m, 7H). |
| 3-9 | 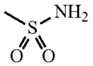 | 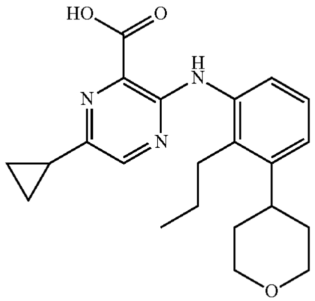 | 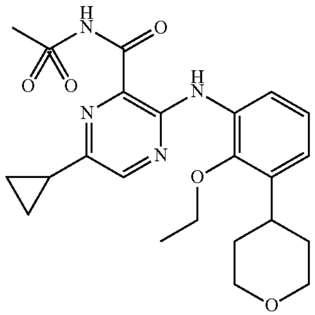 | A | 1.74 | 459 | 1H-NMR (DMSO-D6) δ: 11.51 (br s, 1H), 9.97 (br s, 1H), 8.37 (s, 1H), 7.04 (d, 1H, J = 7.3 Hz), 7.18 (t, 1H, J = 7.0 Hz), 7.08 (d, 1H, J = 7.9 Hz), 4.00-3.92 (m, 2H), 3.49 (t, 2H, J = 10.9 Hz), 3.39 (s, 3H), 3.09-2.94 (m, 1H), 2.76-2.52 (m, 2H), 2.14-2.08 (m, 1H), 1.83-1.41 (m, 1H), 1.13-0.88 (m, 2H). |

TABLE 9-continued
| Example No. | A | B | C | LCMS Method | LCMS RT (min) | LCMS MS (M + H) | NMB |
|---|---|---|---|---|---|---|---|
| 3-10 | 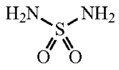 | 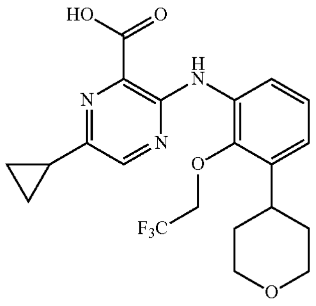 | 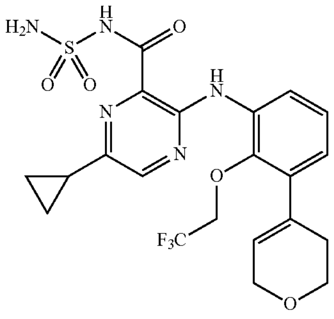 | A | 1.83 | 514 | 1H-NMR (DMSO-D6) δ: 11.23 (br s, 1H), 10.48 (br s, 1H), 8.46 (s, 1H), 8.16 (d, 1H, J = 7.3 Hz), 7.63 (br s, 2H), 7.16 (t, 1H, J = 7.9 Hz), 5.93 (d, 1H, J = 0.6 Hz), 5.97 (s, 1H), 4.43 (q, 2H, J = 9.0 Hz), 4.21 (d, 2H, J = 2.6 Hz), 3.82 (t, 2H, J = 5.3 Hz), 2.42 (s, 2H), 2.21-2.13 (m, 1H), 1.18-0.88 (m, 4H). |
| 3-11 | 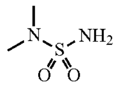 | 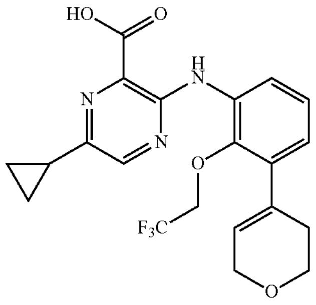 | 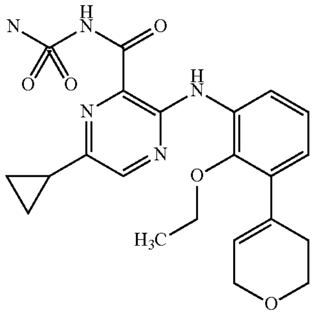 | A | 1.89 | 542 | 1H-NMR (DMSO-D6) δ: 11.20 (br s, 1H), 10.49 (br s, 1H), 8.55-8.40 (m, 1H), 8.37-8.23 (m, 1H), 7.18 (t, 1H, J = 7.9 Hz), 5.91 (d, 1H, J = 7.3 Hz), 5.96 (s, 1H), 4.44 (q, 2H, J = 9.0 Hz), 4.20 (d, 2H, J = 2.6 Hz), 3.82 (t, 2H, J = 8.3 Hz). 2.90 (s, 6H), 2.41 (s, 2H), 2.24-2.10 (m, 1H), 1.18-0.99 (m, 4H). |
| 3-12 | 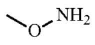 | 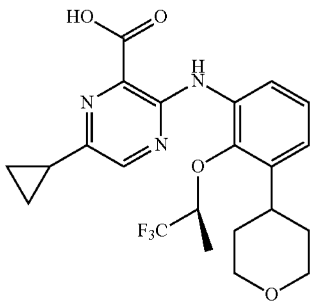 | 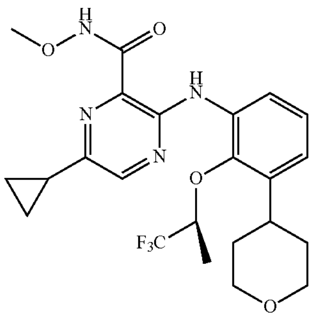 | A | 1.80 | 481 | 1H-NMR (DMSO-D6) δ: 11.37 (s, 1H), 10.53 (s, 1H), 8.37 (s, 1H), 8.03 (d, 1H, J = 7.9 Hz), 7.14 (t, 1H, J = 8.3 Hz), 7.01 (d, 1H, J = 7.3 Hz), 4.78-4.83 (m, 1H), 3.98 (t, 2H, J = 11.2 Hz), 3.74 (s, 3H), 3.48-3.85 (m. 2H), 3.26-309 (m, 1H), 2.17-2.04 (m, 1H), 1.81-3.53 (m, 4H), 1.33 (d, 3H, J = 6.6 Hz), 1.05-0.91 (m, 4H). |

TABLE 9-continued
| Example No. | A | B | C | LCMS Method | LCMS RT (min) | LCMS MS (M + H) | NMB |
|---|---|---|---|---|---|---|---|
| 3-13 | 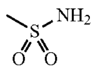 | 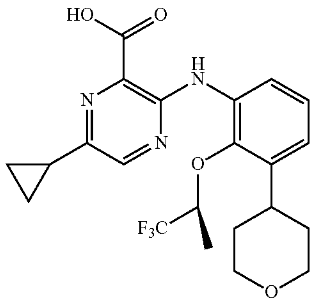 | 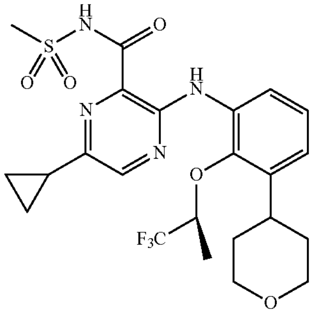 | A | 1.79 | 529 | 1H-NMR (DMSO-D6) δ: 11.57 (br s, 1H), 10.18 (br s, 1H), 8.47 (s, 1H), 7.99 (dd, 1H, J = 7.8, 1.2 Hz), 7.16 (t, 1H, J = 7.9 Hz), 7.07 (dd, 1H, J = 7.8, 1.3 Hz), 4.79-4.70 (m, 1H), 3.98 (t, 2H, J = 10.9 Hz), 3.47-3.38 (m, 2H), 3.38 (s, 3H), 3.23-3.08 (m, 1H), 2.21-2.12 (m, 1H), 1.77-1.63 (m, 4H), 1.30 (d, 3H, J = 6.8 Hz), 1.16-0.91 (m, 4H). |
| 3-14 | 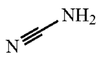 | 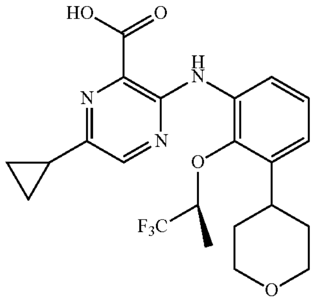 | 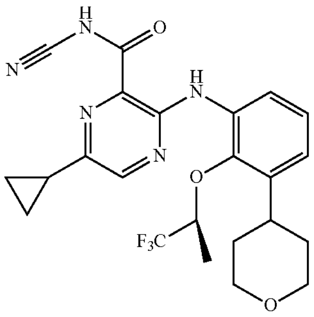 | A | 1.77 | 475 | 1H-NMR (DMSO-D6) δ: 10.07 (br s, 1H), 8.50 (s, 1H), 7.96 (dd, 1H, J = 7.9, 1.3 Hz), 7.16 (t, 1H, J = 7.6 Hz), 7.07 (d, 1H, J = 6.8 Hz), 4.80-4.87 (m, 1H), 4.03-3.97 (m, 2H), 3.48-3.37 (m, 2H), 3.22-3.09 (m, 1H), 2.20-2.12 (m, 1H), 177-1.63 (m, 4H), 1.30 (d, 3H, J = 6.8 Hz), 1.11-0.91 (m, 4H). |
| 3-15 | 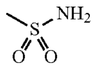 | 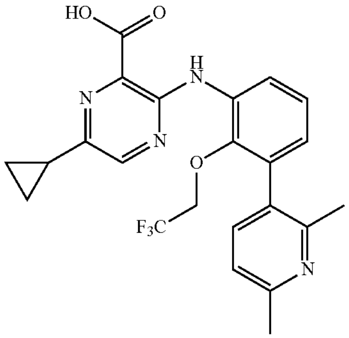 | 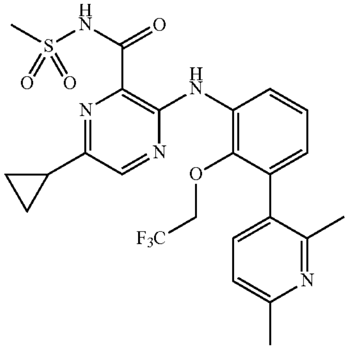 | A | 1.23 | 535 | 1H-NMB (CDCl3) δ: 10.54 (s, 1H), 8.45-8.31 (m, 2H), 7.48 (d, 1H, J = 7.9 Hz), 7.29-7.19 (m, 1H), 7.08 (d, 1H, J = 7.9 Hz), 6..93 (d, 1H, J = 9.2 Hz), 3.87-3.67 (m, 2H), 3.42 (s, 3H), 2.60 (s, 3H), 2.46 (s, 3H), 2.15-2.00 (m, 1H), 1.10-0.83 (m, 4H). |

TABLE 9-continued
| Example No. | A | B | C | LCMS Method | LCMS RT (min) | LCMS MS (M + H) | NMB |
|---|---|---|---|---|---|---|---|
| 3-16 | 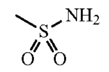 | 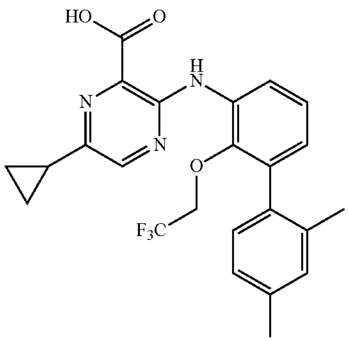 | 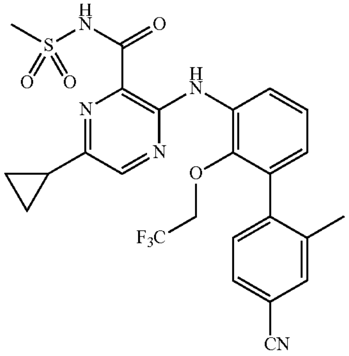 | A | 1.89 | 546 | 1H-NMB (CDCl3) δ: 10.54 (br s, 1H), 9.94 (br s, 1H), 5.46-5.32 (m, 2H), 7.66-7.58 (m, 2H), 7.38 (d, 1H), J = 7.9 Hz), 7.34-7.21 (m, 1H). 6.91 (dd, 1H, J - 7.8, 1.2 Hz), 3.97-3.54 (m, 2H), 3.42 (s, 3H), 2.27 (s, 3H), 2.13-2.05 (m, 1H) 1.19-061 (m, 4H). |
| 3-17 | 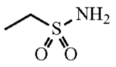 | 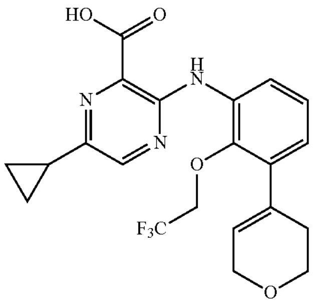 | 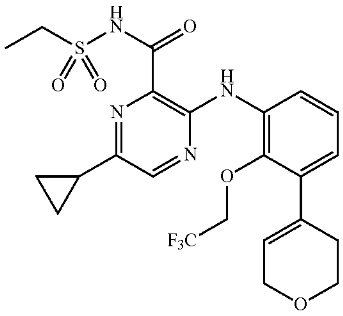 | A | 1.81 | 527 | 1H-NMR (DMSO-D6) δ: 11.53 (br s, 1H), 10.49 (br s, 1H), 8.48 (s, 1H), 8.27 (d, 1H, J = 8.6 Hz), 7.17 (t, 1H, J = 7.8 Hz), 8.52 (d, 1H, J = 7.9 Hz), 5.98 (s, 1H), 4.43 (q, 2H, J = 9.0 Hz), 4.21 (d, 2H, J = 2.6 Hz), 3.82 (t, 2H, J = 5.3 Hz), 3.61-3.46 (m, 2H), 2.42 (s, 2H), 2.20-2.15 (m, 1H), 1.27 (t, 3H, J = 7.5 Hz), 1.18-0.92 (m, 4H) |
| 3-18 | 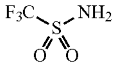 | 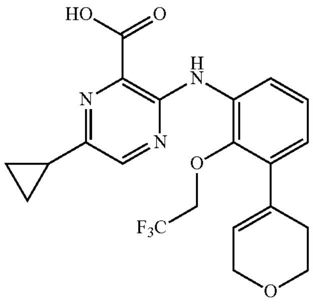 | 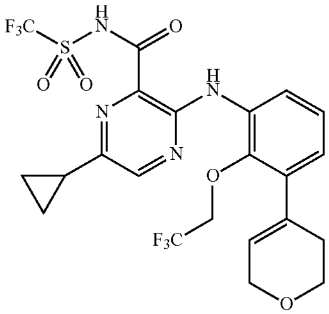 | A | 1.73 | 567 | 1H-NMR (DMSO-D6) δ: 10.96 (br s, 1H), 8.23 (d, 1H, J = 7.9 Hz), 3.20 (s, 1H), 7.12 (t, 1H, J = 7.9 Hz), 6.34 (dd, 1H, J = 7.6, 1.7 Hz), 5.94 (br s, 1H), 4.38 (q, 2H, J = 2.0 Hz), 4.25-4.15 (m, 2H), 3.81 (t, 2H, J = 5.3 Hz), 2.46-2.36 (m, 2H), 2.16-2.04 (m, 1H), 0.95-0.85 (m, 4H). |

TABLE 9-continued
| Example No. | A | B | C | LCMS Method | LCMS RT (min) | LCMS MS (M + H) | NMB |
|---|---|---|---|---|---|---|---|
| 3-19 | 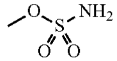 | 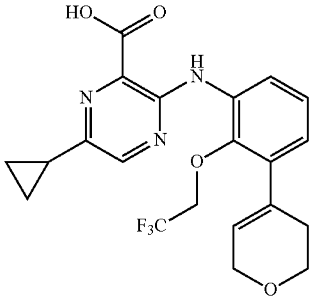 | 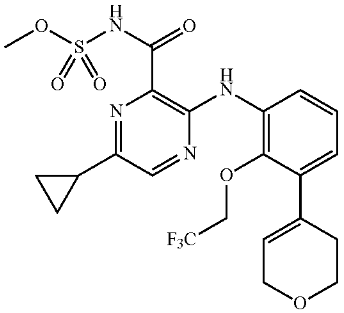 | A | 1.81 | 529 | 1H-NMR (DMSO-D6) δ: 10.84 (br s, 1H), 9.49 (br s, 1H), 8.42 (s, 1H), 8.21 (d, 1H, J = 7.6 Hz), 7.21-7.10 (m, 1H), 6.98-6.55 (m, 1H), 6.97 (br s, 1 Hz) 4.43 (q, 2H, J = 9.0 Hz), 4.25-4.17 (m, 2H), 3.82 (t, 2H, J = 5.3 Hz), 3.46 (s, 3H), 2.46-2.37 (m, 2H), 2.24-2.10 (m, 1H), 1.15-0.85 (m, 4H). |
| 3-20 | 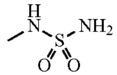 | 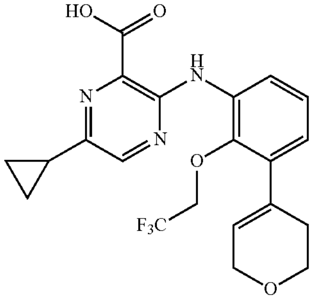 | 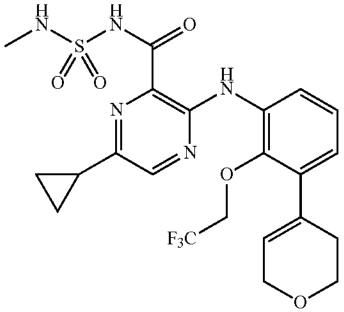 | A | 1.75 | 528 | 1H-NMR (DMSO-D6) δ: 11.18 (s, 1H), 10.38 (br s, 1H), 8.47 (br s, 1H), 8.16 (d, 1H, J = 7.3 Hz), 7.75 (br s, 1H), 717 (t, 1H, J = 7.9 Hz), 6 93 (d, 1H, J = 23 Hz), 5.97 (br s, 1H), 4.42 (q, 2H, J = 9.0 Hz), 4.27-4.15 (m, 2H), 3.52 (t, 2H J = 5.8 Hz), 2.59 (s, 3H), 2.46-2.36 (m, 2H), 224-209 (m, 1H) 1.18-105 (m. 2H), 1.03-0.91 (m, 2H). |
| 3-21 | 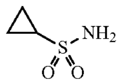 | 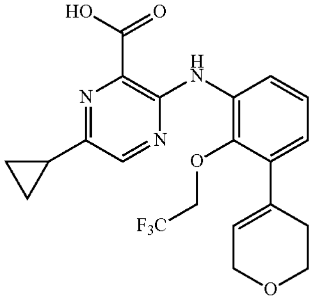 | 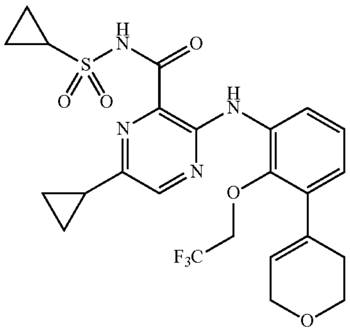 | A | 1.85 | 539 | 1H-NMR (DMSO-D6) δ: 11.53 (br s, 1H), 10.48 (br s, 1H), 8.50 (br s, 1H), 8.27 (d, 1H. J = 7.9 Hz), 7.18 (t, 1H, J = 8.3 Hz), 6.93 (d, 1H, J = 7.9 Hz), 5.96 (br s, 1 H), 4.43 (q, 2H, J = 9.0 Hz), 4.28-4.16 (m, 2H), 3.82 (t, 2H, J = 5.3 Hz), 3.17-3.02 (m, 1H), 2.48-2.37 (m, 3H), 2.35-2.32 (m, 1H), 1.33-0.59 (m, 3H). |

TABLE 9-continued
| Example No. | A | B | C | LCMS Method | LCMS RT (min) | LCMS MS (M + H) | NMB |
|---|---|---|---|---|---|---|---|
| 3-22 | 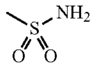 | 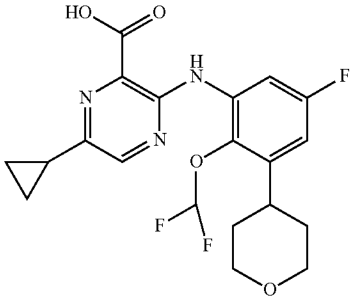 | 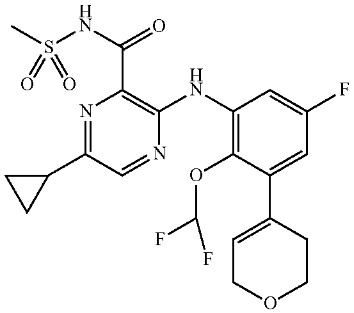 | A | 181 | 500 | 1H-NMR (DMSO-D6) δ: 12.04-11.66 (m, 3.51 (d, 1H, J = 8.6 Hz), 8.18 (d, 1H), 7.96 (d, 1H, J = 2.6 Hz), 7.11 (t, 1H, J = 74.0 Hz), 6.76 (d, 1H, J = 9.2 Hz), 4.00-3.87 (m, 2H), 3.48-3.38 (m, 2H), 3.34 (s, 3H), 3.25-3.12 (m, 1H), 2.04-1.89 (m, 1H), 1.79-1.62 (m, 4H), 0.93-0.62 (m, 4H). |
| 3-23 | 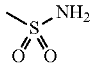 | 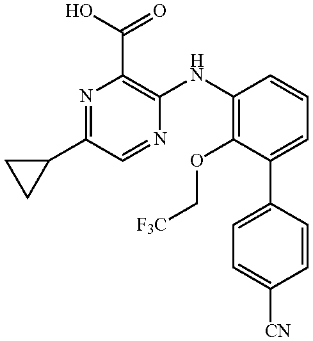 | 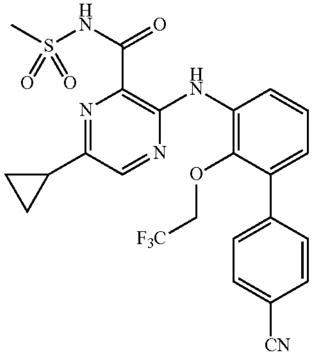 | A | 1.93 | 532 | 1H-NMR (CDCl3) δ: 10.58 (br s, 1H), 8.43-8.38 (m, 2H), 7.79-7.68 (m, 4H), 7.33-7.28 (m, 1H), 7.07 (d, 1H, J = 7.3 Hz), 3.53 (q, 2H, J = 8.4 Hz), 3.43 (s, 3H), 2.12-2.05 (m, 1H), 1.15-0.92 (m, 4H). |

TABLE 9-continued
| Example No. | A | B | C | LCMS Method | LCMS RT (min) | LCMS MS (M + H) | NMB |
|---|---|---|---|---|---|---|---|
| 3-24 | 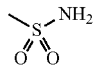 | 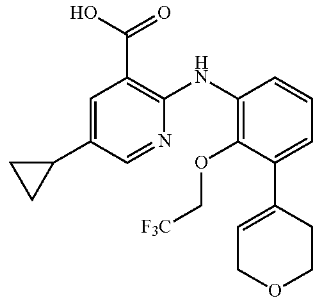 | 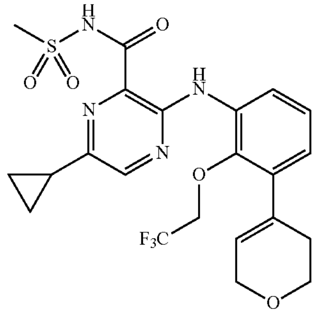 | A | 1.48 | 512 | 1H-NMR (CDCl3) δ: 10.33 (br s, 1H), 8.28-8.18 (m, 2H), 7.58 (s, 1H), 7.13 (t, 1H, J = 7.5 Hz), 6.87 (d, 1H, J = 6.8 Hz), 5.95 (s, 1H), 4.34-4.08 (m, 4H), 3.97 (t, 2H, J = 5.3 Hz). 3.38 (s, 3H) 2.55-2.43 (m ,2H), 1.50-1.78 (m, 1H), 1.04-0.82 (m, 2H), 0.72-0.60 (m, 2H). |
| 3-25 | 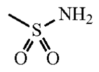 | 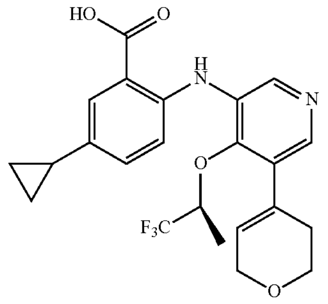 | 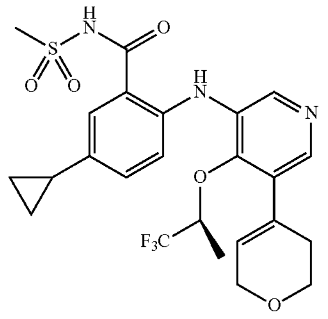 | A | 129 | 526 | 1H-NMR (CDCl3) δ: 8.90-8.87 (m, 1H), 8.28 (s, 1H), 8.12 (s, 1H), 7.38-7.30 (m, 1H), 7.20-7.11 (m, 1H), 7.11-6.98 (m, 1), 5.99 (s, 1H), 4.72-4.52 (m, 1H), 4.37-4.25 (m, 2H), 3.92 (t, 2H, J = 5.3 Hz), 3.40 (S, 3H), 2.58-2.34 (m, 2H), 1.98-1.65 (m, 1H), 1.38 (d, 3H, J = 5.8 Hz), 1.06-0.57 (m, 4H). |
| 3-26 | 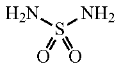 | 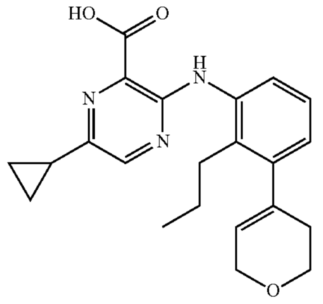 | 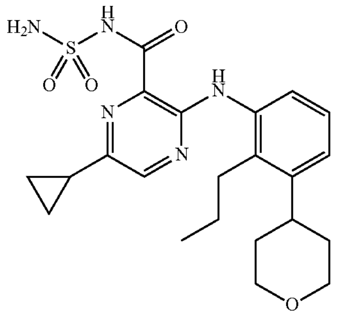 | A | 1.59 | 460 | 1H-NMR (CDCl3) δ: 10.20 (br s, 1H), 9.77 (br s, 1H), 8.26 (s, 1H), 7.52 (d, 1H, J = 7.9 Hz), 7.23 (d, 1H, J = 7.9 Hz), 7.14 (d, 1H, J = 7.3 Hz), 5.39 (s, 2H), 4.11 (d, 2H, J = 11.9 Hz), 3.56 (t, 2H, J = 1.16 Hz), 3.10-2.95 (m, 1H), 2.78-2.64 (m, 2H), 2.05-1.83 (m, 5H), 1.74-1.62 (m, 2H), 1.12-0.85 (m, 7H). |

TABLE 9-continued
| Example No. | A | B | C | LCMS Method | LCMS RT (min) | LCMS MS (M + H) | NMB |
|---|---|---|---|---|---|---|---|
| 3-27 | 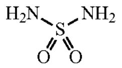 | 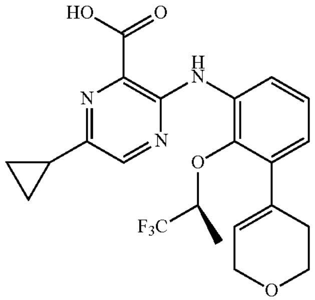 | 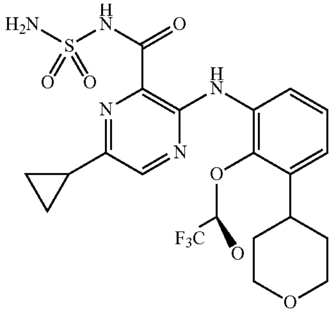 | A | 1.67 | 528 | 1H-NMR (CDCl3) δ: 10.46 (br s, 1H), 10.13 (br s, 1H), 8.35 (s, 1H), 8.25 (d, 2H, J = 7.9 Hz), 7.14 (t, 1H, J = 7.9 Hz), 6.99 (dd, 1H, J = 7.9, 1.3 Hz), 5.96 (s, 1H), 5.41 (br s, 2H), 4.62-4.53 (m, 1H), 4.31 (d, 2H, J = 2.6 Hz), 3.97-3.90 (m, 2H), 2.66-2.32 (m, 2H), 2.14-2.00 (m, 1H), 1.35 (d, 3H, J = 6.6 Hz), 1.15-1.00 (m, 2H), 1.00-0.81 (m, 2H). |
| 3-28 | 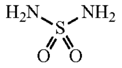 | 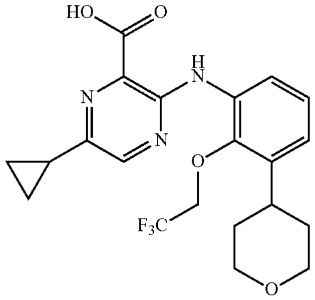 | 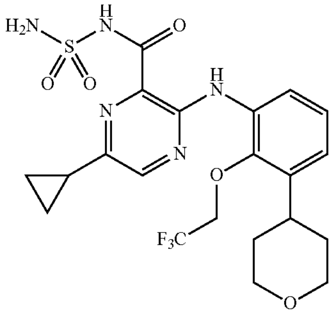 | A | 1.59 | 518 | 1H-NMR (CDCl3) δ: 10.30 (br s, 1H), 10.14 (br s, 1H), 8.36 (s, 7H), 8.08 (d, 1H, J = 7.9 Hz), 7.19 (t, 1H, J = 8.3 Hz), 7.03 (d, 1H, J = 6.6 Hz), 5.41 (br s, 2H), 4.25 (q, 2H, J = 8.4 Hz), 4.16-4.02 (m, 2H), 3.86 (d, 2H, J = 12.0, 2.7 Hz), 3.31-3.14 (m, 1H), 2.15-2.01 (m, 1H), 1.84-1.70 (m, 4H), 1.10-0.99 (m, 4H). |
| 3-29 | 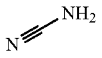 | 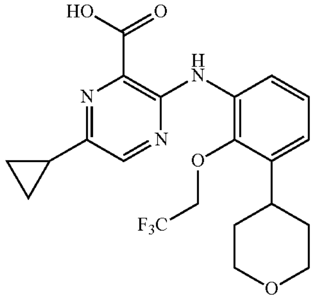 | 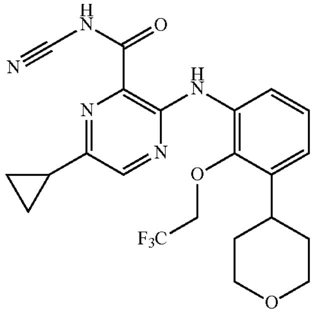 | A | 1.73 | 452 | 1H-NMR (DMSO-D6) δ: 10.41 (br s, 1H), 8.46 (br s, 1H), 8.11 (d, 1H, J = 7.3 Hz), 7.18, (t, 1H, J = 7.9 Hz), 7.03 (t, 1H, J = 7.3 Hz), 4.52 (q, 2H, J = 9.8 Hz), 4.03-3.92 (m, 2H), 3.56-3.10 (m, 3H), 2.23-2.09 (m, 1H), 1.75-1.81 (m, 4H), 1.11-0.90 (m, 4H). |

TABLE 9-continued
| Example No. | A | B | C | LCMS Method | LCMS RT (min) | LCMS MS (M + H) | NMB |
|---|---|---|---|---|---|---|---|
| 3-30 | 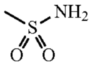 | 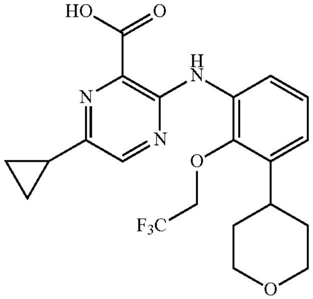 | 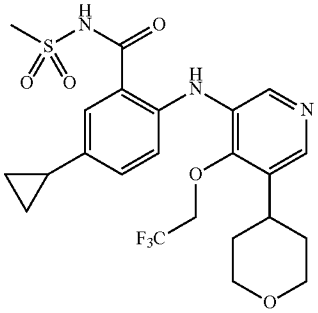 | A | 1.71 | 515 | 1H-NMR (DMSO-D6) δ: 11.59 (br s, 1H), 10.39 (br s, 1H), 8.49 (s, 1H), 8.15 (d, 1H, J = 7.3 Hz), 7.19 (t, 1H, J = 7.9 Hz), 7.04 (d, 1H, J = 7.9 Hz), 4.54 (d, 2H, J = 8.8 Hz), 3.98 (d, 2H, J = 10.8 Hz), 3.60-3.49 (m, 2H), 3.35 (s, 3H), 3.24-3.09 (m, 1H), 2.25-2.11 (m, 1H), 1.75-1.81 (m, 4H), 1.17-1.08 (m, 2H), 1.03-0.90 (m, 2H). |
| 3-31 | 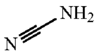 | 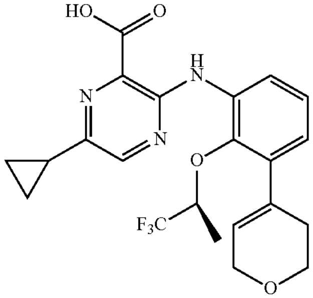 | 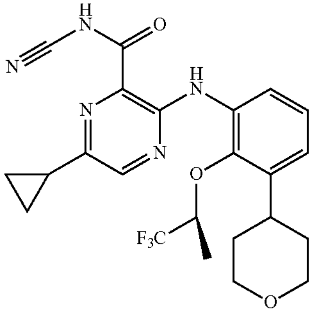 | A | 1.82 | 474 | 1H-NMR (DMSO-D6) δ: 10.51 (br s, 1H), 8.45 (br s, 1H), 8.24 (d, 1H, J = 7.3 Hz), 7.15 (t, 1H, J = 7.9 Hz), 5.91 (d, 1H, J = 7.3 Hz), 5.95 (br s 1 H), 4.72-4.57 (m, 1H) 4.25-4.15 (m, 2H), 3.32 (t, 2H, J = 5.3 Hz), 2.47-2.34 (m, 2H), 2.21-2.09 (m, 1H), 1.29 (d, 3H, J = 7.3 Hz), 1.10-0.38 (m, 4H). |
| 3-32 | 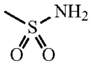 | 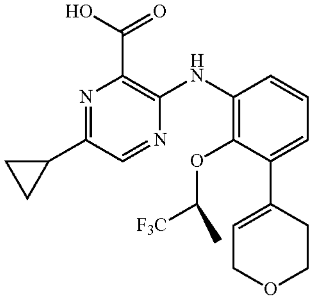 | 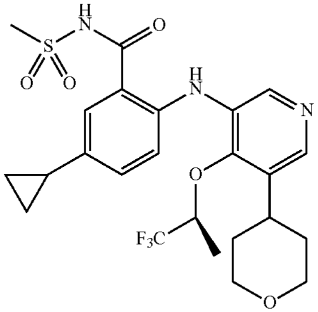 | A | 1.78 | 527 | 1H-NMR (DMSO-D6) δ: 11.58 (br s, 1H), 10.50 (br s, 1H), 5.48 (br s, 1H), 5.26 (d, 1H, J = 7.8 Hz), 7.16 (t, 1H, J = 7.9 Hz).<br>6.92 (d, IH, J = 7.3 Hz), 5.26 (br s, 1H), 4.74-4.57 (m, 1H), 4.24-4.15 (m, 2H), 3.82 (t, 2H, J = 5.3 Hz).3.39 (s, 3 H), 2.47-2.35 (m, 2H), 2.25-2.00 (m, 1H), 1.29 (d, 3H, J = 7.3 Hz), 1.17-1.04 (m, 2H), 1.00-0.91 (m, 2H). |

TABLE 9-continued
| Example No. | A | B | C | LCMS Method | LCMS RT (min) | LCMS MS (M + H) | NMB |
|---|---|---|---|---|---|---|---|
| 3-33 | 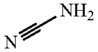 | 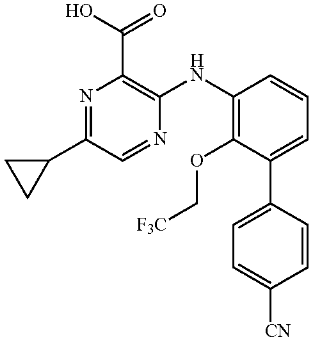 | 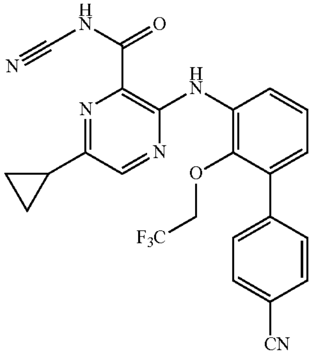 | A | 1.85 | 479 | 1H-NMR (DMSO-D6) δ: 11.49 (br s, 1H), 8.42 (br s, 1H), 5.24 (s, 1H), 7.93 (d, 2H, J = 7.9 Hz), 7.73 (d, 2H, J = 7.9 Hz), 7.28 (t, 1H, J = 7.9 Hz), 7 05 (br s, 1H). 4.15 (q, 2 H, J = 9.0 Hz), 2.25-2.07 (m, 1H), 1.09-0.92 (m, 4H) |
| 3-34 | 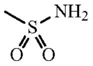 | 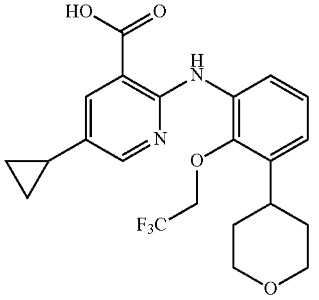 | 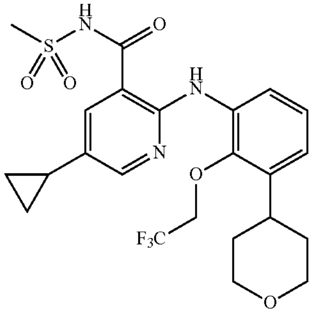 | A | 1 .41 | 514 | 1H-NMR (DMSO-D6) δ: 10.69 (br s, 1H), 8.34 (d, 1H, J = 7.9 Hz), 8.26 (s, 1H), 7.87 (d, 1H, J = 2.0 Hz), 7.14 (t, 1H, J = 7.9 Hz), 8.94 (d, 1H, J = 7.3 Hz), 6.82 (br s, 1H), 4.53 (q, 2H, J = 9.0 Hz). 4.02-3.91 (m, 2H), 3.48-3.38 (m, 2H), 3.20 (s, 3H) 3.24-3.09 (m, 1H), 1 98-1.85 (m, 1H), 1.74-1.60 (m, 4H, 0.98-0.89 (m, 2H). 0.50-0.70 (m, 2H). |
| 3-35 | 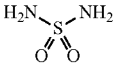 | 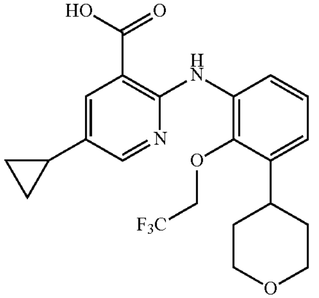 | 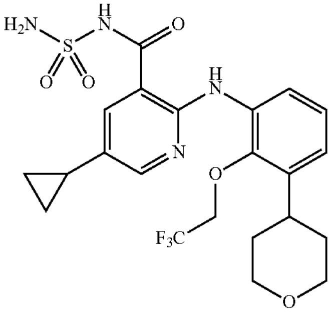 | A | 1.44 | 515 | 1H-NMR (DMSO-D6) δ: 12.04 (br s, 1H), 10.28 (br s, 1H), 8.27 (s, 1H), 8.13 (d, 1H, J = 7.6 Hz), 7.82 (br s, 1H), 7.49 s ,2H), 7.14 (t, 1H, J = 7.9 Hz), 6.97 (d, 1H, J = 7.9 Hz), 4.50 (q, 2H, J = 9.0 Hz), 4.04-3.92 (m, 2H), 3.49-3.39 (m, 2H), 3.25-3.12 (m, 1H), 1.97-1.84 (m, 1H), 1.75-1.59 (m, 4H), 1.00-0.99 (m, 2H) 0.82-072 (m, 2H). |

TABLE 9-continued
| Example No. | A | B | C | LCMS Method | LCMS RT (min) | LCMS MS (M + H) | NMB |
|---|---|---|---|---|---|---|---|
| 3-36 | 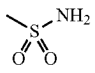 | 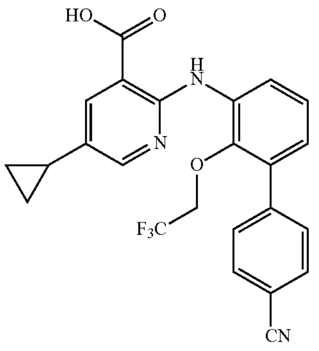 | 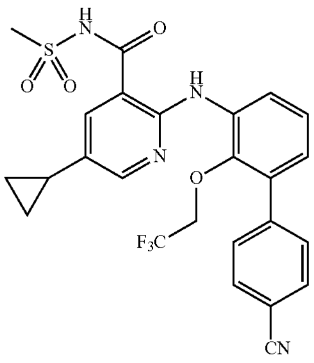 | A | 1.88 | 531 | 1H-NMR (DMSO-D6) δ: 8.62 (d, 1H, J = 8.1 Hz), 8.33 (br s, 1H), 7.94 (d, 2H, J = 7.9 Hz), 7.89 (br s, 1H), 7.74 (d, 2H, J = 7.9 Hz). 7.29 (t, 1H, J = 7.9 Hz), 7.03 (d, 1H, J = 7.9 Hz), 4.14 (q, 2H, J = 8.3 Hz), 3.35 (s, 3H), 2.02-1.86 (m, 1H), 1.02-0.89 (m, 2H), 0.85-0.71 (m, 2H). |
| 3-37 | 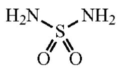 | 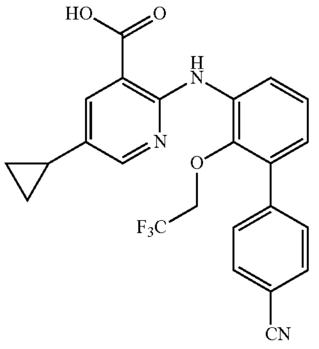 | 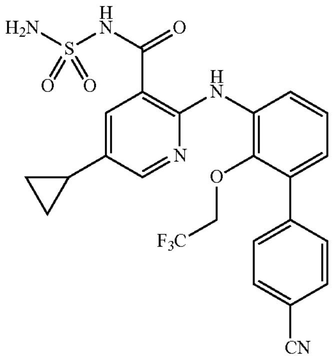 | A | 1.64 | 532 | 1H-NMR (DMSO-D6) δ: 12.04 (br s, 1H), 9.56-9.42 (m, 1H), 8.30 (s, 1H), 7.93 (d, 2H, J = 7.9 Hz). 7.88 (s, 1H), 7,73 (d, 2H, J = 7.9 Hz), 7.50 (br s, 3H), 7.26 (t, 1H, J = 7.9 Hz), 7.04 (d, 1H, J = 7.3 Hz), 4.19 (q, 2H, J = 8.8 Hz), 1.98-1.88 (m. 1H), 1.01-0.99 (m, 2H), 0.84-0.72 (m, 2H). |

TABLE 9-continued
| Example No. | A | B | C | LCMS Method | LCMS RT (min) | LCMS MS (M + H) | NMB |
|---|---|---|---|---|---|---|---|
| 3-38 | 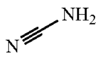 | 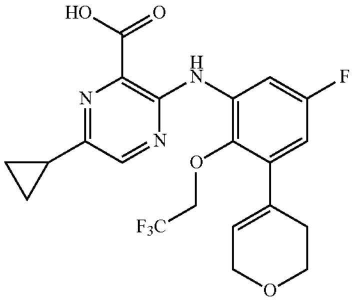 | 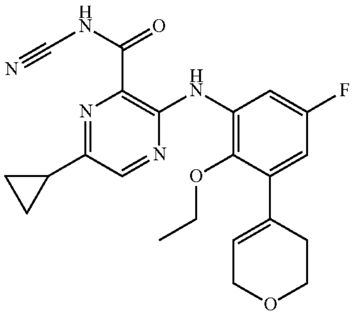 | A | 1.83 | 478 | 1H-NMR (DMSO-D6) δ: 11.08 (br s, 1H), 8.47 (br s, 1H), 8.27 (dd, 1H, J = 11.8, 3.0 Hz), 5.73 (dd, 1H J = 8.9. 3.0 Hz), 0.04 (br s, 1H), 4.42 (q, 2H, J = 9.0 Hz), 4.24-4.16 (m, 2H), 3.82 (t, 2H. J = 5.3 Hz), 2.46-2.36 (m, 2H), 2.22-2.10 (m, 1H), 1.08-0.82 (m, 4H). |
| 3-39 | 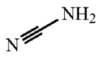 | 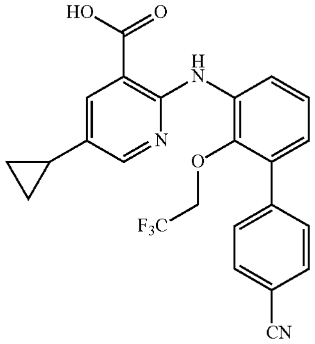 | 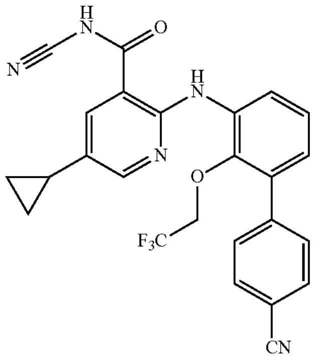 | A | 1.41 | 478 | 1H-NMR (DMSO-D6) δ: 11.98 (br s, 1H), 8.69 (dd, 1H, J = 5.6, 1.3 Hz), 9.09 (d, 1H, J = 2.2 Hz), 5.00 (d, 1H, J = 2.0 Hz), 7.91 (d, 2H, J = 8.3 Hz), 7.71 (d, 2H, J = 8.3 Hz), 7.23 (t, 1H, J = 7.9 Hz), 6.32 (dd, 1H, J = 76.18 Hz), 6.58 (br s 1H), 4.23 (q, 2H, J = 9.0 Hz), 1.96-1.83 (m, 1H), 0.97-0.87 (m, 2H), 0.68-0.58 (m, 2H). |
| 3-40 | 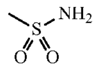 | 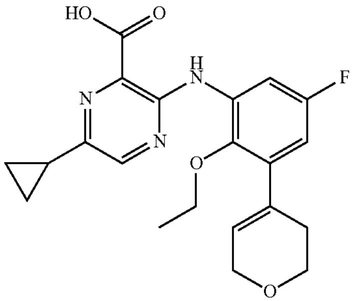 | 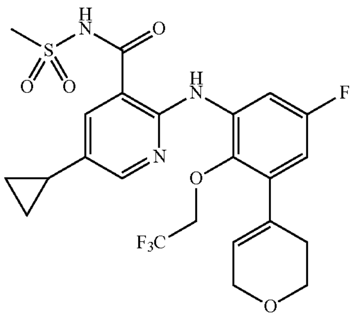 | A | 1.81 | 531 | 1H-NMR (DMSO-D6) δ: 11.68 (br s, 1H), 10.74 (br s, 1H), 8.56 (br s, 1H), 8.25 (dd, 1H, J = 11.2, 3.3 Hz), 6.78 (dd, 1H, J = 10.1., 3.3 Hz). 6.06 (br s, 1H), 4.45 (q, 2H, J = 9.2 Hz), 4.24-4.18 (m, 2H), 3.82 (t, 2H, J = 5.3 Hz), 3.41 (s, 3H), 2.47-2.38 (m, 2H), 2.25-2.13 (m. 1H), 1.19-1.10 (m, 2H), 104-0.82 (m, 2H). |

TABLE 9-continued
| Example No. | A | B | C | LCMS Method | LCMS RT (min) | LCMS MS (M + H) | NMB |
|---|---|---|---|---|---|---|---|
| 3-41 | 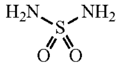 | 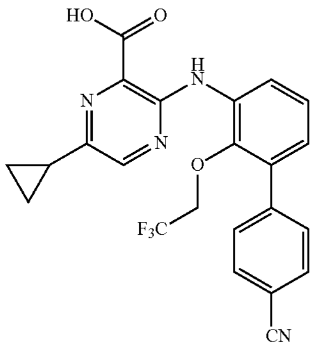 | 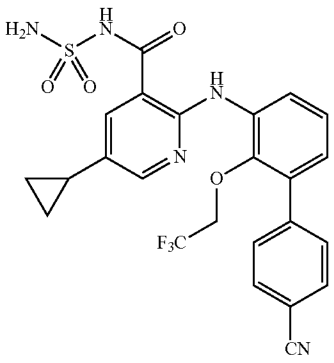 | A | 1.72 | 533 | 1H-NMR (DMSO-D6) δ: 11.32 (br s, 1H), 10.59 (br s, 1H), 8.48 (s, 1H), 3.34 (d, 1H, J = 7.9 Hz), 7.95 (d, 2H, . J = 7.9 Hz) 7.52-7.47 (m, 2H), 7.74 (d, 2H, J = 7.9 Hz), 7.32 (t, 1H, J = 7.9 Hz), 7.13 (d, 1H, J = 7.9 Hz), 4.19 (t, 2H, J = 8.9 Hz), 2.20-2.17 (m, 1H), 1.19-0.90 (m. 4H). |
| 3-42 | 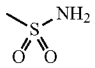 | 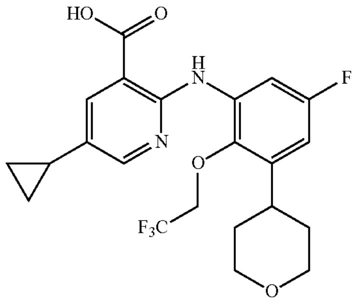 | 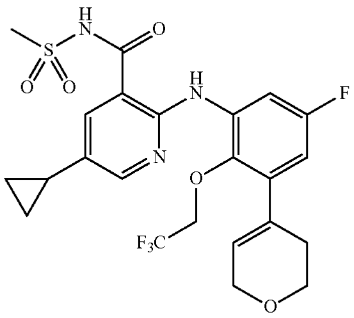 | A | 1.67 | 532 | 1H-NMR (DMSO-D6) δ: 10.74 (br s, 1H), 8.41-8.27 (m, 2H), 7.88 (d, 1H, J = 2.5 Hz), 6.77 (dd, 1H, J = 5.2, 3.3 Hz), 4.55 (q, 2H, J = 8.5 Hz), 3.97 (d, 2H, J = 11.2 Hz), 3.48-3.08 (m, 6H), 2.03-1.84 (m, 1H) 1.74-1.58 (m, 4H), 0.99-0.78 (m, 4H). |

TABLE 9-continued
| Example No. | A | B | C | LCMS Method | LCMS RT (min) | LCMS MS (M + H) | NMB |
|---|---|---|---|---|---|---|---|
| 3-43 | 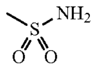 | 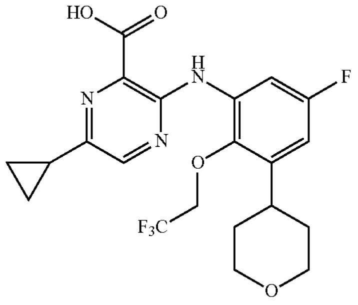 | 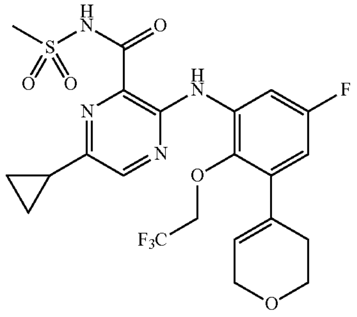 | A | 1.78 | 633 | 1H-NMR (CDCl3) δ: 10.52 (br s, 1H), 8.95 (br s, 1H), 8.41 (s, 1H), 8.09 (dd, 1H. J = 10.8, 3.3 Hz), 6.68 (dd, 1H, J = 9.2, 3.3 Hz), 4.24 (q, 2H, J = 8.1 Hz), 4.15-4.05 (m, 2H), 3.60-3.51 (m, 2H), 3.44 (s, 3H), 3.30-3.13 (m, 1.H), 2.12-2.95 (m, 1H).1.85-1.68 (m, 4H), 1.16-1.07 (m, 2H) 1.01-0.91 (m, 2H). |
| 3-44 | 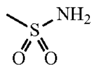 | 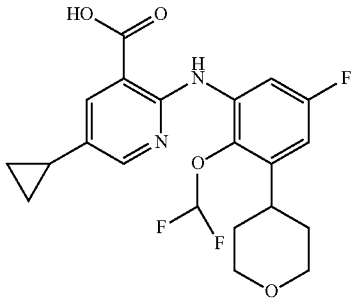 | 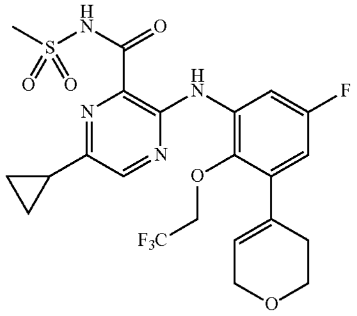 | A | 1.70 | 501 | 1H-NMR (DMSO-D6) δ: 11.69 (br s, 1H), 10.62 (br s, 1H), 8.54 (s, 1H), 8.19 (d, 1H, J = 7.9 Hz), 7.31-6.82 (m, 2H), 3.96 (d, 2H, J = 11.2 Hz), 3.54-3.06 (m, 5H), 2.25-2.13 (m, 1H), 1.83-1.53 (m, 4H) 1.17-0.97 (m, 4H). |
| 3-45 | 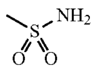 | 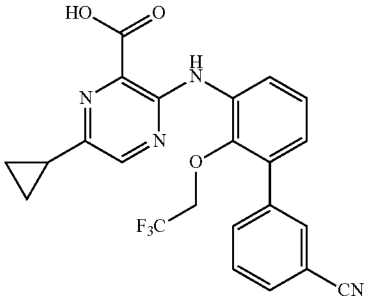 | 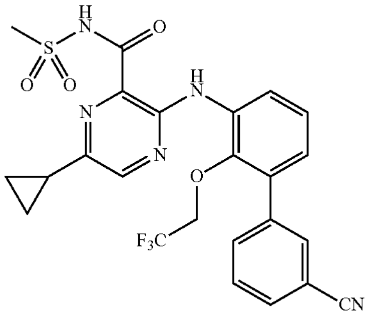 | A | 1.82 | 532 | 1H-NMR (DMSO-D6) δ: 11.52 (br s, 1H), 10.61 (br s, 1H), 8.53 (s 1H), 5.46-5.40 (m, 1H), 8.03 (s, 1H) 7.92-7.85 (m, 2H), 7.69 (t, 1H, J = 7.6 Hz), 7.33 (t, 1H, J = 7.9 Hz), 7.18-7.11 (m, 1H), 4.16 (q, 2H, J = 9.0 Hz), 3.38 (s, 3H), 2.25-2.14 (m, 1H), 1.20-1.12 (m, 2H), 1.03-0.93(m, 2H). |

TABLE 9-continued
| Example No. | A | B | C | LCMS Method | LCMS RT (min) | LCMS MS (M + H) | NMB |
|---|---|---|---|---|---|---|---|
| 3-46 | 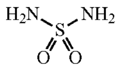 | 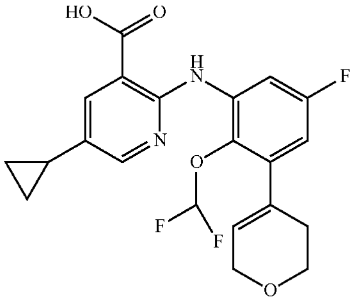 | 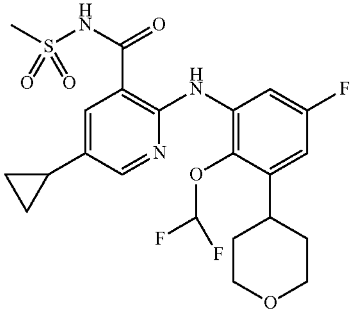 | A | 1.55 | 503 | 1H-NMR (DMSO-D6) δ: 12.09 (br s, 1H), 10.62 (br s, 1H), 5.35 (s, 1H), 8.27 (d, 1H, J = 10.5 Hz), 7.84 (s, 1H), 7.82 (br s, 2H), 7.31-6.82 (m, 2H), 4.12-3.85 (m, 2H), 345-3.33 (m, 2H), 3.23-3.04 (m, 1H), 1.87-1.85 (m, 1H), 1.73-1.51 (m, 4H), 1.02-0.86 (m, 2H), 0.86-0.71 (m, 2H). |
| 3-47 | 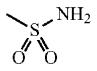 | 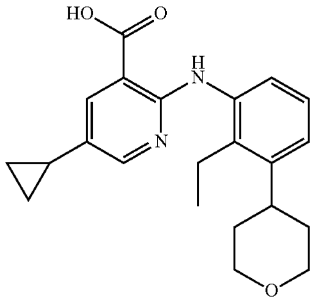 | 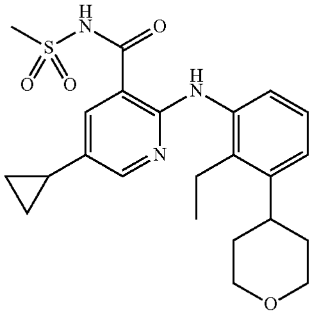 | A | 1.06 | 444 | 1H-NMR (CDCl3) δ: 10.38 (br s, 1H), 7.91 (s, 2H), 7.49-7.34 (m, 1H), 7.21-7.10 (m, 1H), 7.10-6.98 (m, 1H), 4.18-3.58 (m, 2H), 3.49 (t, 2H, J = 11.2 Hz), 3.17 (s, 3H), 3.04-2.53 (m, 1H), 2.78-2.60 (m, 2H), 1.94-1.47 (m, 5H), 1.18-1.01 (m, 3H), 0.97-0.77 (m, 2H), 0.66-0.47 (m, 2H). |
| 3-48 | 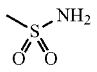 | 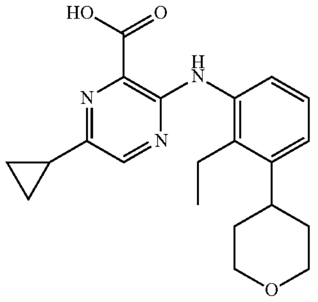 | 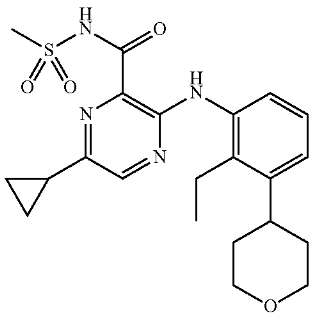 | A | 1.65 | 445 | 1H-NMR (DMSO-D6) δ: 11.47 (br s, 1H), 9.89 (br s, 1H), 8.37 (s, 1H), 7.58 (d, 1H, J = 7.9 Hz), 7.18 (t, 1H, J = 7.9 Hz), 7.10 (d, 1H, J = 7.3 Hz), 4.06-3.83 (m, 2H), 3.50 (t, 2H, J = 10.9 Hz), 3.39 (s, 3H), 3.10-2.94 (m, 1H), 2.78-2.65 (m, 2H) 2.17-2.09 (m, 1H), 1.83-1.53 (m, 4H), 1.21-1.04 (m, 9H), 1.00-0.87 (m, 2H). |

TABLE 9-continued
| Example No. | A | B | C | LCMS Method | LCMS RT (min) | LCMS MS (M + H) | NMB |
|---|---|---|---|---|---|---|---|
| 3-49 | 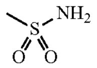 | 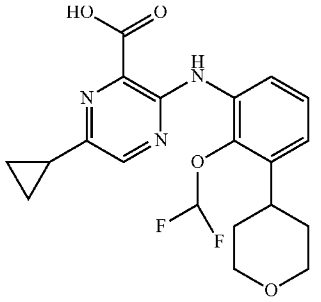 | 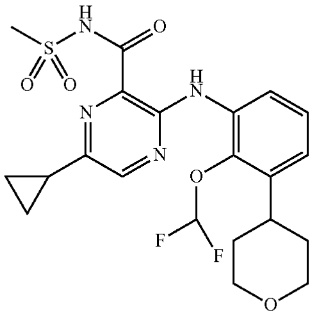 | A | 1.63 | 433 | 1H-NMR (DMSO-D6) δ: 11.61 (br s, 1H), 10.35 (br s, 1H), 8.48 (s, 1H), 8.13 (d,, 1H, J = 8.0 Hz), 7.30 (t, 1H, J = 8.0 Hz) 7.21-6.84 m, 2H), 3.96 (dd, 2H, J = 11.3, 3.0 Hz), 3,47-3.41 (m, 2H), 3.38 (s, 3H), 3.23-3.10 (m, 1H) 2.21-2.13 (m, 1H, 1.78- 1.58 (m, 4H), 1.17-1.07 (m, 2H), 1.01 - 0.91 (m, 2H). |
| 3-50 | 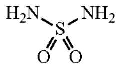 | 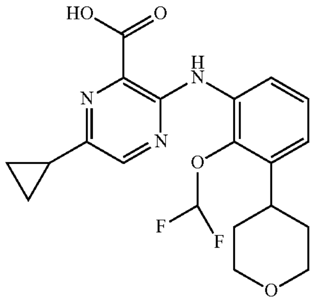 | 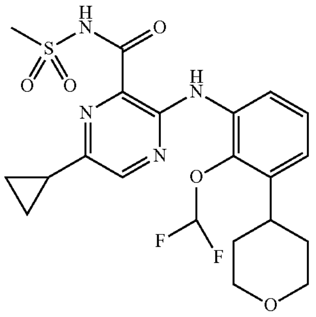 | A | 1.51 | 484 | 1H-NMR (DMSO-D6) δ: 11.24 (br s, 1H), 10.35 (br s, 1H), 8.47 (s, 1H), 8.08 (d, 1H, J = 7.6 Hz), 7.76 (br s, 2H), 7.29 (t, 1H, J = 7.9 Hz), 7.22-6.81 (m, 2H), 4.01-3.92 (m 2H), 3.47-3.41 (m, 2H), 3.20-3.09 (m, 1 H), 2.23-2.13 (m, 1H), 1.79-1.67 (m, 4H), 1.13-1.05 (m, 2H), 1.00-0.92 (m, 2H). |
| 3-51 | 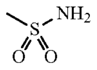 | 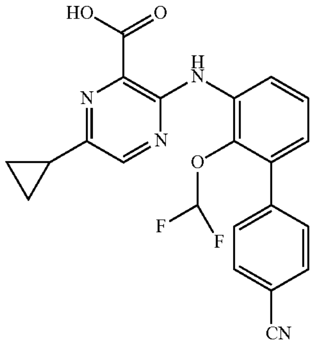 | 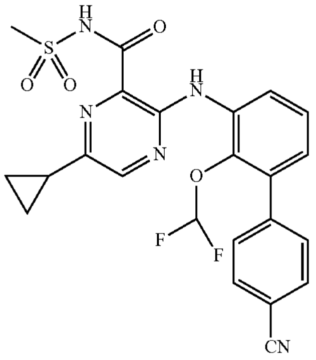 | A | 1.76 | 500 | 1H-NMR (DMSO-D6) δ: 11.65 (br s, 1H), 10.63 (br s, 1H), 8.57-8.42 (m, 2H), 7.95 (d, 2H, J = 8.3 Hz), 7.72 (d, 2H, J = 8.5 Hz), 7.44 (t, 1H, J = 7.9 Hz), 7.17 (d, 1H, J = 7.3 Hz), 6.72 (t, 1H, J = 73.0 Hz), 3.38 (s, 3H), 2.25-2.14 (m, 1H), 1.19-1.08 (m, 2H), 1.03-0.92 (m, 2H). |

TABLE 9-continued
| Example No. | A | B | C | LCMS Method | LCMS RT (min) | LCMS MS (M + H) | NMB |
|---|---|---|---|---|---|---|---|
| 3-52 | 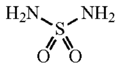 | 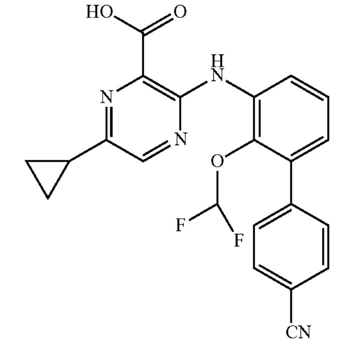 | 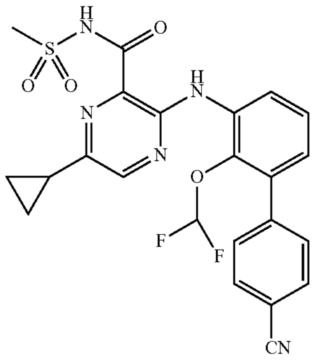 | A | 1.88 | 501 | 1H-NMR (DMSO-D6) δ: 11.31 (br s, 1H), 10.63 (br s, 1H), 8.53 (s, 1H), 8.42 (d, 1H, J = 7.9 Hz), 7.96 (d, 2H, J = 8.6 Hz), 7.78 (br s, 2H), 7.72 (d, 2H, J = 8.6 Hz), 7.45 (t, 1H, J = 7.8 Hz), 7.18 (d, 1H, J = 7.3 Hz), 6.72 (t, 1H, J = 73.0 Hz), 2.25-2.15 (m, 1H), 1.17-1.08 (m, 2H), 1.03-0.93 (m, 2H). |
| 3-53 | 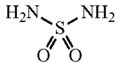 | 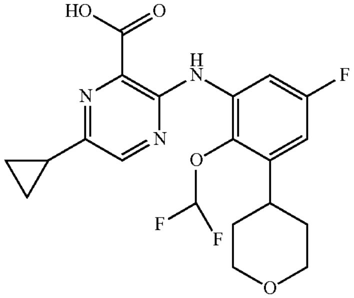 | 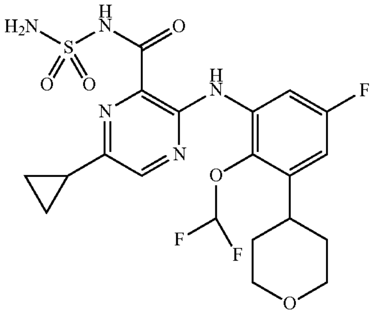 | A | 1.60 | 502 | 1H-NMR (DMSO-D6) δ: 11.36 (br s, 1H), 10.87 (br s, 1H), 8.53 (s, 1H), 8.14 (d, 1H, J = 11.2 Hz), 7.74 (br s, 2H), 7.07 (t, 1H, J = 73.3 Hz), 5.97 (dd, 1H, J = 9.3, 2.7 Hz), 3.97 (d, 3H, J = 10.6 Hz), 3.60-3.27 (m, 2H), 3.23-3.08 (m, 1H), 2.32-2.12 (m, 1H), 1.65-1.53 (m, 4H), 1.20-0.90 (m, 4H). |

TABLE 9-continued
| Example No. | A | B | C | LCMS Method | LCMS RT (min) | LCMS MS (M + H) | NMB |
|---|---|---|---|---|---|---|---|
| 3-54 | 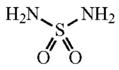 | 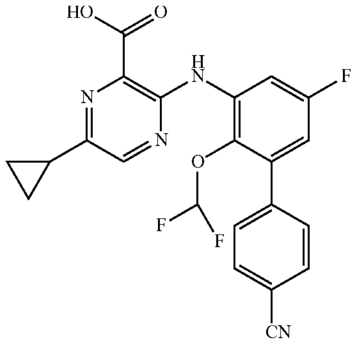 | 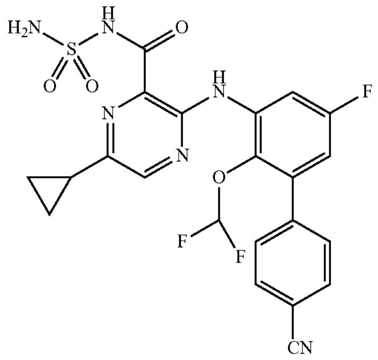 | A | 1.73 | 518 | 1H-NMR (DMSO-D6) δ: 11.41 (br s, 1H), 10.91 (br s, 1H), 8.58 (s, 1H), 8.44 (d, 1H, J = 11.1 Hz), 7.97 (d, 2H, J = 8.0 Hz), 7.85-7.57 (m, 4H), 7.06 (d, 1H, J = 5.8 Hz), 6.74 (t, 1H, J = 72.5 Hz), 2.21 (s, 1H), 1.21-0.90 (m, 4H). |
| 3-55 | 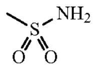 | 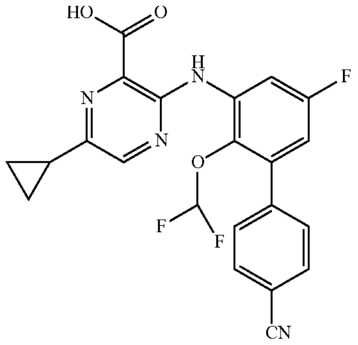 | 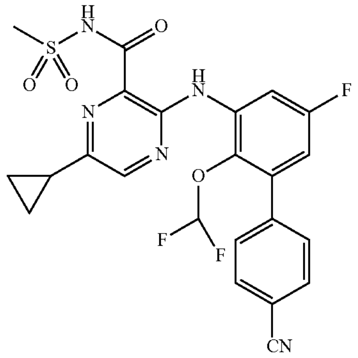 | A | 1.81 | 518 | 1H-NMR (DMSO-D6) δ: 11.74 (br s, 1H), 10.83 (br s, 1H), 8.59 (s, 1H), 8.48 (d, 1H, J = 8.3 Hz), 7.97 (d, 2H, J = 8.5 Hz), 7.74 (d, 2H, J = 8.5 Hz), 7.06 (d, 1H, J = 5.6 Hz), 6.73 (t, 1H, J = 71.4 Hz), 3.36 (s, 3H), 2.32-2.11 (m, 1H), 1.23-0.99 (m, 4H), |

TABLE 9-continued
| Exam-ple No. | A | B | C | LCMS Meth-od | RT (min) | MS (M + H) | NMB |
|---|---|---|---|---|---|---|---|
| 3-56 | 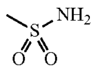 | 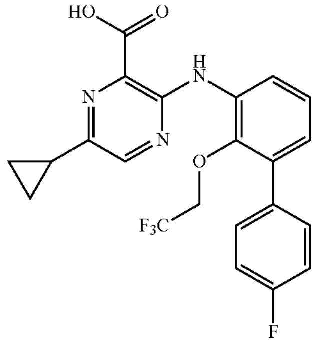 | 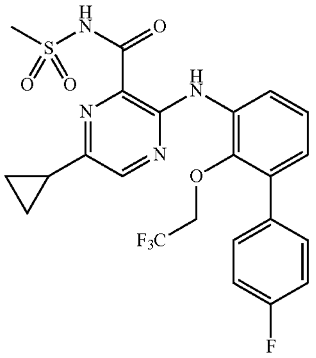 | A | 195 | 5.25 | 1H-NMR (DMSO-D6) δ: 11.58 (br s, 1H), 10.59 (br s, 1H), 8.52 (br s, IH), 8.39 (dd, 1H, J = 8.3, 1.5 Hz), 7.62-7.58 (m, 2H), 7.35-7.25 (m, 3H), 7.06 (d, 3H, J = 7.0 Hz), 4.17-4.03 (m, 2H), 3.35 (s, 3H), 2.25-2.13 (m, 1H), 1.18-1.07 (m, 2H), 1.02-0.93 (m, 2H). |
| 3-57 | 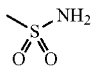 | 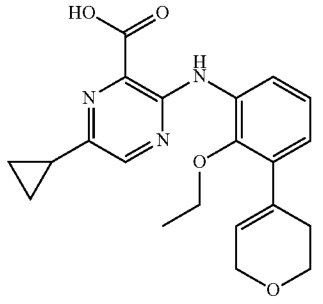 | 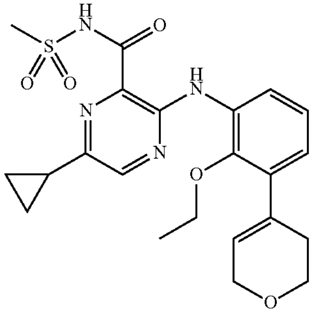 | A | 1.78 | 459 | 1H-NMR (DMSO-D6) δ: 11.55 (br s, 1H), 10.78 (s, 1H), 8.54 (s, 1H), 8.45 (dd, 1H, J = 8.3, 1.5 Hz), 7.09 (t, 1H, J = 7.9 Hz), 6.86 (dd, 2H, J = 7.9 1.5 Hz), 5.99 (br s, 1H), 4.25-4.20 (m, 2H), 3.83-3.80 (m 4H), 3.41 (s, 3H), 2.48-2.42 (m, 2H), 2.22-2.15 (m, 1H), 1.38 (t, 3H, J = 7.0 Hz), 1.15-1.10 (m, 2H), 1.00-0.93 (m, 2H). |
| 3-58 | 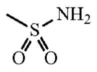 | 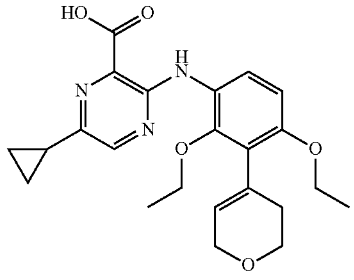 | 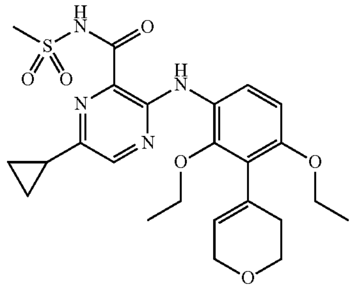 | A | 1.81 | 503 | 1H-NMR (DMSO-D6) δ: 11.47 (br s, 1H), 10.52 (br s, 1H), 3.43 (s, 1H), 3.25 (d, 1H, J = 9.1 Hz), 6.77 (d, 1H, J = 9.3 Hz), 5.70 (br s, 1H), 4.24-4.17 (m, 2H), 3.97 (q, 2H, J = 7.1 Hz), 3.88-3.78 (m, 4H), 3.40 (s, 3H), 2.38-2.29 (m, 2H), 2.23-2.11 (m, 1H), 1.34 (t, 3H, J = 7.1 Hz), 1.28 (t, 3H, J = 7.1 Hz), 1.14-1.06 (m, 2H), 0.98-0.91 (m, 2H). |

TABLE 9-continued
| Example No. | A | B | C | LCMS Method | LCMS RT (min) | LCMS MS (M + H) | NMB |
|---|---|---|---|---|---|---|---|
| 3-59 | 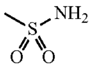 | 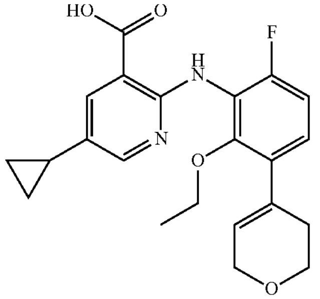 | 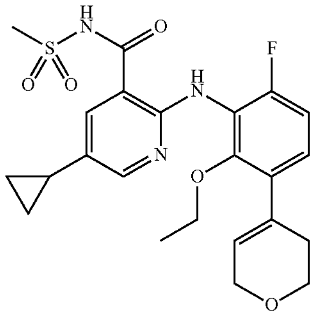 | A | 1.23 | 476 | 1H-NMR (DMSO-D6) δ: 12.25 (br s, 1H), 8.09 (br s, 1H), 7.87 (s, 1H), 7.06-6.96 (m, 2H), 6.81 (br s, 1H), 5.93 (br s, 1H), 4.23-4.18 (m, 2H), 3.79 (t, 2H, J = 5.3 Hz), 3.74 (q, 2H, J = 6.7 Hz), 3.35 (s, 3H), 2.45-2.38 (m, 2H), 1.89-1.82 (m, 1H), 1.14 (t, 3H, J = 6.9 Hz), 0.93-0.83 (m, 2H), 0.76-0.67 (m, 2H). |
| 3-60 | 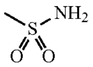 | 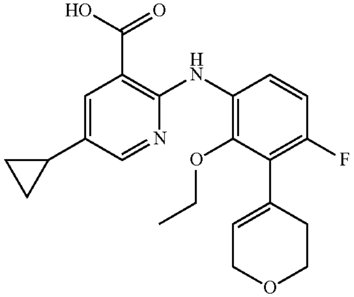 | 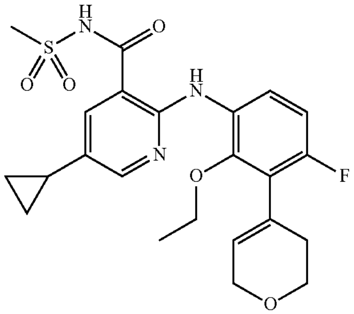 | A | 1.47 | 476 | 1H-NMR (DMSO-D6) δ: 12.24 (br s, 1H), 10.75 (br s, 1H), 8.53 (dd, 1H, J = 9.3, 8.1 Hz), 9.28 (br s, 1H), 7.87 (s, 1H), 6.96 (t, 1H, J = 9.3 Hz), 5.88 9br s, 1H), 4.26-4.19 (m, 2H), 3.89 (q, 2H, J = 7.0 Hz), 3.83 (t, 2H, J = 9.3 Hz), 3.34 (s, 3H), 2.39-2.31 (m, 2H), 1.94-1.87 (m, 1H), 1.37 (t, 3H, J = 7.0 Hz), 0.97-0.89 (m, 2H), 0.79-0.72 (m, 2H). |
| 3-61 | 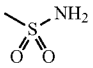 | 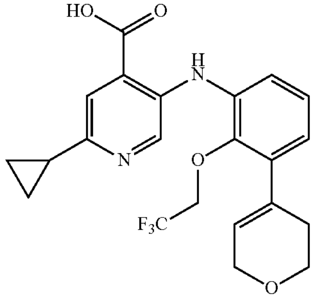 | 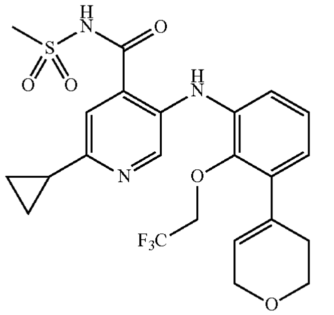 | A | 1.12 | 512 | 1H-NMR (DMSO-D6) δ: 8.39 (br s, 1H), 7.57 (br s, 1H), 7.20 (d, 1H, J = 7.5 Hz), 7.08 (t, 1H, J = 7.8 Hz), 6.86-6.79 (m, 2H), 5.94 (br s, 1H), 4.43 (q, 2H, J = 9.1 Hz), 4.22-4.17 (m, 2H), 3.80 (t, 2H, J = 5.3 Hz), 3.35 (s, 3H), 2.44-2.37 (m, 2H), 2.12-2.03 (m, 1H), 0.97-0.90 (m, 4H). |

TABLE 9-continued
| Example No. | A | B | C | LCMS Method | LCMS RT (min) | LCMS MS (M + H) | NMB |
|---|---|---|---|---|---|---|---|
| 3-62 | 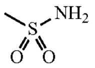 | 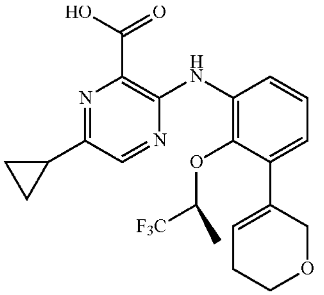 | 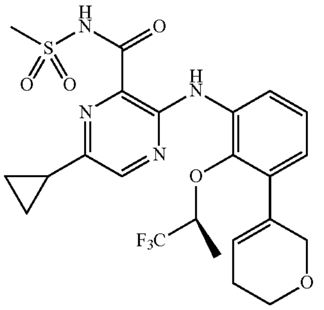 | A | 1.81 | 527 | 1H-NMR (DMSO-D6) δ: 11.58 (br s, 1H), 10.44 (br s, 1H), 8.50 (br s, 1H), 8.27 (d, 1H, J = 7.9 Hz), 7.16 (t, 1H, J = 7.9 Hz), 6.80 (d, 1H, J = 7.8 Hz), 6.03 (br s, 1H), 4.75-4.65 1H), 4.34 (d, 1H, J = 15.8 Hz), 4.24 (d, 1H), J = 15.6 Hz), 3.77 (t, 2H, J = 5.5 Hz), 3.39 (s, 3H), 2.25-2.21 (m, 2H), 2.21-2.14 (m, 1H), 1.30 (d, 3H, J = 5.8 Hz), 1.00-0.92 (m, 2H), 0.89-0.82 (m, 2H). |
| 3-63 | 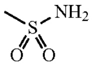 | 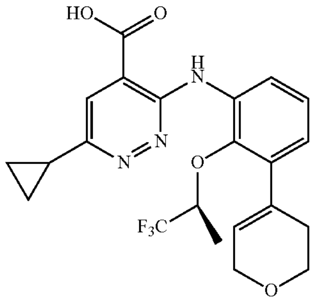 | 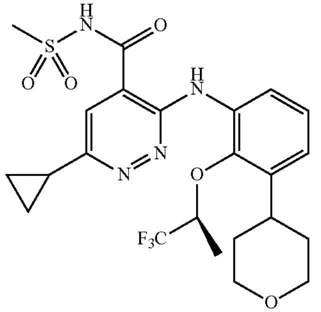 | A | 1.13 | 529 | 1H-NMR (DMSO-D6) δ: 11.07 (s, 1H), 8.07 (d, 1H, J = 7.0 Hz), 7.72 (s, 1H), 7.11 (dd, 2H, J = 7.0, 6.5 Hz), 6.97 (d, 1H, J = 6.5 Hz), 4.75-4.66 (m, 1H), 4.03-3.91 (m, 2H), 3.48-3.16 (m, 3H), 2.91 (s, 3H), 2.22-2.15 (m, 1H), 1.69-1.54 (m, 4H), 1.36 (d, 3H, J = 8.5 Hz), 0.98-0.90 (m, 4H). |
| 3-64 | 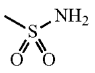 | 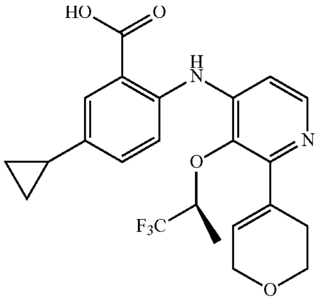 | 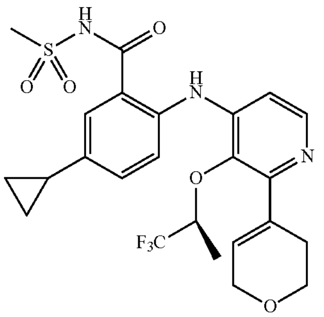 | A | 1.12 | 526 | 1H-NMR (CDCl3) δ: 10.24 (br s, 1H), 8.02 (d, 1H, J = 5.3 Hz), 7.77 (br s, 1H), 7.23 (d, 1H, J = 8.3 Hz), 7.09-7.01 (m, 2H), 8.28 (br s, 1H), 4.79 (br s, 1H), 4.53-4.42 (m, 1H), 4.26-4.18 (m, 2H), 3.90-3.82 (m, 2H), 3.09 (s, 3H), 2.64-2.42 (m, 2H), 1.84-1.73 (m, 1H), 1.37 (d, 3H, J = 6.5 Hz), 0.92-0.80 (m, 2H), 0.64-0.56 (m, 2H). |

TABLE 9-continued
| Example No. | A | B | C | LCMS Method | LCMS RT (min) | LCMS MS (M + H) | NMB |
|---|---|---|---|---|---|---|---|
| 3-65 | 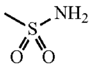 | 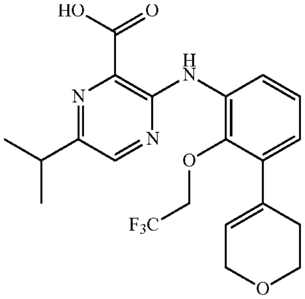 | 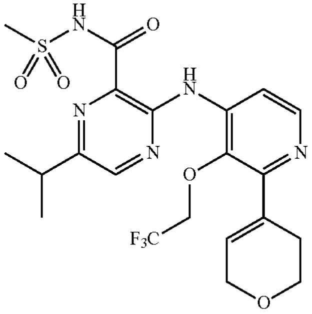 | A | 1.32 | 515 | 1H-NMR (CDCl3) δ: 10.51 (br s, 1H), 10.13 (br s, 1H), 8.37 (s, 1H), 8.26 (dd, 1H, J = 8.3, 1.5 Hz), 7.18 (t, 1H, J = 7.9 Hz), 6.93 (dd, 1H, J = 7.8, 1.9 Hz), 6.00 (s, 1H), 4.33 (q, 2H, J = 2.7 Hz), 4.23 (q, 2H, J = 8.4 Hz), 3.93 (t, 2H, J = 5.4 Hz), 3.45 (s, 3H), 8.11-8.04 (m, 1H), 2.55-2.49 (m, 2H). 1.33 (d, 9H, J = 7.0 Hz). |
| 3-66 | 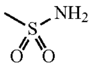 | 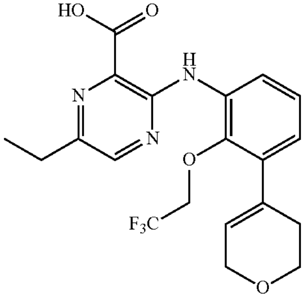 | 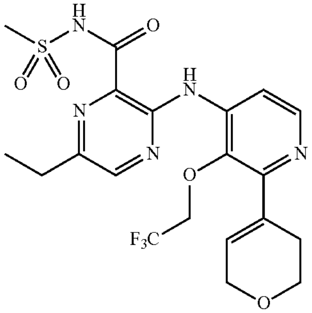 | A | 1.72 | 501 | 1H-NMR (DMSO-D6) δ: 11.87 (br s, 1H), 10.55 (br s, 1H), 3.47 (s, 1H), 8.31 (dd, 1H, J = 8.3, 1.5 Hz), 7.18 (t, 1H, J = 3.0 Hz), 6.94 (dd, 1H, J = 7.3, 1.5 Hz), 5.99 (s, 1H), 4.45 (s, 2H, J = 6.0 Hz), 4.21 (d, 2H, J = 2.5 Hz), 3.83 (t, 2H, J = 5.4 Hz), 3.39 (s, 3H), 2.77 (q, 2H, J = 7.6 Hz), 2.46-2.39 (m, 2H), 1.23 (t, 3H, J = 7.6 Hz). |
| 3-67 | 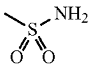 | 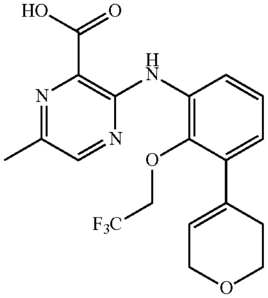 | 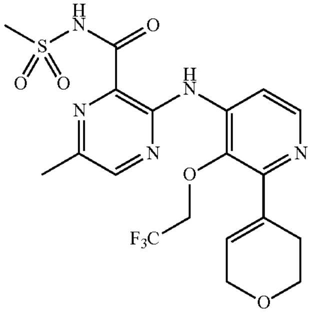 | A | 1.60 | 487 | 1H-NMR (DMSO-D6) δ: 11.67 (br s, 1H), 10.52 (br s, 1H), 5.43 (s, 1H), 8.32-8.28 (m, 1H), 7.18 (t, 1H, J = 5.0 Hz), 6.94 (dd, 1H, J = 7.8, 1.5 Hz), 5.99 (s, 1H), 4.45 (s, 2H, J = 9.0 Hz), 4.21 (d, 2H, J = 2.5 Hz), 3.83 (t, 2H, J = 5.3 Hz), 3.37 (s, 3H), 2.47 (s, 3H), 2.45-2.33 (m, 2H). |

TEST EXAMPLES

Test Example 1

Enzyme Reaction Inhibition Test

The DHODH enzyme assay was carried out with reference to "Benjamin Bader, Wolfgang Knecht, Markus Fries, and Monika Loffler, Expression, Purification, and Characterization of Histidine-Tagged Rat and Human Flavoenzyme Dihydroorotate Dehydrogenase, Protein Expression and Purification, 1998, 13, 414-422."

The DHODH activity was evaluated using an enzyme assay system that is coupled with an assay in which a blue coloring agent 2,6-dichlorophenolindophenol (DCIP, available from MP Biomedicals, LLC, MP150118) is quenched. Purified recombinant human DHODH (DHODH, 31-395aa, Human, His tag, *E. coli*, ATGP1615) was purchased from ATGen Co. Ltd. The enzyme assay was carried out in a 384-well plate using a buffer solution containing 100 mmol/L Hepes (available from Dojindo Laboratories, 342-01375), 400 mmol/L NaCl (available from FUJIFILM Wako Pure Chemical Corporation, 191-01665), 10% Glycerol (available from FUJIFILM Wako Pure Chemical Corporation, 075-00616), 0.05% Triton X-100 (available from Sigma-Aldrich Co., LLC, T8787-100ML), 0.2 mmol/L Ubiquinone-10 (available from FUJIFILM Wako Pure Chemical Corporation, 216-00761), 0.1 mmol/L DHO (L-dihydroorotic acid, available from Sigma-Aldrich Co., LLC, D7128), 0.5% DMSO (dimethylsulfoxide, available from FUJIFILM Wako Pure Chemical Corporation, 047-29353), 0.175 μg/mL DHODH, and 0.12 mmol/L DCIP and having a pH adjusted to 8.0 by adding 5 mol/L potassium hydroxide (available from FUJIFILM Wako Pure Chemical Corporation, 168-21815). A test compound with a predetermined concentration was added using Biomek NX (available from Beckman Coulter Inc.), and the enzyme reaction was started by adding the substrate. The enzyme activity was assessed by measuring the decrease in DCIP absorbance (600 nm) for 50 minutes using an EnVision plate-reading spectrophotometer (available from PerkinElmer, Inc.).

The enzyme reaction inhibition rate at each test compound concentration was determined, and the 50% enzyme reaction inhibition concentration [IC50 (nmol/L)] was calculated using XLfit.

Enzyme reaction inhibition rate (%)=(amount of luminescence in test compound-added well)/(amount of luminescence in DMSO-added well)×100

The results are shown in Table 10. The abbreviations in the table have the following meanings.

A: IC50 value<10 nmol/L

B: 10 nmol/L≤IC50 value<100 nmol/L

C: 100 nmol/L≤IC50 value

As shown in Table 10, each test compound showed an excellent enzyme reaction inhibitory effect.

Test Example 2

Cell Growth Test

The cell growth test was carried out using the human myeloid leukemia cell line HL60 (available from ATCC, CRL-240). As a culture medium of HL60 cells, RPMI 1640 (available from FUJIFILM Wako Pure Chemical Corporation, 189-02025) supplemented with 10% fetal bovine serum (available from Thermo Fisher Scientific, Inc., 10437-028), and 1% penicillin-streptomycin (10,000 U/mL, available from Thermo Fisher Scientific, Inc., 15140-122) was used. HL60 cells were seeded on a 384-well plate (available from Corning Inc., 4588) at a cell density of $1\times10^3$ cells/20 μL/well. After culturing overnight, 5 μL of the test compound having a predetermined concentration was added, and 3 days later, 25 μL of CellTiter-Glo (registered trademark) Luminescent Cell Viability Assay (available from Promega Corporation, G7573) was added, and then the amount of luminescence was measured using an EnVision plate reader (available from PerkinElmer, Inc.). Since the amount of luminescence is proportional to the intracellular concentration of adenosine triphosphate (ATP), the amount of luminescence was used as an indicator of the number of viable cells. The growth inhibitory concentration for each test compound concentration was calculated by the following expression.

The growth inhibition rate at each test compound concentration was determined, and the 50% growth inhibitory concentration [GI50 (nmol/L)] was calculated using XLfit.

Growth inhibition rate (%)=(amount of luminescence in test compound-added well)/(amount of luminescence in DMSO-added well)×100

The results are shown in Table 10. The abbreviations in the table have the following meanings.

A: GI50 value<100 nmol/L

B: 100 nmol/L≤GI50 value<1,000 nmol/L

C: 1,000 nmol/L≤GI50 value

As shown in Table 10, each test compound showed an excellent cell growth inhibition rate.

TABLE 10

| Example No. | Enzyme reaction inhibitory effect | Cell growth inhibitory effect |
|---|---|---|
| 1-1 | B | A |
| 1-2 | A | A |
| 1-3 | B | B |
| 1-4 | B | B |
| 1-5 | A | A |
| 1-6 | A | A |
| 1-7 | A | B |
| 1-8 | B | B |
| 1-9 | B | B |
| 1-10 | B | B |
| 1-11 | C | C |
| 1-12 | B | B |
| 1-13 | C | C |
| 1-14 | C | C |
| 1-15 | C | C |
| 1-16 | B | B |
| 1-17 | C | C |
| 1-18 | A | A |
| 2-1 | A | B |
| 2-2 | A | A |
| 2-3 | A | A |
| 2-4 | A | A |
| 2-5 | A | A |
| 2-6 | A | A |
| 2-7 | A | A |
| 2-8 | A | A |
| 2-9 | A | A |
| 2-10 | A | A |
| 2-11 | A | B |
| 2-12 | B | B |
| 2-13 | A | A |
| 2-14 | A | B |
| 2-15 | A | A |
| 2-16 | A | B |
| 2-17 | A | C |
| 3-1 | A | A |
| 3-2 | A | C |
| 3-3 | A | A |

TABLE 10-continued

| Example No. | Enzyme reaction inhibitory effect | Cell growth inhibitory effect |
|---|---|---|
| 3-4 | B | A |
| 3-5 | A | A |
| 3-6 | A | A |
| 3-7 | A | B |
| 3-8 | A | A |
| 3-9 | A | A |
| 3-10 | A | A |
| 3-11 | C | C |
| 3-12 | B | B |
| 3-13 | B | B |
| 3-14 | A | A |
| 3-15 | B | B |
| 3-16 | A | A |
| 3-17 | B | C |
| 3-18 | B | C |
| 3-19 | B | B |
| 3-20 | B | B |
| 3-21 | B | C |
| 3-22 | A | A |
| 3-23 | A | A |
| 3-24 | A | A |
| 3-25 | B | B |
| 3-26 | A | A |
| 3-27 | A | A |
| 3-28 | A | A |
| 3-29 | A | A |
| 3-30 | A | A |
| 3-31 | A | A |
| 3-32 | A | A |
| 3-33 | A | A |
| 3-34 | A | A |
| 3-35 | A | A |
| 3-36 | A | A |
| 3-37 | A | A |
| 3-38 | A | A |
| 3-39 | A | A |
| 3-40 | A | A |
| 3-41 | A | A |
| 3-42 | A | A |
| 3-43 | A | A |
| 3-44 | A | A |
| 3-45 | A | A |
| 3-46 | A | A |
| 3-47 | A | B |
| 3-48 | B | B |
| 3-49 | A | A |
| 3-50 | A | A |
| 3-51 | A | B |
| 3-52 | B | B |
| 3-53 | A | A |
| 3-54 | B | B |
| 3-55 | B | B |
| 3-56 | A | A |
| 3-57 | A | A |
| 3-58 | A | A |
| 3-59 | B | C |
| 3-60 | A | A |
| 3-61 | A | B |
| 3-62 | B | B |
| 3-63 | B | C |
| 3-64 | B | B |
| 3-65 | A | B |
| 3-66 | A | B |
| 3-67 | B | B |

Test Example 3

In Vivo Drug Efficacy Test in Cancer-Bearing Mice (Drug Efficacy Test in Cancer-Bearing Mouse Model with Subcutaneous Transplantation of HL60)

The human acute myeloid leukemia cell line HL60 (available from JCRB) was suspended in a mixture of RPMI-1640 culture medium and Matrigel (available from Corning Inc.), and then subcutaneously transplanted into 6-week-old female NOD/scid mice (available from CLEA Japan, Inc.). The test compound was dispersed in a solvent (0.5% aqueous methylcellulose solution), and from the time when tumor engraftment was visually confirmed, the test compound was orally administered to mice at a dose of 2.5 to 10 mg/kg once a day for 10 to 12 days. A solvent administration group to which a 0.5% aqueous methylcellulose solution was administered was provided as a negative control. The tumor diameter was measured over time and the tumor volume was calculated. The tumor volume was calculated by measuring the major axis and the minor axis of the tumor and using the following expression.

$$\text{Tumor volume } (mm^3)=[\text{major axis (mm)}\times\text{minor axis (mm)}\times\text{minor axis (mm)}]/2$$

T/C (%) was calculated from the average tumor volume of each group by the following expression, and the drug efficacy was evaluated.

$$T/C\ (\%)=(\text{average tumor volume of drug-administered group})/(\text{average tumor volume of solvent-administered group})\times 100\%$$

As a result of evaluating the drug efficacy, each test compound (for example, the compounds described in Example 1-2, Example 3-30, Example 3-41, Example 3-44, and Example 3-49) showed an excellent tumor growth inhibition rate.

The compound or salt thereof according to an aspect of the present invention has an excellent DHODH inhibitory effect and is useful as a DHODH inhibitor.

In addition, the compound or salt thereof according to the aspect of the present invention has an excellent anti-tumor activity and is useful as a pharmaceutical composition such as an anti-tumor agent. The compound or salt thereof according to the aspect of the present invention is useful for the treatment such as prevention or treatment of blood cancers.

In addition, the compound selected from Compound group X or a salt thereof is useful as an intermediate for producing the compound or salt thereof according to the aspect of the present invention.

What is claimed is:

1. A compound represented by General Formula (1) or a salt thereof:

(1)

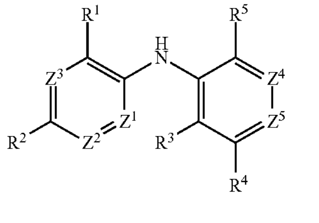

in the formula, $Z^1$ is a nitrogen atom;

$Z^2$ is C;

$Z^3$ represents a nitrogen atom or CH;

$Z^4$ represents a general formula of $CR^6$;

$Z^5$ represents a general formula of $CR^7$;

$R^1$ represents a general formula of $CONHR^8$, a general formula of $CH_2NHR^8$, $CH_2OH$, $CH(OH)CH_3$, $C(O)CH_3$, CHO, Formula (1-1), Formula (1-2), or Formula (1-3);

(1-1)

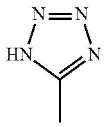

(1-2)

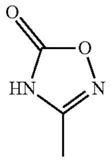

(1-3)

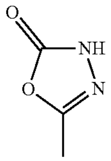

$R^2$ represents a $C_{1-6}$ alkyl group which may be substituted or a $C_{3-8}$ cycloalkyl group which may be substituted;

$R^3$, $R^5$, $R^6$, and $R^7$ are the same as or different from each other and represent a hydrogen atom, a halogen atom, a hydroxyl group which may be protected, an amino group which may be protected, a $C_{1-6}$ alkyl group which may be substituted, a $C_{2-6}$ alkenyl group which may be substituted, a $C_{2-6}$ alkynyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a $C_{1-6}$ alkoxy $C_{1-6}$ alkyl group which may be substituted;

$R^4$ represents an aryl group which may be substituted or a heterocyclic group which may be substituted;

$R^8$ represents a hydrogen atom, a hydroxyl group which may be protected, an amino group which may be protected, a $C_{1-6}$ alkyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, a di($C_{1-6}$ alkyl)amino group which may be substituted, or a general formula of $SO_2R^9$; and $R^9$ represents a hydroxyl group which may be protected, an amino group which may be protected, a $C_{1-6}$ alkyl group which may be substituted, a $C_{3-8}$ cycloalkyl group which may be substituted, a $C_{1-6}$ alkoxy group which may be substituted, a $C_{3-8}$ cycloalkoxy group which may be substituted, a $C_{1-6}$ alkylamino group which may be substituted, or a di($C_{1-6}$ alkyl)amino group which may be substituted.

2. The compound or salt thereof according to claim 1, wherein $R^2$ is a $C_{1-6}$ alkyl group or a $C_{3-8}$ cycloalkyl group.

3. The compound or salt thereof according to claim 1, wherein $R^1$ is a general formula of $CONHR^8$, Formula (1-1), Formula (1-2), or Formula (1-3), (1-1)

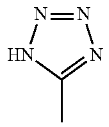

(1-2)

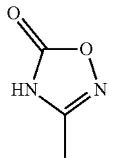

(1-3)

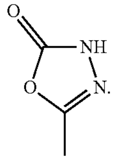

4. The compound or salt thereof according to claim 1, wherein $R^3$, $R^5$, $R^6$, and $R^7$ are the same as or different from each other and are a hydrogen atom, a halogen atom, a hydroxyl group which may be protected, an amino group which may be protected, a $C_{1-6}$ alkyl group which may be substituted with one or more substituents selected from Substituent Group A, a $C_{2-6}$ alkenyl group which may be substituted with one or more substituents selected from Substituent Group A, a $C_{2-6}$ alkynyl group which may be substituted with one or more substituents selected from Substituent Group A, a $C_{3-8}$ cycloalkyl group which may be substituted with one or more substituents selected from Substituent Group A, a $C_{1-6}$ alkoxy group which may be substituted with one or more substituents selected from Substituent Group A, a $C_{3-8}$ cycloalkoxy group which may be substituted with one or more substituents selected from Substituent Group A, a $C_{1-6}$ alkylamino group which may be substituted with one or more substituents selected from Substituent Group A, a di($C_{1-6}$ alkyl) amino group which may be substituted with one or more substituents selected from Substituent Group A, or a $C_{1-6}$ alkoxy $C_{1-6}$ alkyl group which may be substituted with one or more substituents selected from Substituent Group A, Substituent Group A:

a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent Group B; and a heterocyclic group which may be substituted with one or more substituents selected from Substituent Group B, Substituent Group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

5. The compound or salt thereof according to claim 1, wherein $R^3$ is a halogen atom, a hydroxyl group which may be protected, an amino group which may be protected, a $C_{1-6}$ alkyl group which may be substituted with one or more substituents selected from Substituent Group A, a $C_{2-6}$ alkenyl group which may be substituted with one or more substituents selected from Substituent Group A, a $C_{2-6}$ alkynyl group which may be substituted with one or more substituents selected from Substituent Group A, a $C_{3-8}$ cycloalkyl group which may be substituted with one or more substituents selected from Substituent Group A, a $C_{1-6}$ alkoxy group which may be substituted with one or more substituents selected from Substituent Group A, a $C_{3-8}$ cycloalkoxy group which may be substituted with one or more substituents selected from Substituent Group A, a $C_{1-6}$ alkylamino group which may be substituted with one or more substituents selected from Substituent Group A, a di($C_{1-6}$ alkyl)amino group which may be substituted with one or more substituents selected from Substituent Group A, or a $C_{1-6}$ alkoxy $C_{1-6}$ alkyl group which may be substituted with one or more substituents selected from Substituent Group A, Substituent Group A:

a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent Group B; and a heterocyclic group which may be substituted with one or more substituents selected from Substituent Group B, Substituent Group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

6. The compound or salt thereof according to claim 1, in which $R^5$, $R^6$, and $R^7$ are the same as or different from each other and are a hydrogen atom, a halogen atom, a $C_{1-6}$ alkyl group which may be substituted with one or more substituents selected from Substituent Group A, or a $C_{1-6}$ alkoxy group which may be substituted with one or more substituents selected from Substituent Group A, Substituent Group A:

a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent Group B; and a heterocyclic group which may be substituted with one or more substituents selected from Substituent Group B, Substituent Group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

7. The compound or salt thereof according to claim 1, wherein $R^4$ is an aryl group which may be substituted with one or more substituents selected from Substituent Group A, a monocyclic nitrogen-containing heterocyclic group which may be substituted with one or more substituents selected from Substituent Group A, a monocyclic oxygen-containing heterocyclic group which may be substituted with one or more substituents selected from Substituent Group A, a bicyclic nitrogen-containing heterocyclic group which may be substituted with one or more substituents selected from Substituent Group A, or a bicyclic oxygen-containing heterocyclic group which may be substituted with one or more substituents selected from Substituent Group A, Substituent Group A:

a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent Group B; and a heterocyclic group which may be substituted with one or more substituents selected from Substituent Group B, Substituent Group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

8. The compound or salt thereof according to claim 7, wherein $R^4$ is a phenyl group which may be substituted with one or more substituents selected from Substituent Group A, a pyridyl group which may be substituted with one or more substituents selected from Substituent Group A, a tetrahydropyranyl group which may be substituted with one or more substituents selected from Substituent Group A, or a dihydropyranyl group which may be substituted with one or more substituents selected from Substituent Group A, Substituent Group A:

a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent Group B; and a heterocyclic group which may be substituted with one or more substituents selected from Substituent Group B, Substituent Group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

9. The compound or salt thereof according to claim 1, wherein $R^8$ is a hydrogen atom, a hydroxyl group which may be protected, an amino group which may be protected, a $C_{1-6}$ alkoxy group which may be substituted with one or more substituents selected from Substituent Group A, a $C_{3-8}$ cycloalkoxy group which may be substituted with one or more substituents selected from Substituent Group A, a $C_{1-6}$ alkylamino group which may be substituted with one or more substituents selected from Substituent Group A, a di($C_{1-6}$ alkyl)amino group which may be substituted with one or more substituents selected from Substituent Group A, or a general formula of $SO_2R^9$, Substituent Group A:

a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent Group B; and a heterocyclic group which may be substituted with one or more substituents selected from Substituent Group B, Substituent Group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

10. The compound or salt thereof according to claim 1, wherein $R^9$ is an amino group which may be protected, a $C_{1-6}$ alkyl group which may be substituted with one or more substituents selected from Substituent Group A, a $C_{3-8}$ cycloalkyl group which may be substituted with one or more substituents selected from Substituent Group A, a $C_{1-6}$ alkoxy group which may be substituted with one or more substituents selected from Substituent Group A, a $C_{3-8}$ cycloalkoxy group which may be substituted with one or more substituents selected from Substituent Group A, a $C_{1-6}$ alkylamino group which may be substituted with one or more substituents selected from Substituent Group A, or a di($C_{1-6}$ alkyl) amino group which may be substituted with one or more substituents selected from Substituent group A, Substituent Group A:

a halogen atom; a cyano group; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; an aryl group which may be substituted with one or more substituents selected from Substituent Group B; and a heterocyclic group which may be substituted with one or more substituents selected from Substituent Group B, Substituent Group B:

a halogen atom; a hydroxyl group which may be protected; an amino group which may be protected; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{3-8}$ cycloalkoxy group; a $C_{1-6}$ alkylamino group; a di($C_{1-6}$ alkyl)amino group; and a $C_{1-6}$ alkoxy $C_{1-6}$ alkyl group.

11. A pharmaceutical composition comprising:
the compound or salt thereof according to claim 1.

12. An anti-tumor agent comprising:
the compound or salt thereof according to claim 1.

13. A dihydroorotate dehydrogenase inhibitor comprising:
the compound or salt thereof according to claim 1.

14. A compound selected from Compound Group X or a salt thereof:

Compound Group X:

6-cyclopropyl-3-((3-(2,6-dimethylpyridin-3-yl)-2-(2,2,2-trifluoroethoxy)phenyl)amino)pyrazine-2-carboxylic acid, 3-((4'-cyano-2'-methyl-2-(2,2,2-trifluoroethoxy)-[1,1'-biphenyl]-3-yl)amino)-6-cyclopropylpyrazine-2-carboxylic acid, (S)-5-cyclopropyl-2-((2-(3,6-dihydro-2H-pyran-4-yl)-3-((1,1,1-trifluoropropan-2-yl)oxy)pyridin-4-yl)amino)benzoic acid, 5-cyclopropyl-2-((5-(3,6-dihydro-2H-pyran-4-yl)-4-(2,2,2-trifluoroethoxy)pyridin-3-yl)amino)benzoic acid, 5-cyclopropyl-2-((3-(tetrahydro-2H-pyran-4-yl)-2-(2,2,2-trifluoroethoxy)phenyl)amino)nicotinic acid, 5-cyclopropyl-2-((2-(difluoromethoxy)-5-fluoro-3-(tetrahydro-2H-pyran-4-yl)phenyl)amino)nicotinic acid, 3-((4'-cyano-2-(2,2,2-trifluoroethoxy)-[1,1'-biphenyl]-3-yl)amino)-6-cyclopropylpyrazine-2-carboxylic acid, 5-cyclopropyl-2-((3-(3,6-dihydro-2H-pyran-4-yl)-2-(2,2,2-trifluoroethoxy)phenyl)amino)nicotinic acid, (S)-5-cyclopropyl-2-((5-(3,6-dihydro-2H-pyran-4-yl)-4-((1,1,1-trifluoropropan-2-yl)oxy)pyridin-3-yl)amino)benzoic acid, 2-((4'-cyano-2-(2,2,2-trifluoroethoxy)-[1,1'-biphenyl]-3-yl)amino)-5-cyclopropylnicotinic acid, 5-cyclopropyl-2-((5-fluoro-3-(tetrahydro-2H-pyran-4-yl)-2-(2,2,2-trifluoroethoxy)phenyl)amino)nicotinic acid, 3-((3'-cyano-2-(2,2,2-trifluoroethoxy)-[1,1'-biphenyl]-3-yl)amino)-6-cyclopropylpyrazine-2-carboxylic acid, 5-cyclopropyl-2-((2-ethyl-3-(tetrahydro-2H-pyran-4-yl)phenyl)amino)nicotinic acid, 3-((4'-cyano-2-(difluoromethoxy)-[1,1'-biphenyl]-3-yl)amino)-6-cyclopropylpyrazine-2-carboxylic acid, 3-((4'-cyano-2-(difluoromethoxy)-5-fluoro-[1,1'-biphenyl]-3-yl)amino)-6-cyclopropylpyrazine-2-carboxylic acid, 6-cyclopropyl-3-((4'-fluoro-2-(2,2,2-trifluoroethoxy)-[1,1'-biphenyl]-3-yl)amino)pyrazine-2-carboxylic acid, 5-cyclopropyl-2-((3-(3,6-dihydro-2H-pyran-4-yl)-2-ethoxy-6-fluorophenyl)amino)nicotinic acid, 5-cyclopropyl-2-((3-(3,6-dihydro-2H-pyran-4-yl)-2-ethoxy-4-fluorophenyl)amino)nicotinic acid, 2-cyclopropyl-5-((3-(3,6-dihydro-2H-pyran-4-yl)-2-(2,2,2-trifluoroethoxy)phenyl)amino)isonicotinic acid, and (S)-6-cyclopropyl-3-((3-(tetrahydro-2H-pyran-4-yl)-2-((1,1,1-trifluoropropan-2-yl)oxy)phenyl)amino)pyrazine-4-carboxylic acid.

* * * * *